United States Patent
Ding et al.

(10) Patent No.: US 11,928,311 B2
(45) Date of Patent: Mar. 12, 2024

(54) COMMUNICATION METHOD, TERMINAL, SERVER, COMMUNICATION SYSTEM, COMPUTER DEVICE AND MEDIUM

(71) Applicants: Beijing Zhongxiangying Technology Co., Ltd., Beijing (CN); BOE Technology Group Co., Ltd., Beijing (CN)

(72) Inventors: Ming Ding, Beijing (CN); Li Ma, Beijing (CN); Yang Wu, Beijing (CN); Wanwan Tang, Beijing (CN); Dachuan Wang, Beijing (CN); Hong Wang, Beijing (CN); Guangyu Shao, Beijing (CN); Chaozheng Liu, Beijing (CN)

(73) Assignees: Beijing Zhongxiangying Technology Co., Ltd., Beijing (CN); BOE Technology Group Co., Ltd., Beijing (CN)

( * ) Notice: Subject to any disclaimer, the term of this patent is extended or adjusted under 35 U.S.C. 154(b) by 250 days.

(21) Appl. No.: 17/357,955

(22) Filed: Jun. 24, 2021

(65) Prior Publication Data
US 2022/0155916 A1 May 19, 2022

(30) Foreign Application Priority Data
Nov. 18, 2020 (CN) .......................... 202011292740.9

(51) Int. Cl.
*G06F 3/0482* (2013.01)
*G06F 3/04817* (2022.01)
(Continued)

(52) U.S. Cl.
CPC ........ *G06F 3/0482* (2013.01); *G06F 3/04817* (2013.01); *G16H 10/60* (2018.01);
(Continued)

(58) Field of Classification Search
CPC ... G06F 3/0482; G06F 3/04817; G16H 10/60; H04L 67/54; H04L 67/55; H04L 67/12; H04L 67/306
See application file for complete search history.

(56) References Cited

U.S. PATENT DOCUMENTS

2002/0162005 A1* 10/2002 Ueda .................. G06F 21/604
    713/182
2004/0172301 A1* 9/2004 Mihai ................. A61B 5/0002
    705/2

(Continued)

*Primary Examiner* — William L Bashore
*Assistant Examiner* — Gregory A Distefano
(74) *Attorney, Agent, or Firm* — IPro, PLLC

(57) ABSTRACT

The present application discloses a communication method, a terminal, a server, a communication system, a computer device and a medium. The communication method includes that a server establishes a connection and feeds back a display control in response to requests of a first terminal and a second terminal; then, the server feeds back function feedback information in response to a function request of the first terminal, and feeds back function feedback information in response to a menu request of the second terminal; and the servers presents multiple interface components and maintains and updates each interface component in response to management operation of a third user.

11 Claims, 76 Drawing Sheets

(51) Int. Cl.
  *G16H 10/60* (2018.01)
  *G16H 40/20* (2018.01)
  *H04L 67/12* (2022.01)
  *H04L 67/306* (2022.01)
  *H04L 67/54* (2022.01)
  *H04L 67/55* (2022.01)
  *H04L 67/53* (2022.01)

(52) U.S. Cl.
  CPC ............ *G16H 40/20* (2018.01); *H04L 67/12* (2013.01); *H04L 67/306* (2013.01); *H04L 67/54* (2022.05); *H04L 67/55* (2022.05); *H04L 67/53* (2022.05)

(56) References Cited

U.S. PATENT DOCUMENTS

| | | | | |
|---|---|---|---|---|
| 2005/0203771 | A1* | 9/2005 | Achan | G16H 30/20 705/2 |
| 2009/0276487 | A1* | 11/2009 | Jensen | G16H 20/60 709/203 |
| 2012/0136221 | A1* | 5/2012 | Killen | G16H 40/67 600/300 |
| 2016/0048640 | A1* | 2/2016 | Chung | G16Z 99/00 705/3 |
| 2018/0011694 | A1* | 1/2018 | Al-Fuqaha | G06F 8/36 |
| 2018/0018864 | A1* | 1/2018 | Baker | G08B 21/043 |
| 2018/0213378 | A1* | 7/2018 | Brown | H04W 4/70 |
| 2019/0108908 | A1* | 4/2019 | Faulks | G08B 27/005 |

\* cited by examiner billing details

- recharge 1000 yuan  +1000.0元
- cost of surgery  -3000.0元
- medical expenses  -200.0元
- recharge 1000 yuan  +1000.0元
- recharge 1000 yuan  +1000.0元
- recharge 1000 yuan  +1000.0元
- recharge 1000 yuan  +1000.0元

FIG.6b

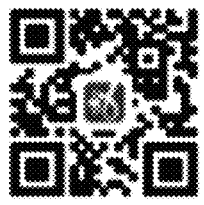
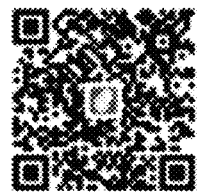
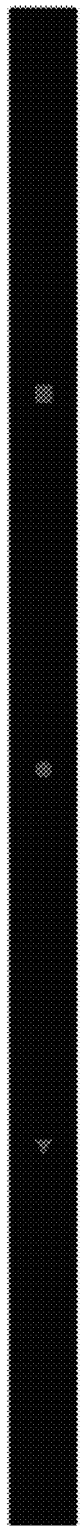
FIG.6d message reminder operation reminder*
operation name: operation under percutaneous endoscopy
chief surgeon: Dr. Tang    operating room: 801    operation time: ████████    operation table: 1 inspection*
inspection item: inspection 1    appointment time: ████████    examination department: internal medicine
inspection position: ward A, 4th floor operation reminder
operation name: operation under percutaneous endoscopy
chief surgeon: Dr. Tang    operating room: 801    operation time: ████████    operation table: 1 operation reminder
operation name: operation under percutaneous endoscopy
chief surgeon: Dr. Tang    operating room: 801    operation time: ████████    operation table: 1

FIG. 7a my medical record

Tang Yi, male, 26 attending doctor: Chen Guozhong admission time recording time:

| chief complaint

| history of present illness

| past medical history

| physical examination

FIG.7b my medical record assistant examination diagnosis and treatment opinions diagnosis

Tang Yi, male, 26 attending doctor Chen Guozhong admission time recording time:

FIG. 7m

FIG.7n

| | | | | | | |
|---|---|---|---|---|---|---|
| authority management | | satisfaction survey management:list of satisfaction questionnaires | | | | |
| nursing information management | | list of satisfaction questionnaires | | | | |
| hospital information management | | | | | | |
| satisfaction survey management | | name of questionnaire | | Advance search | | |
| patient feedback list | | serial | name of questionnaire | status | update time | operation |
| device management | | | | Published | | Unpublished |
| medical record review management | | | | Cancelled | | Published edit delete |
| version management | | | | Cancelled | | Published edit delete |
| | | | | Cancelled | | Published edit delete |
| | | | | Cancelled | | Published edit delete |

COMMUNICATION METHOD, TERMINAL, SERVER, COMMUNICATION SYSTEM, COMPUTER DEVICE AND MEDIUM

CROSS-REFERENCE TO RELATED APPLICATION

The present application claims a priority of the Chinese patent application No. 202011292740.9 filed on Nov. 18, 2020, which is incorporated herein in its entirety.

TECHNICAL FIELD

The present application relates to the field of Internet of Things technologies, and in particular to a communication method, a terminal, a server, a communication system, a computer device and a medium.

BACKGROUND

In the related art, an inpatient department of a hospital has complicated management problems for inpatients and medical staff, which often reduce the work efficiency of the medical staff, increases psychological burden of patients, and affects treatment effect.

SUMMARY

According to a first aspect of the present application, a communication method is provided and applied to a server. The method includes:
  in response to a first login request of a first terminal of a first user, allocating a first identity identifier according to first terminal information in the first login request, and transmitting the first identity identifier and corresponding function control information to the first terminal of the first user;
  establishing a second user account in response to an account operation of a third user and allocating a second identity identifier for a second user; and in response to a second login request of a second terminal of the second user, transmitting corresponding menu control information to the second terminal according to the second identity identifier in the second login request;
  in response to a first function request of the first terminal, transmitting function feedback information to the first terminal according to the first identity identifier and a function control in the first function request;
  in response to a second function request of the second terminal, transmitting function feedback information to the second terminal according to the second identity identifier and a menu control in the second function request; and,
  presenting a plurality of interface components, and maintaining and updating each interface component in response to an management operation of the third user.

Optionally, the plurality of interface components include: at least two of authority management component, nursing information management component, hospital information management component, satisfaction survey component, device management component, medical record review management component or version management component.

Optionally, the server includes an MQTT message queue and a processor; wherein in response to the first function request of the first terminal, transmitting function feedback information to the first terminal according to the first identity identifier and the function control in the first function request, further includes:
  receiving, by the MQTT message queue, the first function request transmitted by the first terminal, and pushing the first function request to the processor;
  generating, by the processor, the function feedback information, according to the first identity identifier and the function control in the first function request, and transmitting the function feedback information to the MQTT message queue, wherein the function feedback information includes the first identity identifier;
  pushing, by the MQTT message queue, the function feedback information to the first terminal according to the first identity identifier;
  wherein in response to the second function request of the second terminal, transmitting function feedback information to the second terminal according to the second identity identifier and the menu control in the second function request, further includes:
  receiving, by the MQTT message queue, the second function request transmitted by the second terminal, and pushing the second function request to the processor;
  generating, by the processor, the function feedback information according to the second identity identifier and the menu control in the second function request, and transmitting the function feedback information to the MQTT message queue, wherein the function feedback information includes the second identity identifier;
  pushing, by the MQTT message queue, the function feedback information to the second terminal according to the second identity identifier.

Optionally, the processor further includes a callback counter; after pushing, by the MQTT message queue, the function feedback information to the first terminal according to the first identity identifier, or, after pushing, by the MQTT message queue, the function feedback information to the second terminal according to the second identity identifier, the communication method further includes:
  transmitting, by the MQTT message queue, callback information to the processor;
  receiving, by the processor, the callback information and triggering the callback counter to count, and judging whether the function feedback information is pushed completely according to a count value of the callback counter.

According to a second aspect of the present application, a communication method is provided and applied to a first terminal. The method includes:
  transmitting a first login request to a server in response to a login operation of a first user, wherein the first login request includes first terminal information;
  receiving a first identity identifier transmitted by the server and presenting multiple function controls corresponding to the first identity identifier, wherein the first identity identifier is allocated by the server according to the first terminal information;
  in response to the first user's selection operation on the function controls, transmitting a first function request to the server, receiving and presenting function feedback information transmitted by the server, wherein the first function request includes the first identity identifier.

Optionally, the multiple function controls include at least two of reminder message control, medical record control, reporting control, bill control, appointment control, propaganda-education control, ordering control, medical record copy control, electronic signature control, satisfaction survey control or file control.

Optionally, in response to the first user's selection operation on the function controls, transmitting the first function request to the server, receiving and presenting function feedback information transmitted by the server, further includes at least one of the following:

in response to a selection operation of the first user on the ordering control, presenting nutrition prompt information, a food selection list, and a time selection control for the first user;

in response to a selection operation of the first user on the bill control, presenting a bill list of the first user and a recharge control; wherein the recharge control is connected to a third-party payment interface;

in response to a selection operation of the first user on the reminder message control, presenting a reminder message list for the first user;

in response to a selection operation of the first user on the medical record control, presenting medical record information of the first user;

in response to a selection operation of the first user on the reporting control, presenting a report list of the first user;

in response to a selection operation of the first user on the appointment control, presenting an appointment list of the first user; wherein the appointment list includes an examination appointment and a surgery appointment;

in response to a selection operation of the first user on the propaganda-education control, presenting a propaganda-education list;

in response to a selection operation of the first user on the medical record copy control, presenting a medical record copy application form;

in response to a selection operation of the first user on the electronic signature control, presenting a signature list;

in response to a selection operation of the first user on the satisfaction survey control, presenting a questionnaire; or in response to a selection operation of the first user on the file control, presenting corresponding user files.

Optionally, the communication method further includes:

receiving the first identity identifier transmitted by the server, and presenting user information corresponding to the first identity identifier as well as a reminder message corresponding to the first identity identifier;

wherein the user information includes at least one of user name, gender, hospitalization information, medical staff information, or user's QR code information;

the reminder message includes at least one of an examination reminder, an operation reminder, or a medical record receipt reminder.

Optionally, the server includes an MQTT message queue and a processor;

wherein in response to the first user's selection operation on the function controls, transmitting the first function request to the server, receiving and presenting function feedback information transmitted by the server, further includes:

in response to the first user's selection operation on the function controls, transmitting the first function request to the MQTT message queue based on the MQTT protocol, so that the MQTT message queue pushes the first function request to the processor;

receiving and presenting the function feedback information transmitted by the server, wherein the function feedback information is transmitted by the processor according to the received first function request, and pushed to the first terminal corresponding to the first identity identifier through the MQTT message queue.

According to a third aspect of the present application, a communication method is provided and applied to a second terminal. The method includes:

transmitting a second login request to a server in response to a login operation of a second user, wherein the second login request includes a second identity identifier, and the second identity identifier is allocated by the server in response to a management operation of a third user;

presenting multiple menu controls corresponding to the second identity identifier;

in response to the second user's selection operation on the menu controls, transmitting a second function request to the server, receiving and presenting function feedback information transmitted by the server, wherein the second function request includes the second identity identifier.

Optionally, the multiple menu controls include at least two of ward overview control, bed list control, nursing plan control, physical sign event control, surgical monitoring control, shift log control, or scheduling plan control.

Optionally, in response to the second user's selection operation on the menu controls, transmitting the second function request to the server, receiving and presenting function feedback information transmitted by the server, further includes at least one of the following:

in response to the second user's selection operation on the ward overview control, presenting bed information of a ward where the second user is located and corresponding patient control; in response to the second user's selection operation on the patient control, presenting identity authentication; in response to the second user's authentication operation of the identity authentication, presenting user information, expense information, surgery information, nursing work information, examination information, inspection information, physical sign information and medical order information of a corresponding patient;

in response to the second user's selection operation on the nursing plan control, presenting nursing plan information of the ward where the second user is located; wherein the nursing plan information includes today's physical sign measurement information, today's risk assessment information, today's nursing item information, and today's medical order information;

in response to the second user's selection operation on the physical sign event control, presenting physical sign event information of the ward where the second user is located; wherein the physical sign event information includes abnormal body temperature data information, abnormal pulse data information, abnormal breathing data information, abnormal blood pressure data information and early risk warning information;

in response to the second user's selection operation on the surgical monitoring control, presenting surgical monitoring information of the ward where the second user is located; wherein the surgical monitoring information includes patient information, medical information and status information corresponding to each surgery;

in response to the second user's selection operation on the shift log control, presenting shift log information of the ward where the second user is located; wherein the shift log information includes nursing information of each patient in the ward where the second user is located; or, in response to the second user's selection operation on the scheduling plan control, presenting scheduling plan information of the ward where the second user is located; wherein the scheduling plan information includes schedule information of each medical staff in the ward where the second user is located.

Optionally, the server includes an MQTT message queue and a processor;

wherein in response to the second user's selection operation on the menu controls, transmitting the second function request to the server, receiving and presenting function feedback information transmitted by the server, further includes:

in response to the second user's selection operation on the menu controls, transmitting the second function request to the MQTT message queue based on the MQTT protocol, so that the MQTT message queue pushes the second function request to the processor;

receiving and presenting the function feedback information transmitted by the server, wherein the function feedback information is transmitted by the processor according to the received second function request, and pushed to the second terminal corresponding to the second identity identifier through the MQTT message queue.

According to a fourth aspect of the present application, a server for implementing the communication method of the first aspect is provided and includes:

a processor configured to bind a first terminal, and allocate a first identity identifier and corresponding function control information to the first terminal according to first terminal information; generate function feedback information according to a first function request of the first terminal; connect with a second terminal and transmit corresponding menu control to the second terminal according to a second identity identifier of the second terminal; and generate function feedback information according to a second function request of the second terminal;

an MQTT message queue configured to, based on an MQTT protocol, connect the first terminal, the second terminal, and the processor, respectively; receive the first function request of the first terminal or the second function request of the second terminal, and push the first function request of the first terminal or the second function request of the second terminal to the processor; receive the function feedback information generated by the processor, and push the function feedback information to the first terminal or the second terminal.

According to a fifth aspect of the present application, a terminal for implementing the communication method of the second aspect is provided and includes:

a display unit including a binding control and a function control;

wherein the binding control is configured to transmit a first login request to the server to establish a binding connection, and obtain a first identity identifier and a plurality of corresponding function controls according to first terminal information in the first login request;

the function control is configured to transmit a first function request to the server to receive and present function feedback information transmitted by the server; wherein the first function request includes the first identity identifier;

a communication unit configured to communicate with the server.

According to a sixth aspect of the present application, a terminal for implementing the communication method of the third aspect is provided and includes:

a display module including a login control and menu controls;

wherein the login control is configured to transmit a second login request to a server to obtain multiple corresponding menu controls according to a second identity identifier of the terminal;

the menu controls are configured to transmit a second function request to the server to receive and present function feedback information transmitted by the server; wherein the second function request includes the second identity identifier;

a communication module configured to communicate with the server.

Optionally, the menu controls include at least two of ward overview control, bed list control, nursing plan control, physical sign event control, surgical monitoring control, shift log control, or scheduling plan control.

According to a seventh aspect of the present application, a computer device is provided and includes: a memory, a processor, and a computer program stored on the memory and executable on the processor. The processor executes the computer program to implement the foregoing method.

It is to be understood that the contents in this section are not intended to identify the key or critical features of the embodiments of the present application, and are not intended to limit the scope of the present application. Other features of the present application will become readily apparent from the following description.

BRIEF DESCRIPTION OF THE DRAWINGS

The drawings are included to provide a better understanding of the application and are not to be construed as limiting the application. Wherein:

FIG. 6a to FIG. 6d are schematic diagrams of billing function of a first terminal according to an embodiment of the present application;

FIG. 8a to FIG. 8j are schematic diagrams showing authority management of a server according to an embodiment of the present application;

DETAILED DESCRIPTION

Reference will now be made in detail to the exemplary embodiments of the present application, examples of which are illustrated in the accompanying drawings, wherein the various details of the embodiments of the present application are included to facilitate understanding and are to be considered as exemplary only. Accordingly, a pedestrian skilled in the art should appreciate that various changes and modifications can be made to the embodiments described herein without departing from the scope and spirit of the present application. Also, descriptions of well-known functions and structures are omitted from the following description for clarity and conciseness.

Figure 1:
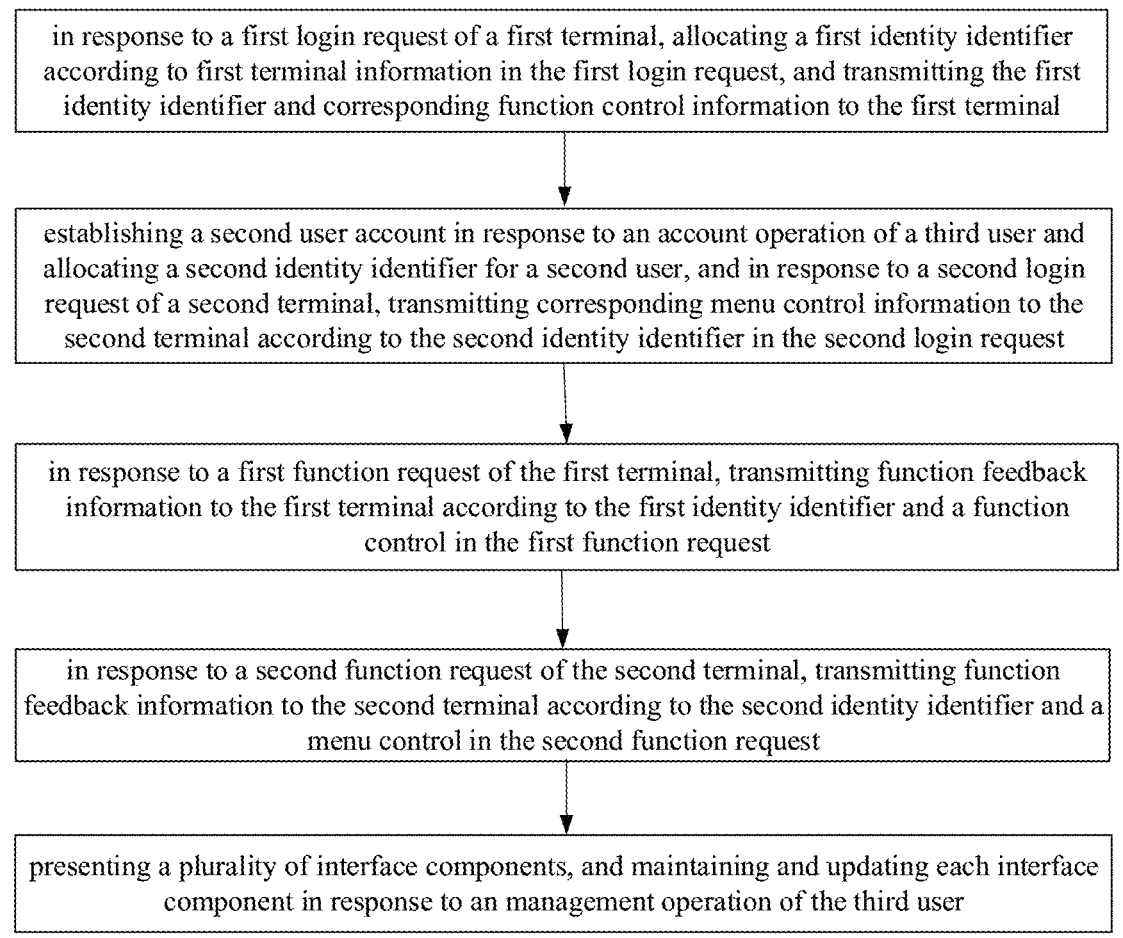
FIG. 1 is a flowchart of a communication method applied to a server according to an embodiment of the present application.

As shown in FIG. 1, one embodiment of the present application provides a communication method performed by a server. The communication method includes: in response to a first login request of a first terminal, allocating a first identity identifier according to first terminal information in the first login request, and transmitting the first identity identifier and corresponding function control information to the first terminal; establishing a second user account in response to an account operation of a third user and allocating a second identity identifier for a second user, and in response to a second login request of a second terminal, transmitting corresponding menu control information to the second terminal according to the second identity identifier in the second login request; in response to a first function request of the first terminal, transmitting function feedback information to the first terminal according to the first identity identifier and a function control in the first function request; in response to a second function request of the second terminal, transmitting function feedback information to the second terminal according to the second identity identifier and a menu control in the second function request; and, presenting a plurality of interface components, and maintaining and updating each interface component in response to an management operation of the third user.

In this embodiment, the server interacts with the first terminal and the second terminal to realize management of the first terminal and the second terminal. Meanwhile, the server presents a plurality of interface components and uses the interface components to realize background management of the first terminal and the second terminal, thereby enhancing management of inpatients and medical staff in the existing inpatient system, simplifying the existing management system, effectively improving user experience of patients and the medical staff, and realizing information interaction, management and maintenance of smart wards, which has a wide range of application prospects.

Figure 2:
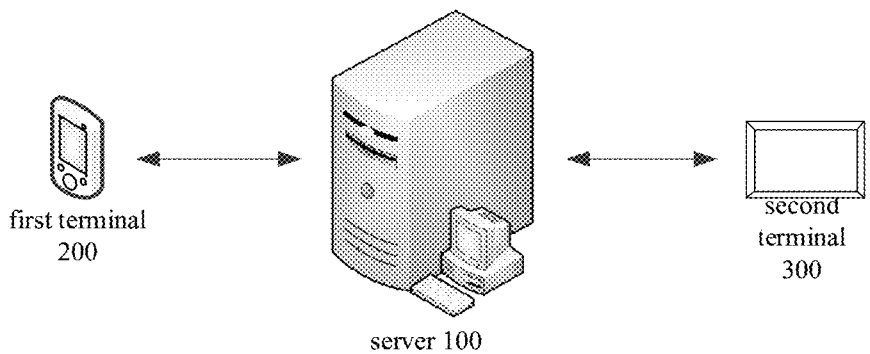
FIG. 2 is a schematic diagram of an application scenario of a communication system according to an embodiment of the present application.

In a specific example, as shown in FIG. 2, it is a schematic diagram of an application scenario of a communication system according to an embodiment of the present application. A first terminal is a mobile terminal provided to an inpatient, such as a mobile terminal such as a tablet computer or a smart phone arranged near a bedside of a hospital bed, for facilitating the inpatient to inquire about personal treatment information, examination reports, surgery appointment, ordering information and cost information, etc. A second terminal is a display terminal provided to the medical staff, such as a large display device arranged at a nurse station, for facilitating the medical staff to inquire about an overall situation, individual situation, daily nursing needs and examination needs of inpatients, duty information and scheduling information, etc. A server is a background system that interacts with the first terminal and the second terminal, presents and maintains as well as updates various interface components, and manages the first terminal and the second terminal through the various interface components.

Figure 3:
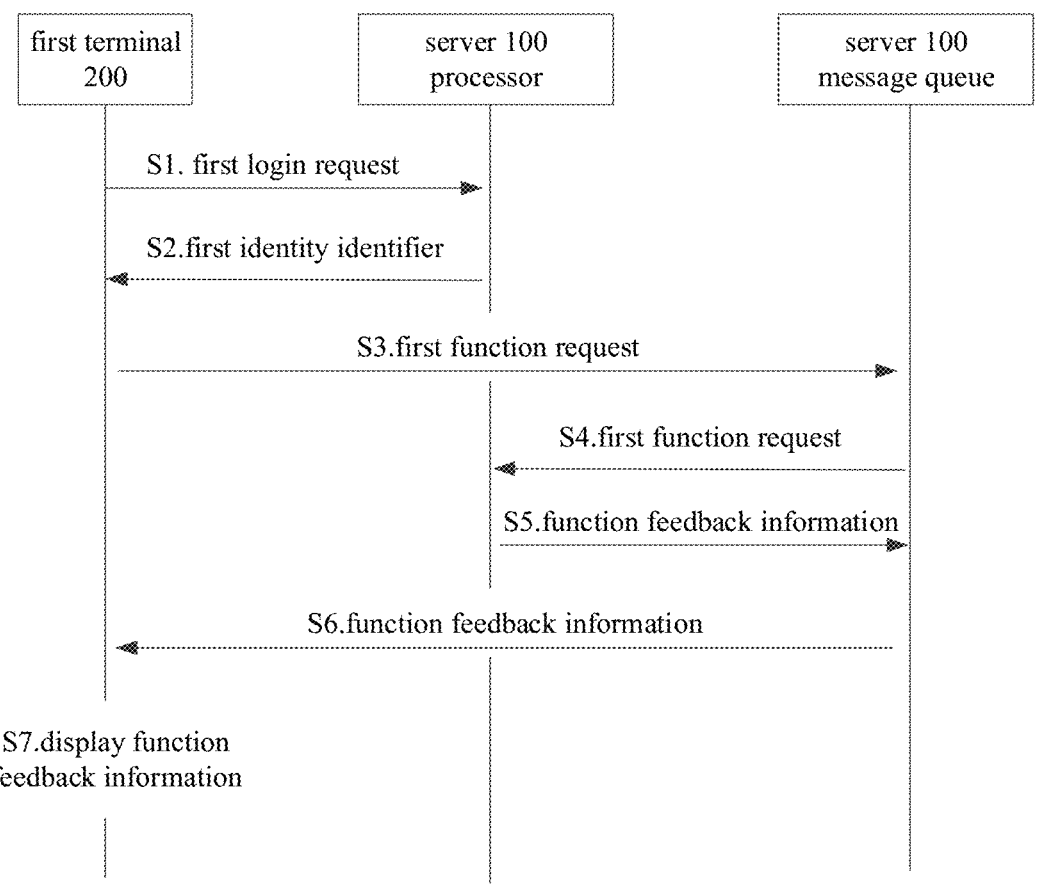
FIG. 3 is a swim-lane diagram showing communication interaction between a first terminal and a server according to an embodiment of the present application.

Specifically, as shown in FIG. 3, information interaction between the first terminal and the server is taken as an example for illustration. It is worth noting that in this embodiment, in order to facilitate description of interactive functions between the server and the first terminal as well as the second terminal, the server is divided into a processor used for access and background management, and a message queue used for message interaction. Those skilled in the art may make settings according to actual application requirements. For example, the server may be divided into a first sub-server used for access and background management and a second sub-server used for message interaction, which is not specifically limited in the present application.

Firstly, in a first step S1, a first terminal 200 transmits a first login request to a server 100 in response to a login operation of a first user, where the first login request includes first terminal information.

Figure 4A:
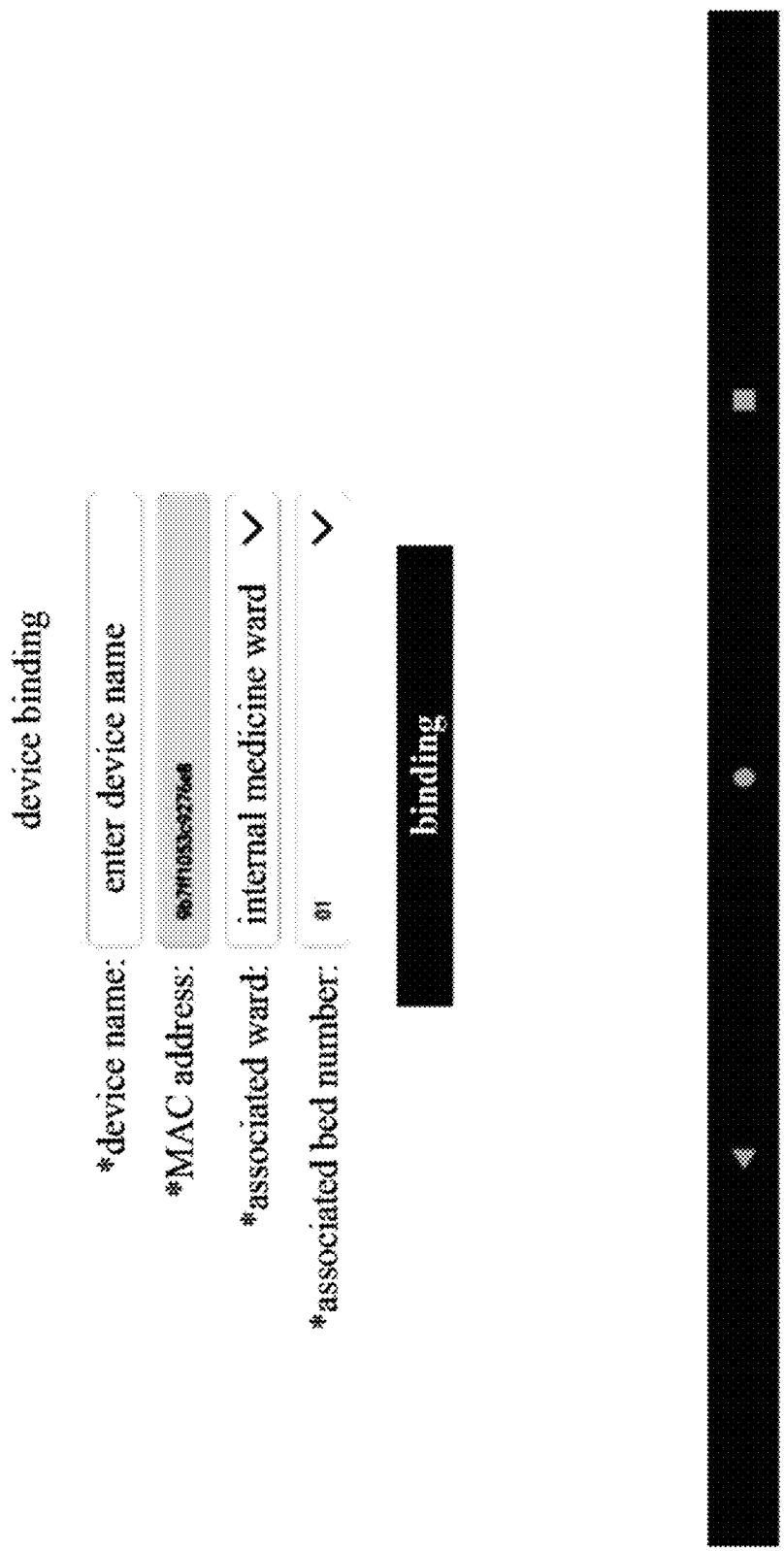
FIG. 4a to FIG. 4b are schematic diagrams of a first terminal accessing a server according to an embodiment of the present application.

In this embodiment, as shown in FIG. 4a, the first terminal information is information that uniquely identifies the first terminal, such as a physical address of the first terminal. The first terminal transmits a login request to the server 100 according to the first terminal information to establish a connection with the processor of the server 100, i.e., realizing a binding operation between the first terminal and the server.

Secondly, in a second step S2, the processor of the server identifies a type of the first terminal and allocates a first identity identifier according to the first terminal information in the login request.

In this embodiment, in a case that the processor of the server identifies the first terminal as a mobile terminal used by an inpatient, the processor of the server allocates, to the first terminal, the first identity identifier and corresponding function control information, such as function controls displayed by the first terminal, and permissions of the inpatient in various function controls. The first identity identifier can indicate the type of the first terminal, so that in subsequent message interaction, the first terminal performs communication interaction with the message queue of the server through the first identity identifier. Meanwhile, the first identity identifier can further facilitate the message queue of the server to classify and manage the first terminal.

Meanwhile, the first terminal receives the first identity identifier transmitted by the server and presents a plurality of function controls corresponding to the first identity identifier.

Figure 4B:
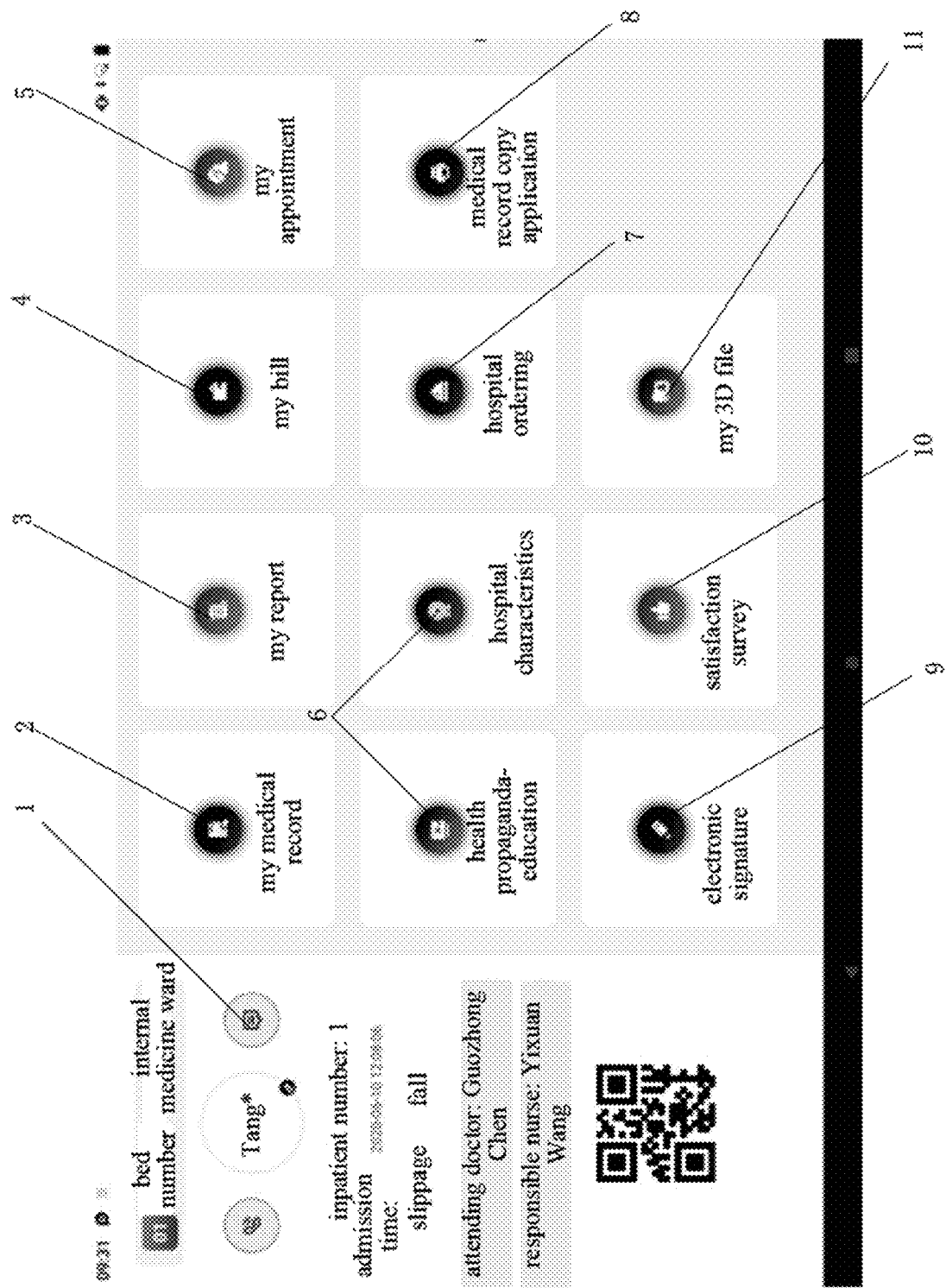

In this embodiment, as shown in FIG. 4b, the plurality of function controls presented by the first terminal, include: a reminder message control 1, a medical record control 2, a reporting control 3, a bill control 4, an appointment control 5, a propaganda-education control 6, an ordering control 7, a medical record copy control 8, an electronic signature control 9, a satisfaction survey control 10 and a file control 11.

It should be noted that this embodiment is only used to illustrate a specific implementation of the present application, and the number and functions of the function controls are not limited. Those skilled in the art can select appropriate function controls according to actual application requirements, which will not be repeated here.

Finally, the first terminal transmits a first function request to the server in response to a selection operation of the first user on the function controls, receives and presents function feedback information transmitted by the server, where the first function request includes the first identity identifier.

In this embodiment, the first user who uses the first terminal can obtain relevant information and perform operations such as making an appointment, order and recharge, through multiple function controls presented by the first terminal. Thus specifically includes following steps.

In a third step S3, the first terminal transmits a first function request to the message queue of the server in response to a selection operation of the first user on the function controls.

In this embodiment, in response to the selection operation on the function controls presented on the first terminal, i.e., clicking one function control, the first terminal transmits the first function request to the message queue of the server, and the first function request includes function control information and the first identity identifier. Specifically, in response to the selection operation of the first user on the function controls, the first terminal transmits the first function request to a MQTT message queue based on the MQTT protocol. That is, the first terminal and the message queue of the server implement communication interaction through the MQTT protocol.

In a fourth step S4, the message queue of the server receives the first function request transmitted by the first terminal, and pushes the first function request to the processor of the server.

In this embodiment, the message queue of the server parses the first function request to obtain the first identity identifier of the first terminal, determines a communication process according to the first identity identifier, and uses the MQTT message queue to push the first function to the processor.

In a fifth step S5, the processor of the server generates function feedback information according to the first function request, and transmits the function feedback information to the message queue of the server.

In this embodiment, the processor of the server processes the first function request, and returns the function feedback information required by the first user according to the first function request, for example, returning result information requested by the first function request to the MQTT message queue of the server.

In a sixth step S6, the message queue of the server pushes the function feedback information to the first terminal according to the first identity identifier in the first function request.

In this embodiment, the MQTT message queue determines a message pusher according to the first identity identifier, and pushes the function feedback information to the first terminal according to the first identity identifier.

It is worth noting that based on the MQTT protocol, by categorizing the first terminal and setting message processing and push rules according to different topics and subscriptions, the present application can transmit a message to each first terminal and transmit a message to a designated first terminal. For example, inpatients may be classified into internal medicine patients and surgical patients, and correspondingly, a first terminal used by each internal medicine patient is grouped as an internal medicine device, and a first terminal used by each surgical patient is grouped as a surgical device. In a case that a message is directed to internal medicine devices, the message is pushed to all the internal medicine devices, but not to the surgical device. Similarly, in a case that a message is directed to surgical devices, the message is pushed to all the surgical devices, but not to the internal medicine devices. In this embodiment, different topics are set through the MQTT message queue, and each first terminal is grouped according to different grouping rules and set to subscribe to a topic of each corresponding group, thereby realizing group push of the MQTT message queue.

In a seventh step S7, the first terminal receives and presents the function feedback information transmitted by the server.

In this embodiment, the first terminal receives the function feedback information pushed by the MQTT message queue, and displays according to the function feedback information, thereby completing interaction process of the first terminal—server message queue—server processor—server message queue—the first terminal. Through the function controls presented by the first terminal, the first terminal realizes the communication interaction with the server.

In an optional embodiment, the processor of the server further includes a callback counter. After the MQTT message queue pushes the function feedback information to the first terminal according to the first identity identifier, or after the MQTT message queue pushes the function feedback information to the second terminal according to the second identity identifier, the communication method further includes that the MQTT message queue transmits callback information to the processor; the processor receives the callback information and triggers the callback counter to count, and whether the function feedback information has been pushed completely is judged according to a count value of the callback counter.

In this embodiment, by setting the callback counter in the processor of the server to monitor the message push of the MQTT message queue, it can effectively improve an accuracy of message transmission by the MQTT message queue, thereby ensuring timeliness of interaction between the first terminal and the server, and support communication interaction between the server and multiple terminals.

Further, considering that the first terminal has a disconnection problem due to network reasons or other reasons, in an optional embodiment, when the first terminal is disconnected and reconnects to the processor of the server, the first terminal transmits a first function request to the MQTT message queue of the server. The first function request further includes a historical data request. The historical data request is pushed to the processor via the MQTT message queue. The processor generates a historical data packet and function feedback information according to the historical data request, and transmits them to the MQTT message queue. Then, the MQTT message queue pushes the historical data packet and the function feedback information to the corresponding first terminal.

In this embodiment, when the first terminal loses historical data due to disconnection or other reasons, the first terminal requests historical data while transmitting the first function request in response to the first user's selection operation, thereby obtaining the historical data and effectively improving the user experience of the first user.

Further, considering problems that the first terminal cannot connect to the processor of the server after the first terminal is disconnected, in an optional embodiment, the first terminal further includes a reconnection counter. Specifically, when the first terminal is disconnected and reconnects with the server, the first terminal transmits a first login request to the server, and the reconnection counter starts counting. In a case that the connection is successful, the reconnection counter is cleared; otherwise, the first terminal transmits the first login request to the server again, and the reconnection counter continues counting. When the number of times that the first terminal continuously transmits the first login request to the server exceeds a preset reconnection threshold, the first terminal stops transmitting the first login request to the server.

Based on the foregoing embodiment, one embodiment of the present application further provides a terminal including a display unit and a communication unit. The display unit includes a binding control and a function control. The binding control is configured to transmit a first login request to the server to establish a binding connection, and obtain a first identity identifier and a plurality of corresponding function controls according to first terminal information in the first login request. The function control is configured to transmit a first function request to the server to receive and present function feedback information transmitted by the server. The first function request includes the first identity identifier. The communication unit is configured to communicate with the server.

The terminal provided in this embodiment is the first terminal near a bedside of a hospital bed. By interacting with the server, the terminal enables the inpatient to inquire about personal treatment information, examination reports, surgery appointment, ordering information and cost information, thereby simplifying the existing management system, effectively improving user experience of patients and the medical staff, and realizing information interaction, management and maintenance of smart wards, which has a wide range of application prospects. The specific implementation is the same as the foregoing embodiment, and will not be repeated here.

For the foregoing function controls, details are described hereinafter.

Function Control Application Scenario 1: Ordering Control.

As shown in FIG. 5a to FIG. 5d, in response to a selection operation of the first user on an ordering control, the first terminal presents nutrition prompt information, a food selection list, and a time selection control for the first user.

In this application scenario, when the first user clicks on the "ordering control" of the first terminal, the first terminal transmits an ordering request to the message queue of the server. The ordering request is pushed to the processor via the MQTT message queue. The processor generates function feedback information and pushes the function feedback information to the first terminal via the MQTT message queue. The first terminal presents the function feedback information.

Figure 5A:
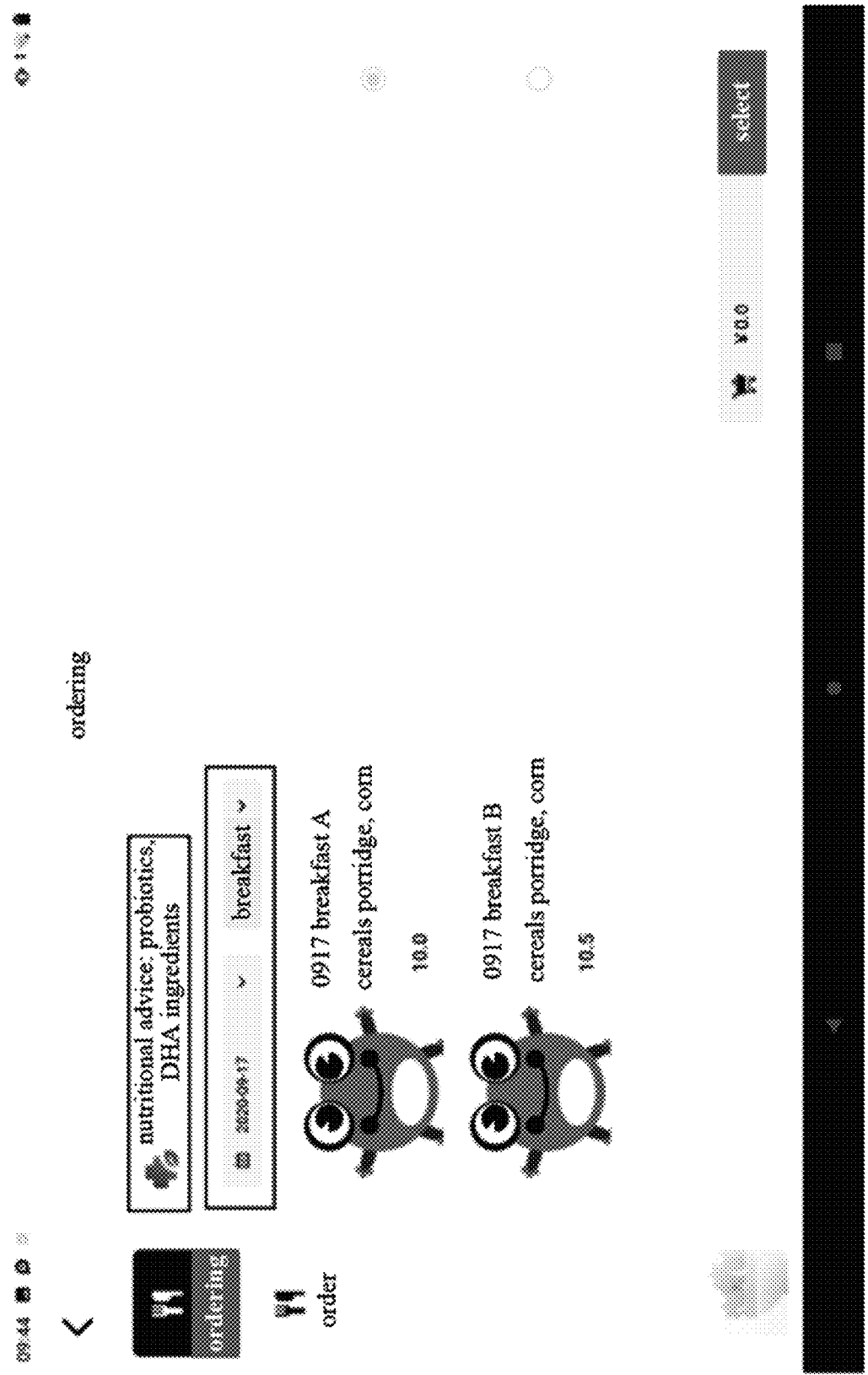
FIG. 5a to FIG. 5d are schematic diagrams of ordering function of a first terminal according to an embodiment of the present application.
Figure 5B:
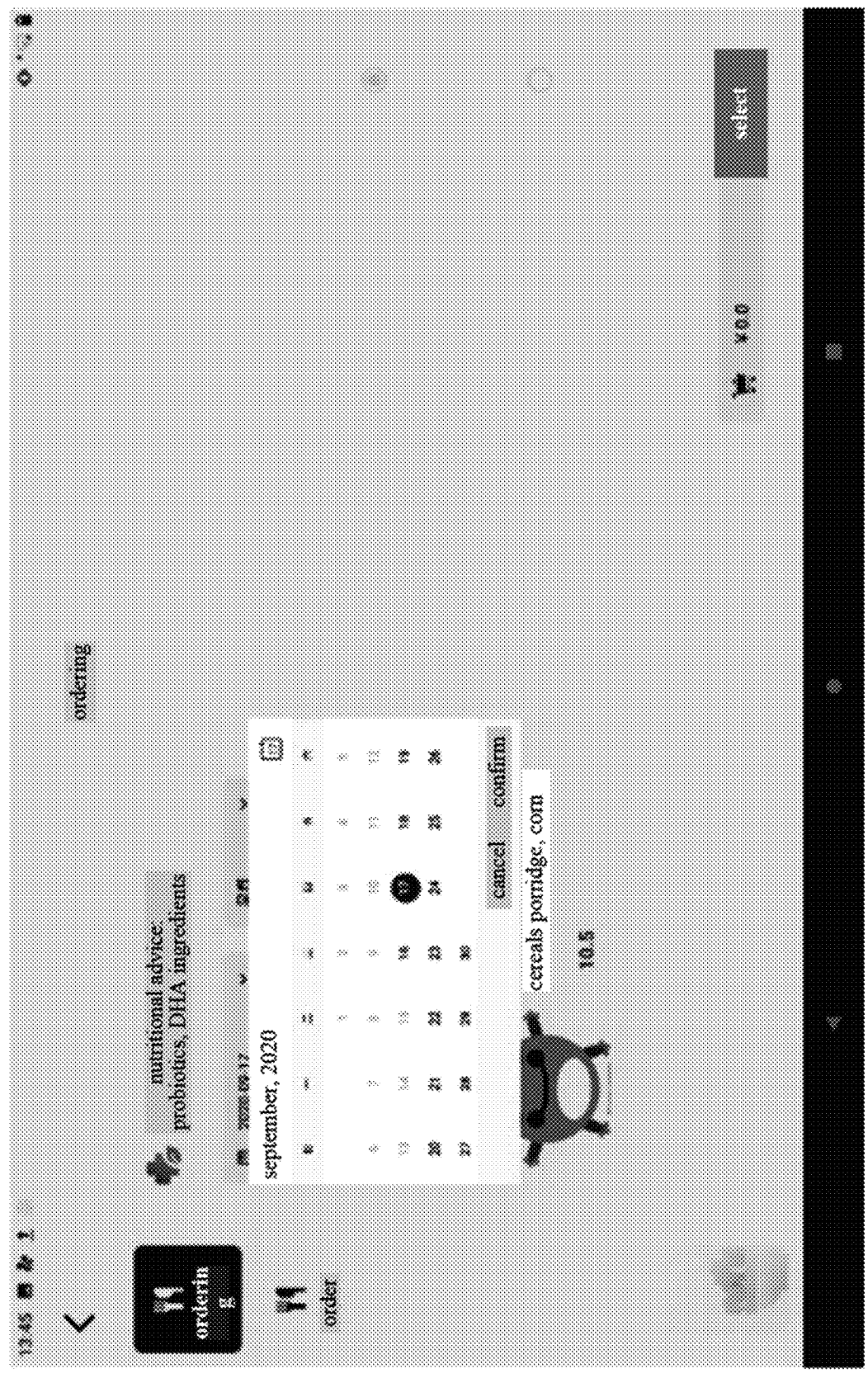
Figure 5C:
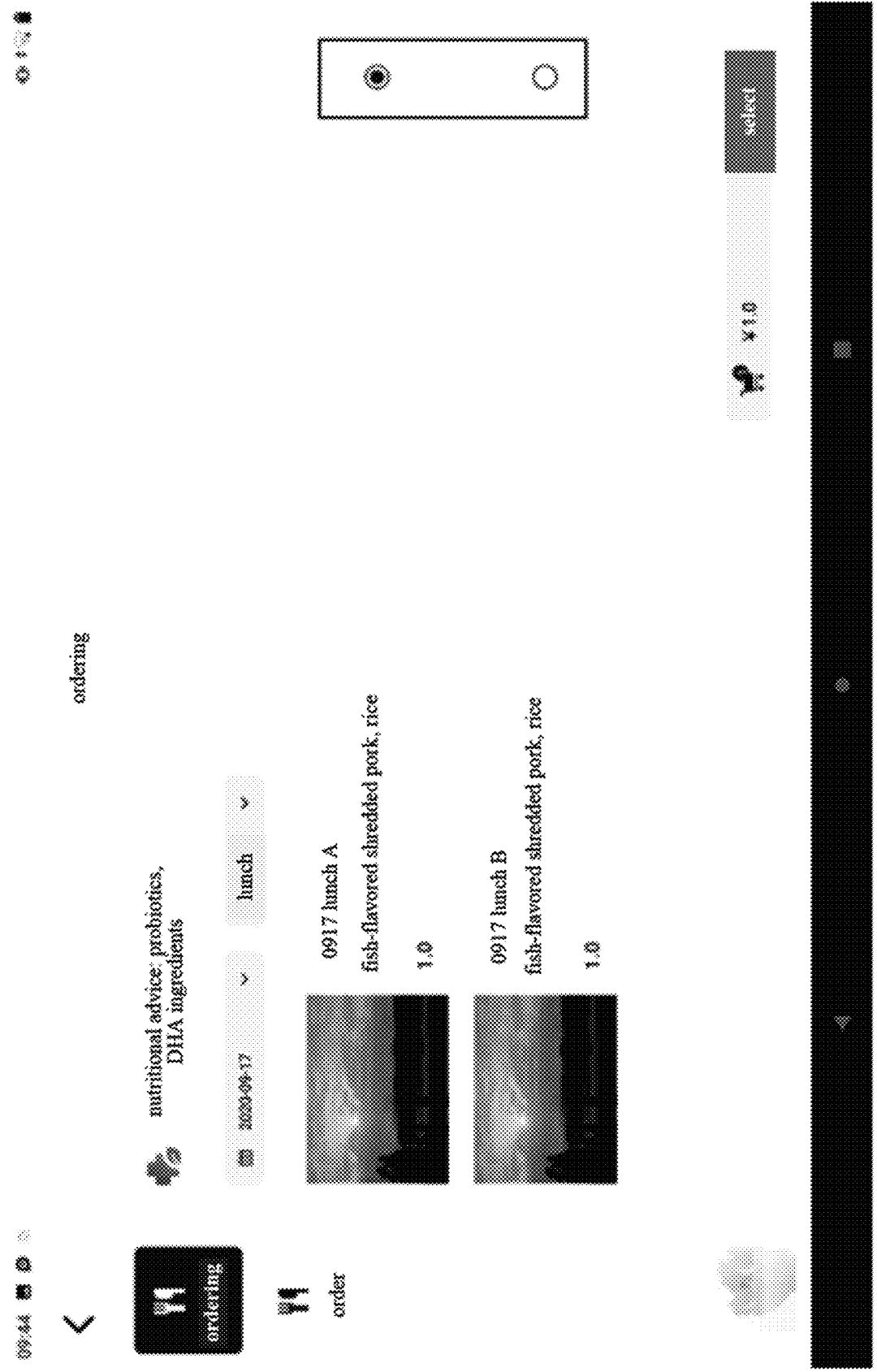
Figure 5D:
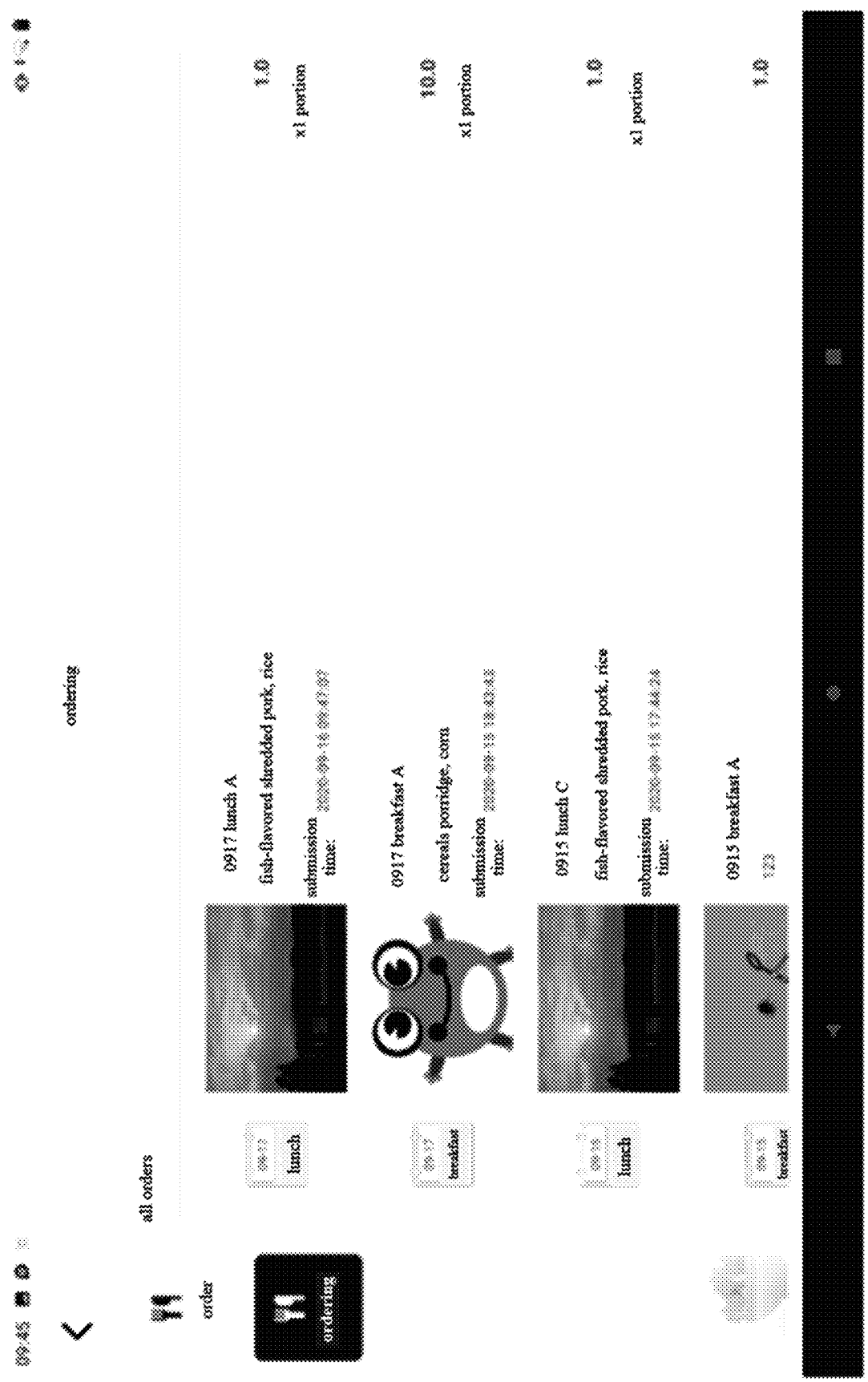

In response to the first user's selection, as shown in FIG. 5a, the first terminal presents nutrition prompt information for the first user, and displays a food selection list suitable for the first user according to the nutrition prompt information. As shown in FIG. 5b, date and time for ordering can be selected according to presented time selection space. As shown in FIG. 5c, the lunch on Sep. 17, 2020 is selected. After confirming the selection, an order is generated and stored in an order list as shown in FIG. 5d, thereby facilitating inpatients or their families to inquire.

It is worth noting that this embodiment presents a corresponding food selection list according to specific situations of an inpatient, which is merely used to illustrate the specific implementation of the present application. The present application is not limited to this, and those skilled in the art may make settings according to actual application needs, which will not be repeated here.

Function Control Application Scenario 2: Billing Control.

In response to a selection operation of the first user on a bill control, the first terminal presents a bill list of the first user and a recharge control. The recharge control is connected to a third-party payment interface.

In this application scenario, when the first user clicks on the "billing control" of the first terminal, the first terminal transmits a bill query request to the message queue of the server. The bill query request is pushed to the processor via the MQTT message queue. The processor generates function feedback information and pushes the function feedback information to the first terminal via the MQTT message queue. The first terminal presents the function feedback information.

Figure 6A:
Figure 6C:
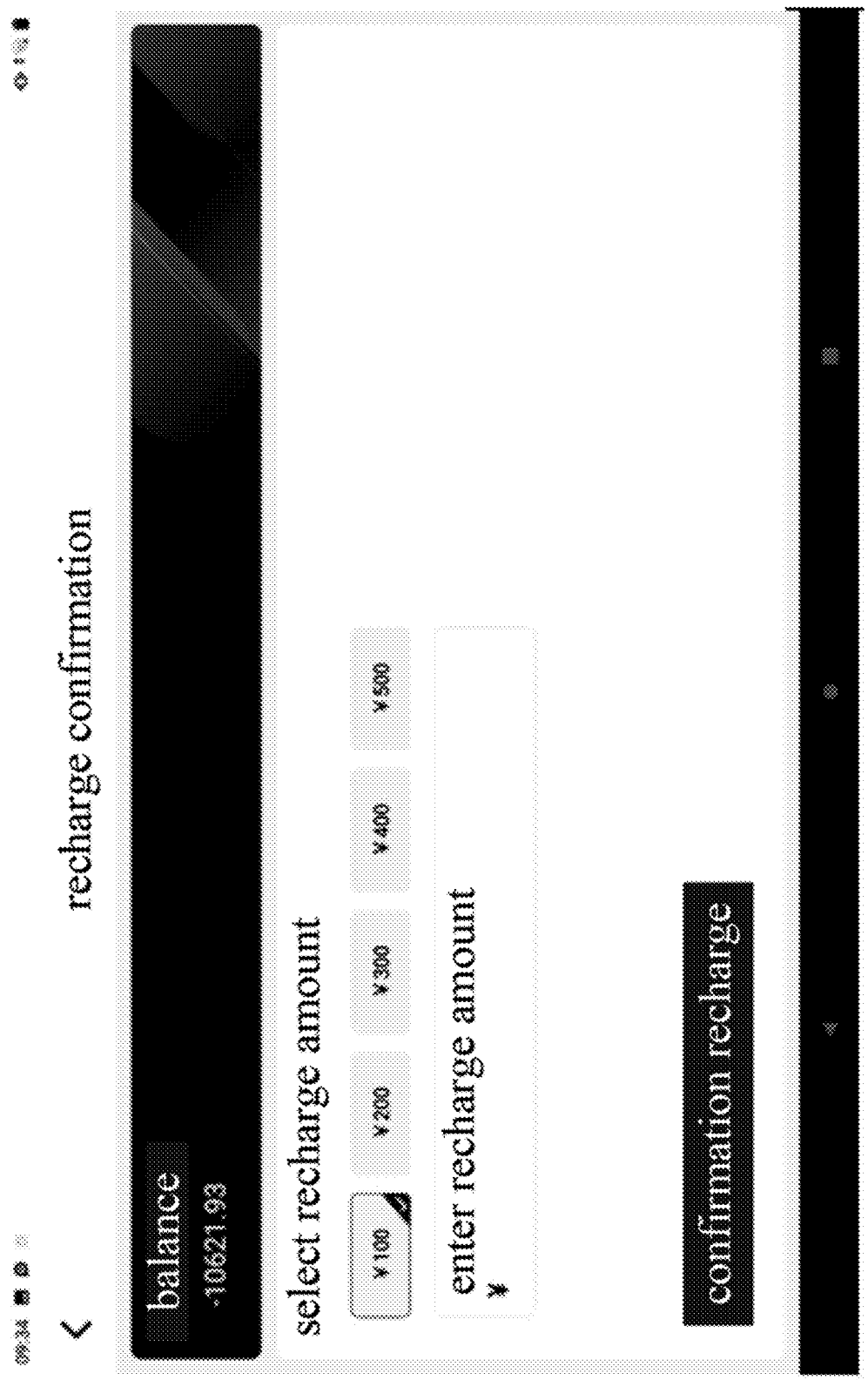

In response to the first user's selection, the first terminal presents billing information of the first user. As shown in FIG. 6a, the billing information includes billing basic information, such as total cost, advance payment and balance information, and a recharge control under the billing basic information. Further, as shown in FIG. 6b, the billing information includes billing details presented according to dates in a case of selecting data. The first user can perform a recharge operation through the recharge control on the first terminal according to the cost situation. As shown in FIG. 6c, the first terminal further displays a current balance (including arrears) through the recharge control, and provides a variety of recharge amount options, or provides a space for directly entering a desired amount. As shown in FIG. 6d, online recharge is realized through a third-party payment interface such as WeChat payment or Alipay payment connected with the recharge control. Through the billing control, it is convenient for inpatients or their families to perform billing operations and online recharge, thereby avoiding queuing for payment and other operations, and then reducing the workload of hospital staff and improving the user experience of inpatients or their families as saving time and effort.

Function Control Application Scenario 3: Reminder Message Control.

In response to a selection operation of the first user on a reminder message control, the first terminal presents a reminder message list for the first user.

In this application scenario, when the first user clicks on the "reminder message list" of the first terminal, the first terminal transmits a reminder message query request to the message queue of the server. The reminder message request is pushed to the processor via the MQTT message queue. The processor generates function feedback information and pushes the function feedback information to the first terminal via the MQTT message queue. The first terminal presents the function feedback information.

In response to the first user's selection, as shown in FIG. 7a, the first terminal presents the first user's message reminder. For example, the first user's message reminder may be a surgical reminder such as related information including a name of an operation, chief surgeon, an operating room. For another example, the first user's message reminder may be an examination reminder, including examination items, examination positions and appointment time.

Through the reminder message control, it is convenient for inpatients or their families to clearly understand the reminder, so as to arrange examination time and operation time reasonably, thereby avoid missing the examination time due to busyness, which helps to stabilize the mood of the inpatients or their families and relieve the mood of the inpatients or their families, and has practical application significance.

Function Control Application Scenario 4: Medical Record Control.

In response to a selection operation of the first user on a medical record control, the first terminal presents medical record information of the first user.

In this application scenario, when the first user clicks on the "medical record control" of the first terminal, the first terminal transmits a medical record query request to the message queue of the server. The medical record query request is pushed to the processor via the MQTT message queue. The processor generates function feedback information and pushes the function feedback information to the first terminal via the MQTT message queue. The first terminal presents the function feedback information.

Figure 7C:
FIG. 7a to FIG. 7s are schematic diagrams showing functions of various function controls of a first terminal according to an embodiment of the present application.

As shown in FIG. 7b and FIG. 7c, in response to the first user's selection, the first terminal presents the first user's medical record information, such as current medical history, past history, physical examination, auxiliary examination, diagnosis and treatment opinions, and diagnosis, which is convenient for inpatients or their families to view.

Function Control Application Scenario 5: Reporting Control.

In response to a selection operation of the first user on a reporting control, the first terminal presents a report list of the first user.

In this application scenario, when the first user clicks on the "reporting control" of the first terminal, the first terminal transmits a report query request to the message queue of the server. The report query request is pushed to the processor via the MQTT message queue. The processor generates function feedback information and pushes the function feedback information to the first terminal via the MQTT message queue. The first terminal presents the function feedback information.

Figure 7D:
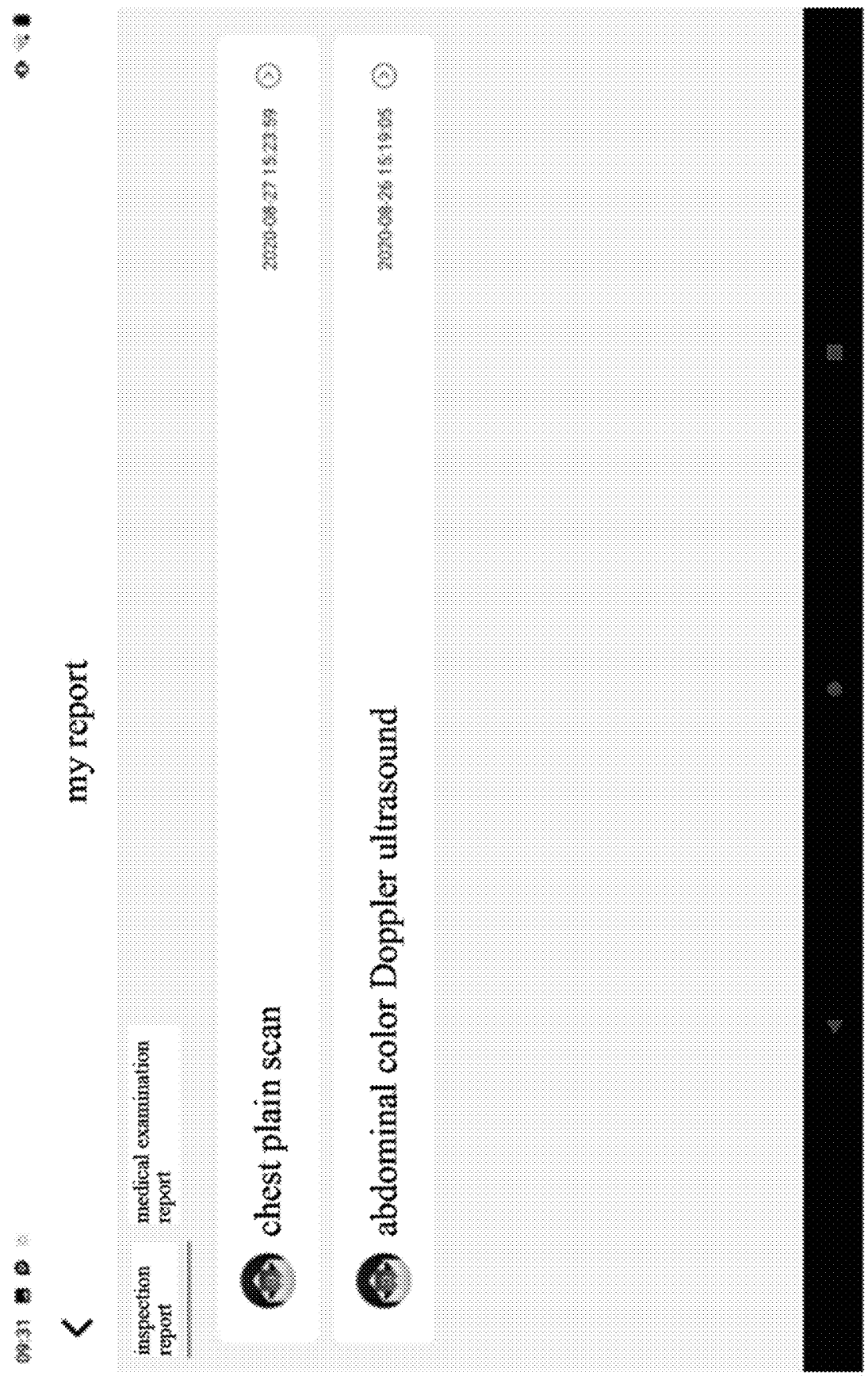
Figure 7E:
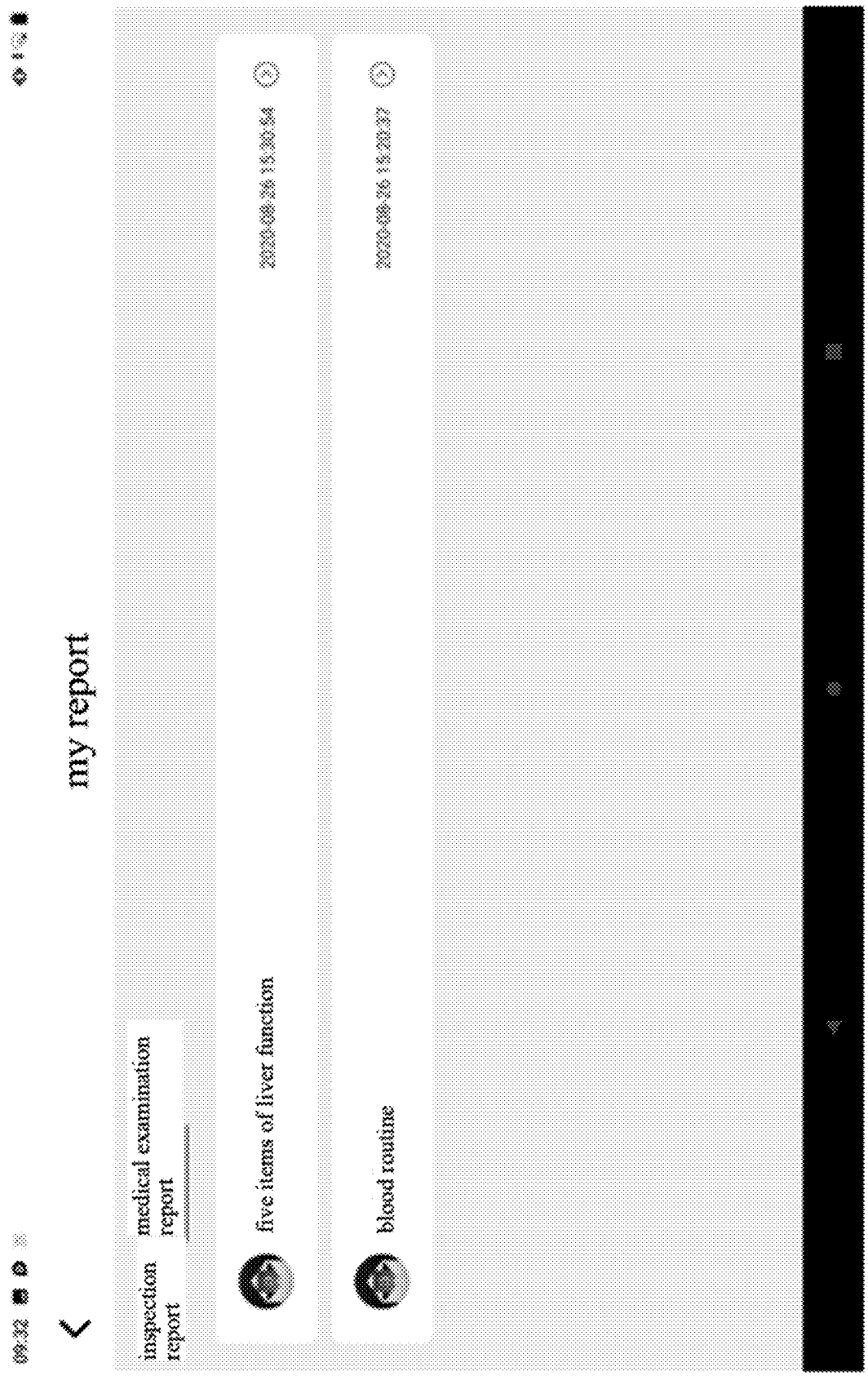

As shown in FIG. 7d and FIG. 7e, in response to the first user's selection, the first terminal presents the first user's examination report and inspection report information, which is convenient for inpatients or their families to view. For example, the first user's examination report may be B-ultrasound, CT or other examination report; and the first user's inspection report may be five items of liver function, blood routine, or other inspection reports.

Figure 7F:
Figure 7G:
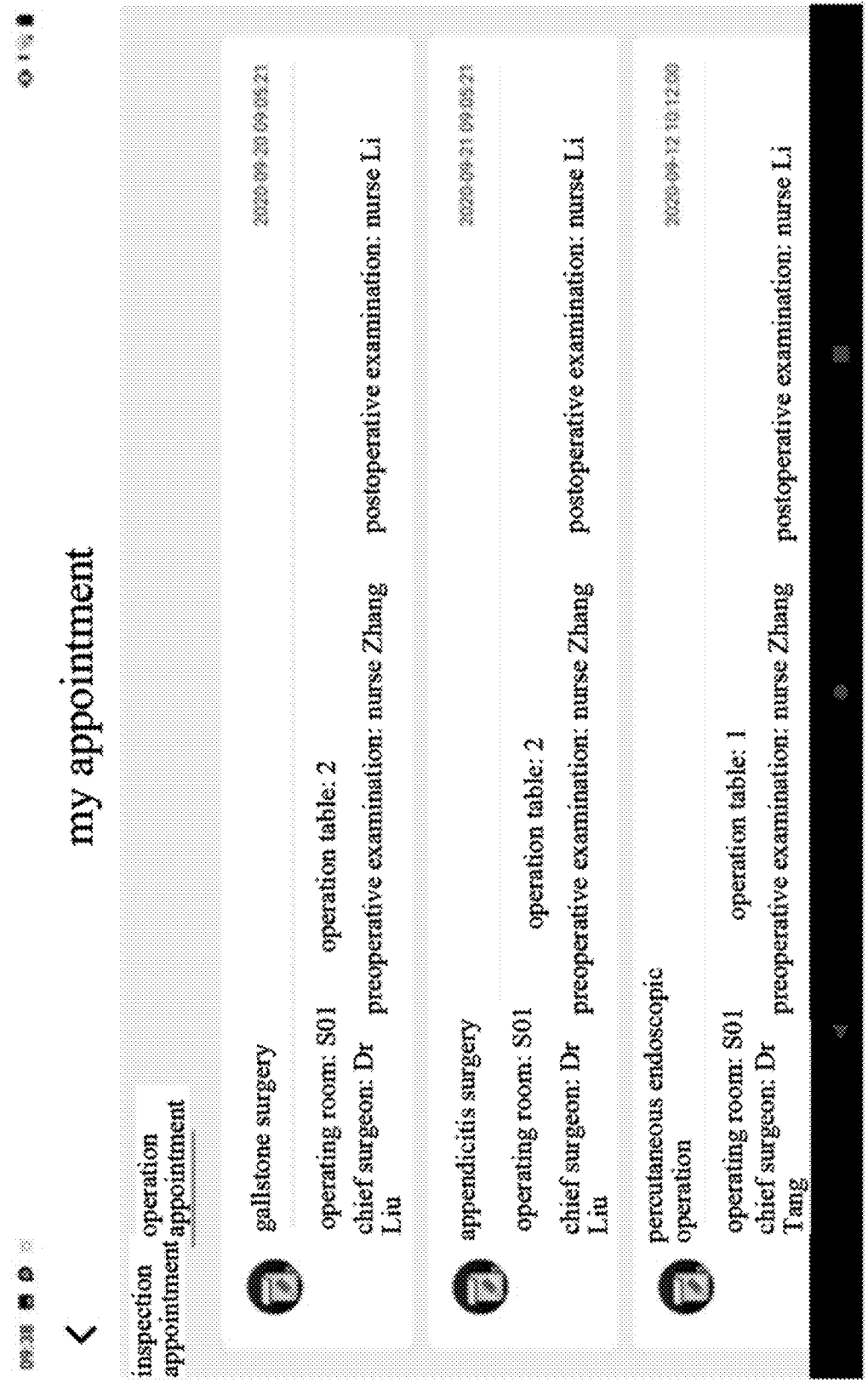
Figure 7H:
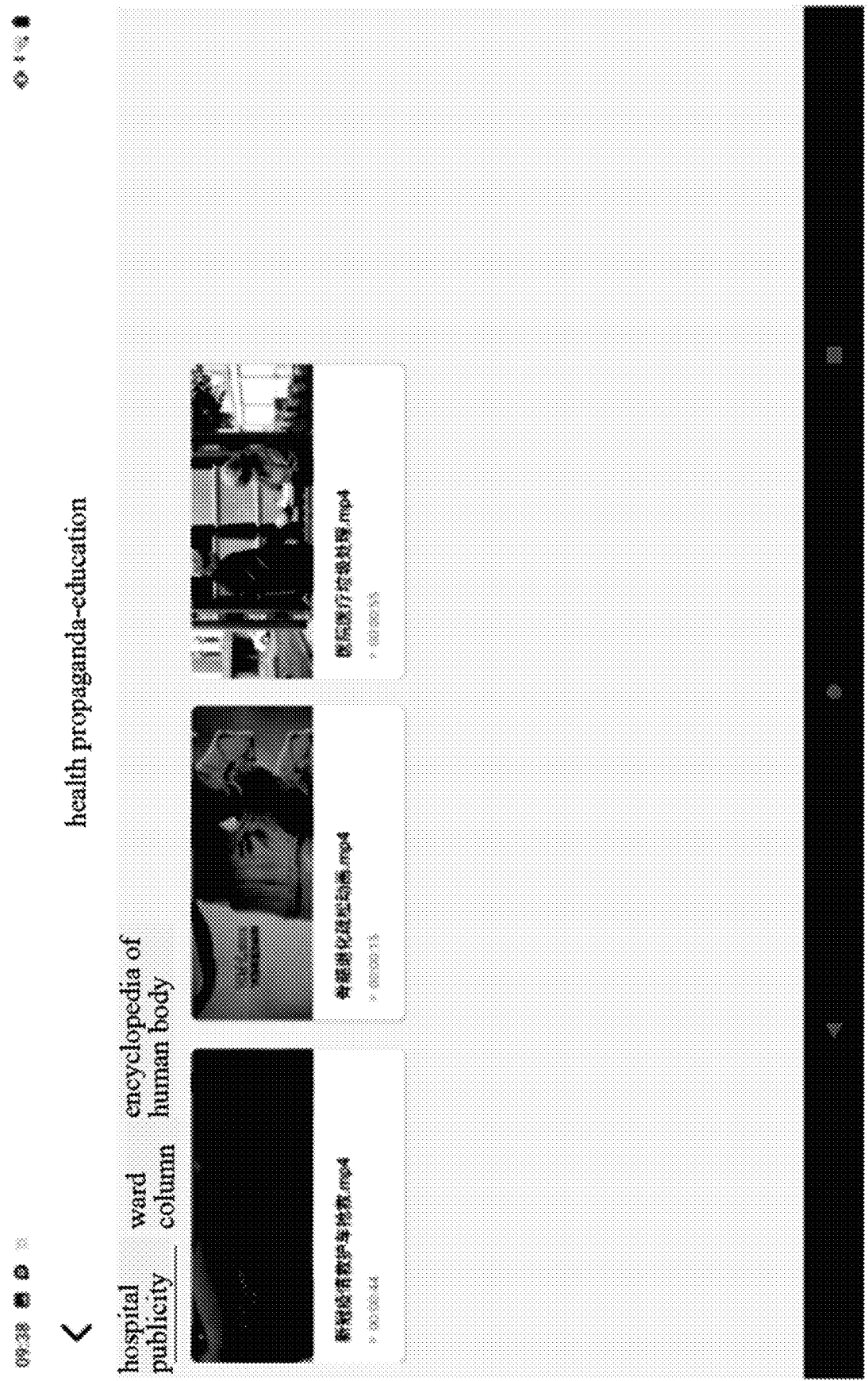
Figure 7I:
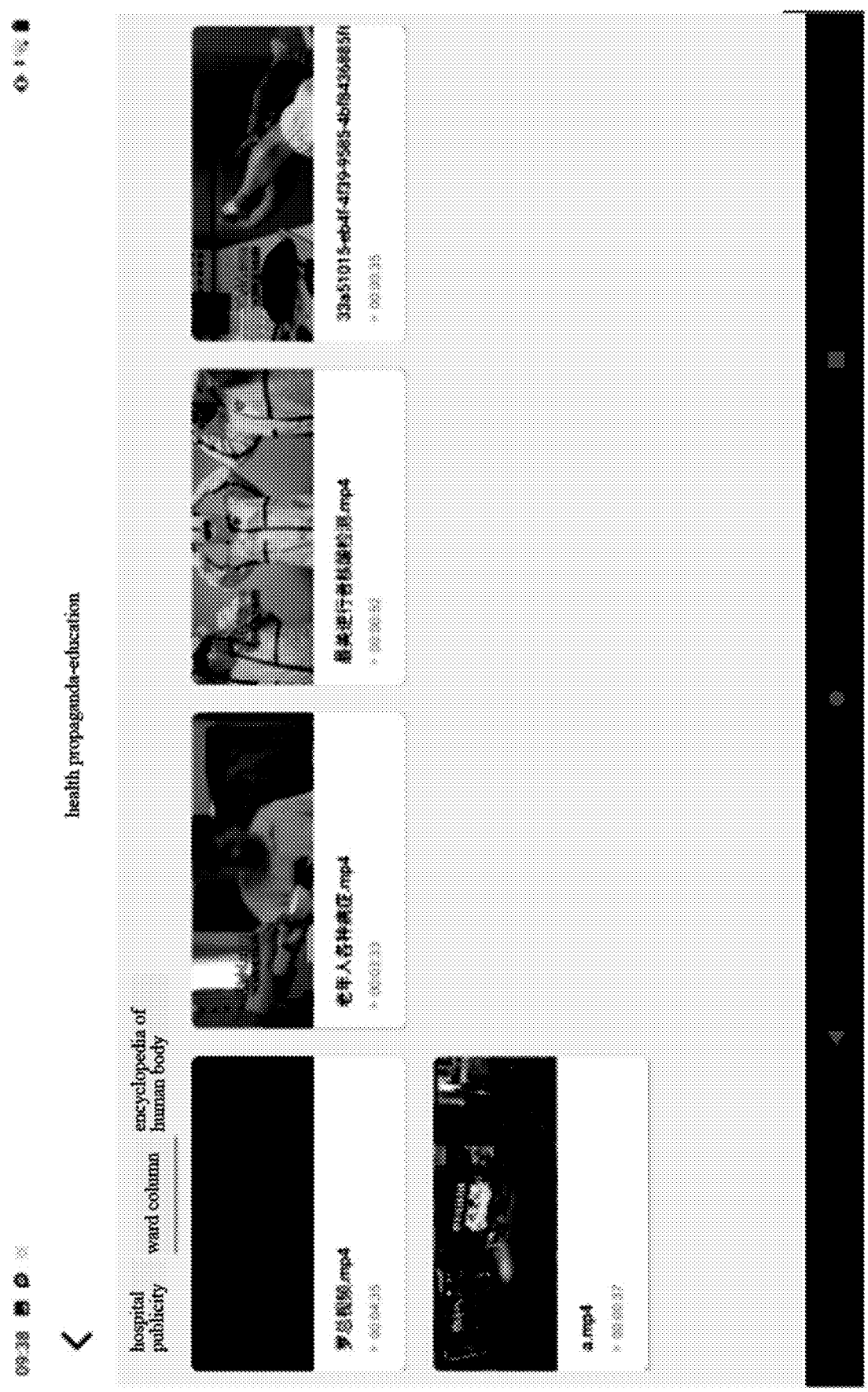
Figure 7J:
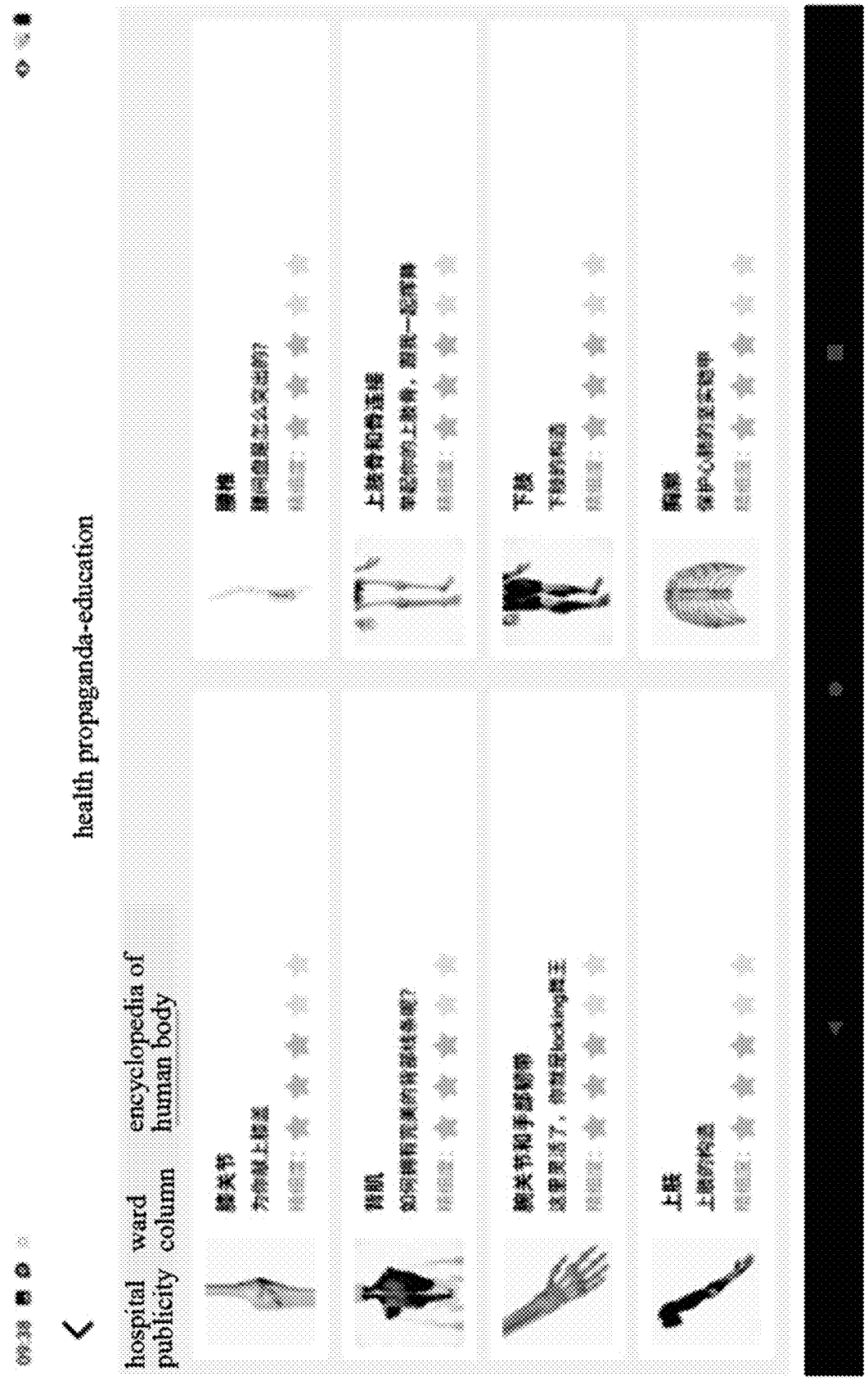
Figure 7K:
Figure 71:
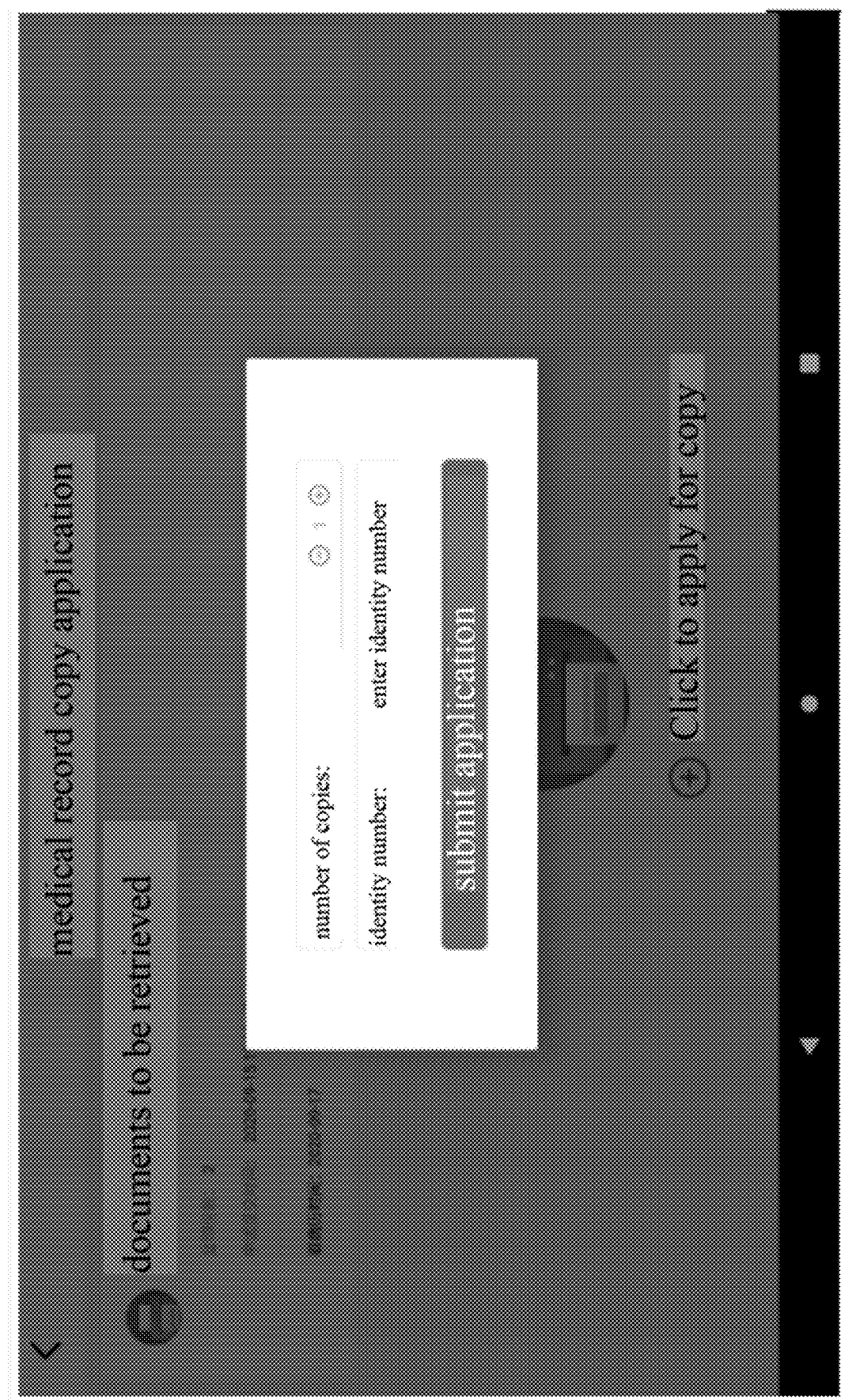
Figure 7O:
Figure 7P:
Figure 7Q:
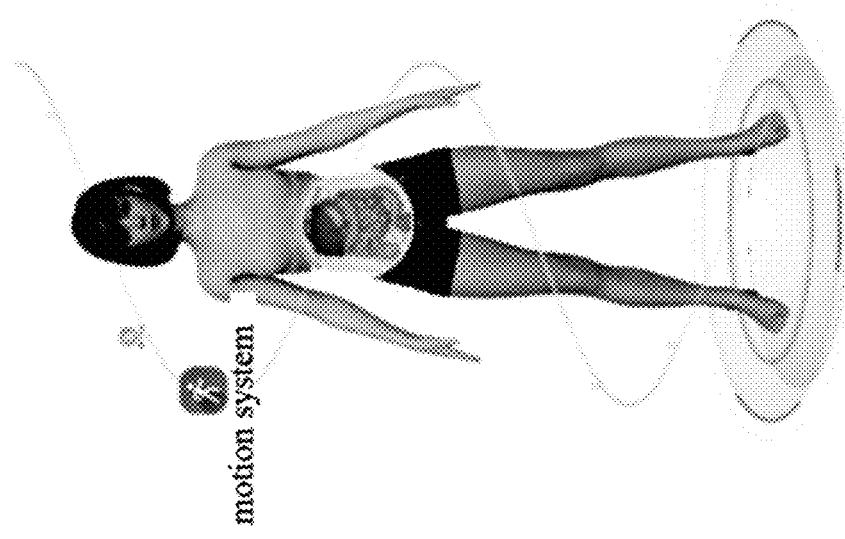
Figure 7R:
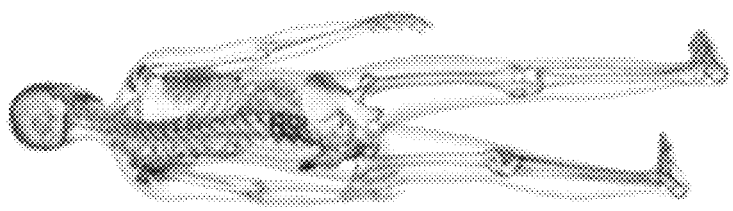
Figure 7S:
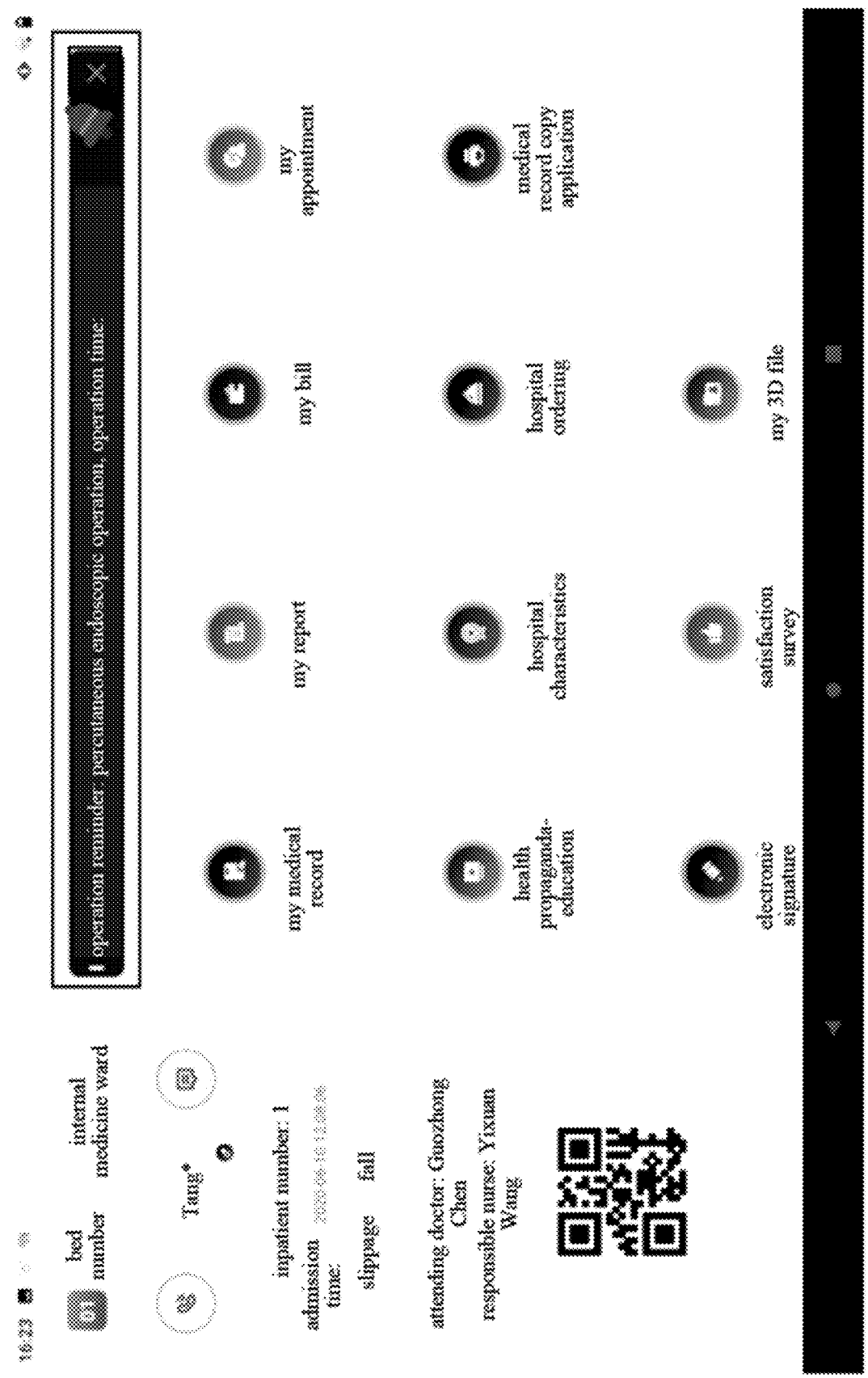

As shown in FIG. 7f to FIG. 7s, the first terminal further includes the following function control application scenarios.

For an appointment control, as shown in FIG. 7f to FIG. 7g, in response to a selection operation of the first user on the appointment control, the first terminal presents an appointment list of the first user. The appointment list includes an examination appointment and a surgery appointment.

For a propaganda-education control, as shown in FIG. 7h to FIG. 7j, in response to a selection operation of the first user on the propaganda-education control, the first terminal presents a propaganda-education list, including video, audio and text introductions of health education and hospital promotion.

For a medical record copy control, as shown in FIG. 7k to FIG. 7l, in response to a selection operation of the first user on the medical record copy control, the first terminal presents a medical record copy application form, including, for example, the number of copies of the application and identity authentication used to confirm an identity of an applicant.

For an electronic signature control, as shown in FIG. 7m to FIG. 7n, in response to a selection operation of the first user on the electronic signature control, the first terminal presents a signature list, such as a to-be-signed signature agreement and a signed signature agreement.

For a satisfaction survey control, as shown in FIG. 7o to FIG. 7p, in response to a selection operation of the first user on the satisfaction survey control, the first terminal presents a questionnaire, including survey information for doctors, nurses, and hospitals.

For a file control, as shown in FIG. 7q to FIG. 7r, in response to a selection operation of the first user on the file control, the first terminal presents corresponding user files including 3D files and motion systems of inpatients.

The first terminal further presents user information and reminder messages corresponding to the first identity identifier.

Specifically, as shown on the right side of FIG. 4b, the user information includes user name, gender, hospitalization information, medical staff information, and user's QR code information.

As shown in FIG. 7s, the reminder message is presented in the form of a pop-up message notification bar, which specifically includes an examination reminder, a surgical reminder, and a medical record receipt reminder.

In this embodiment, the first terminal can facilitate inpatients to receive information notifications from the hospital, conveniently and quickly inquire about personal information, recharge fees and obtain catering services, which can simplify the management of inpatients in the existing management system and effectively improve the user experience of inpatients, thereby remedying the problems in related technologies and having broad application prospects.

As the background management system of the first terminal and the second terminal, the server presents multiple interface components, including: authority management component, nursing information management component, hospital information management component, satisfaction survey component, device management component, medical record review management component and version management component.

FIG. 8a to FIG. 8j shows the server's authority management component.

Figure 8A:
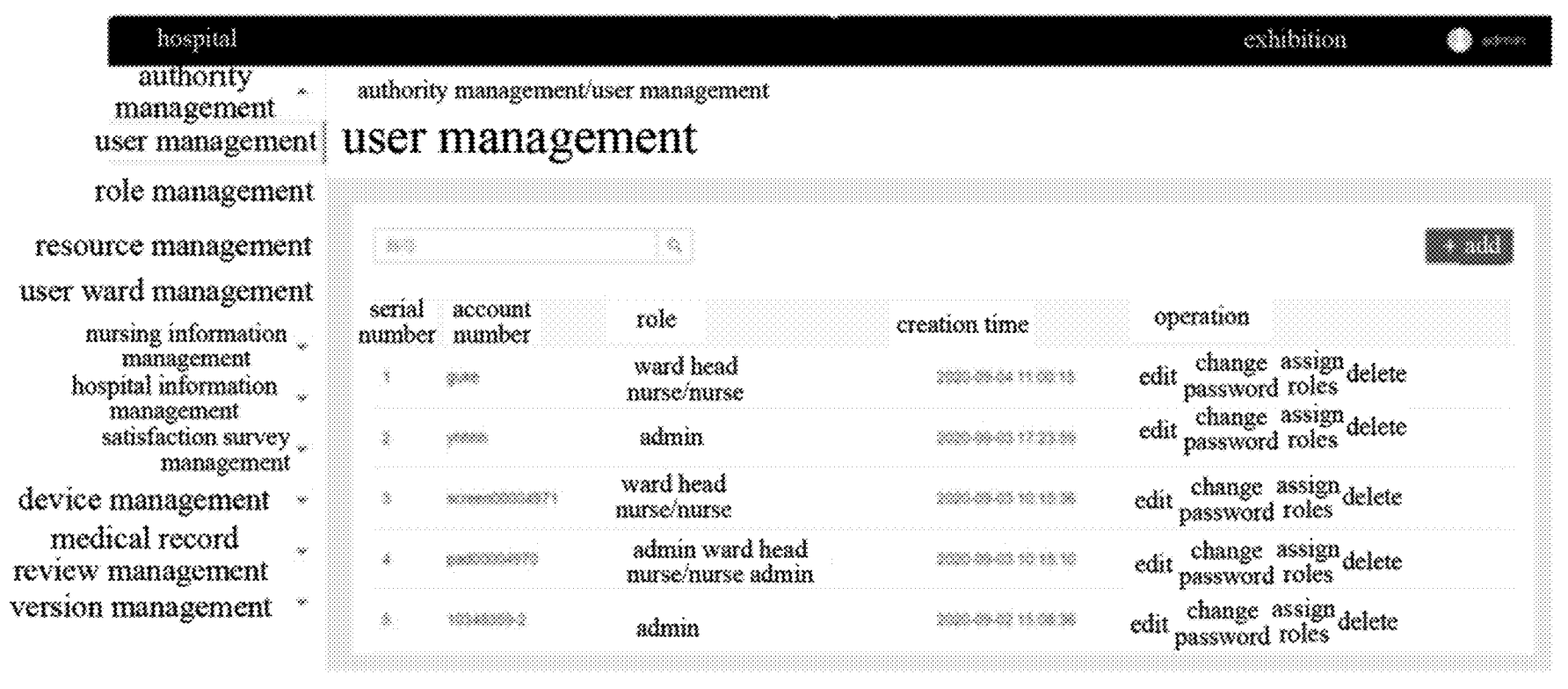

Specifically, as shown in FIG. 8a, the server presents a sub-interface "user management interface" of the authority management component, including interface information shown on the left, and a list of existing users, including user serial number, account number, role, creation time, and specific operations.

Figure 8B:
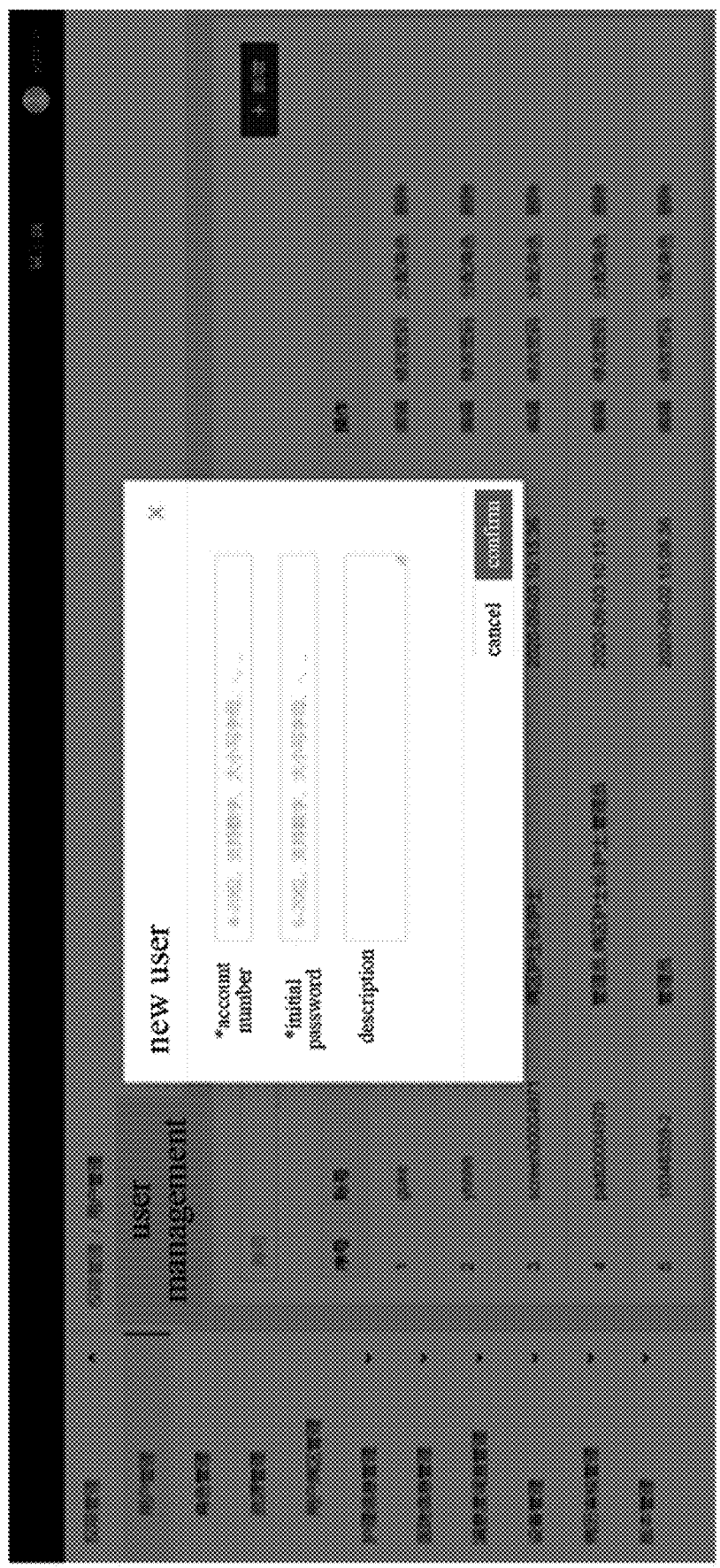

As shown in FIG. 8b, in response to the third user's operation of clicking on "Add", the server pops up an "add user" window, to prompt the third user to enter an account and an initial password to create a new user account. New users include administrators and ward nurses. The ward nurse is a second user who uses the second terminal. The second terminal is used as a display terminal to provide information to the medical staff. A user account and an initial password for the second terminal, can only be created by the third user administrator on the server. The second user logs in to the second terminal according to the established account, and uses interaction between the second terminal and the server to realize inquiries and operations on medical and nursing work.

After the third user establishes a second user account on the server, similar to the communication interaction between the first terminal and the server described above, the second user communicates and interacts with the server through the second terminal.

Figure 9A:
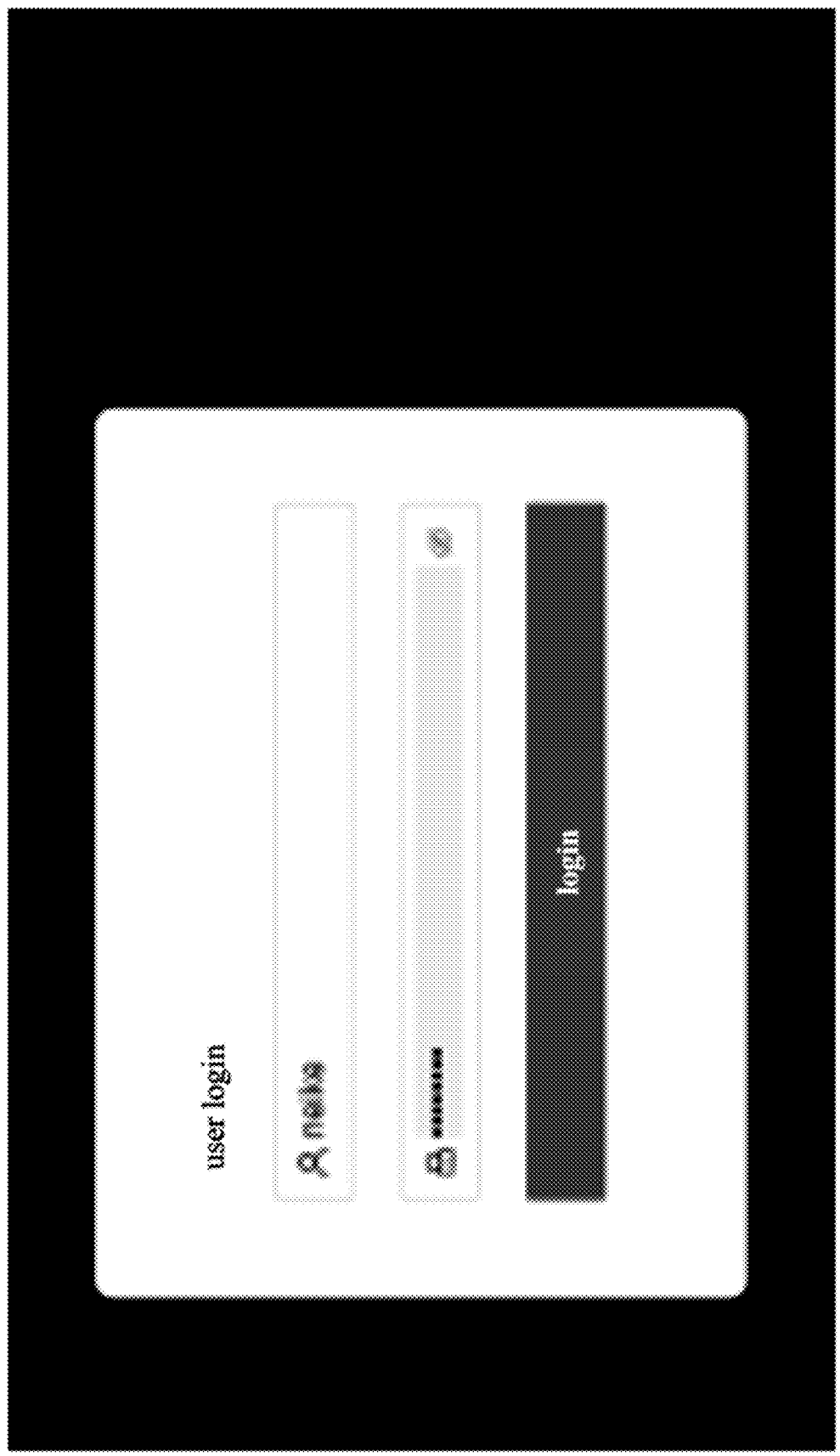
FIG. 9a to FIG. 9p are schematic diagrams showing menu controls of a second terminal according to an embodiment of the present application.

Specifically, firstly, as shown in FIG. 9a, the second terminal transmits a second login request to the server in response to a login operation of the second user, where the second login request includes a second identity identifier.

Figure 9B:
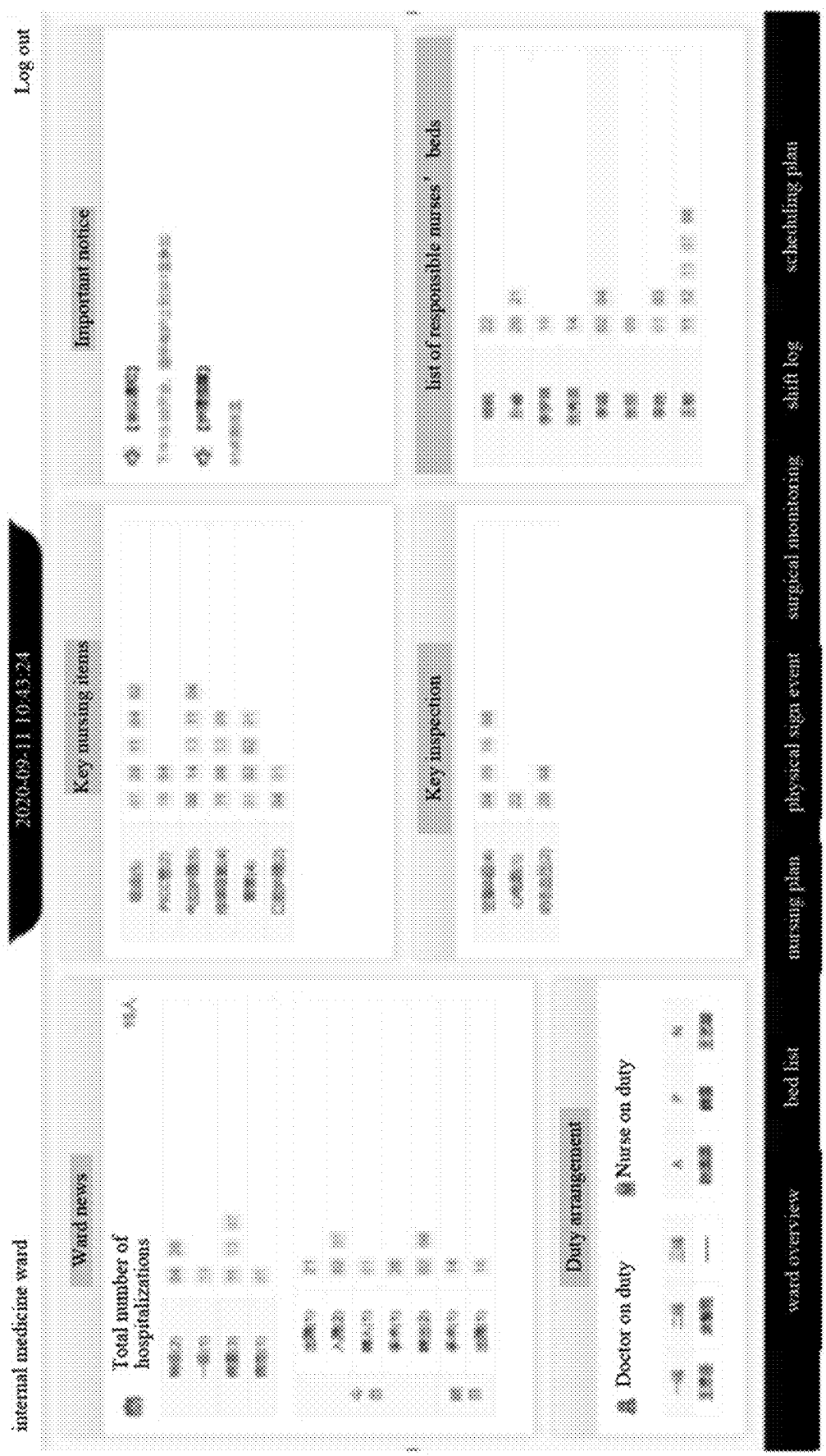

Secondly, as shown in FIG. 9b, the second terminal presents multiple menu controls corresponding to the second identity identifier.

The processor of the server receives the second login request, and identifies the second terminal as a display terminal applied to the nurse's station according to the second identity identifier in the second login request, and then transmits menu control information corresponding to the second identity identifier to the second terminal, such as menu controls displayed by the second terminal. The menu controls include a ward overview control, a bed list control, a nursing plan control, a physical sign event control, a surgical monitoring control, a shift log control, and a scheduling plan control.

Finally, the second terminal transmits a second function request to the server in response to the second user's selection operation of the menu controls, receives and presents function feedback information transmitted by the server. The second function request includes the second identity identifier.

Specifically, the server includes an MQTT message queue and a processor. The second terminal transmits a second function request to the MQTT message queue of the server in response to the second user's selection operation of the menu controls, and pushes the second function request to the processor of the server according to the second identity identifier in the second function request. The processor generates function feedback information according to the second function request and transmits the function feedback information to the MQTT message queue of the server. The MQTT message queue of the server pushes the function feedback information to the second terminal corresponding to the second identity identifier. The second terminal receives and presents the function feedback information transmitted by the server. The function feedback information is transmitted by the processor according to the received second function request, and is pushed to the second terminal corresponding to the second identity identifier via the MQTT message queue.

In this embodiment, the MQTT message queue determines a message pusher according to the second identity identifier, and pushes the function feedback information to the second terminal according to the second identity identifier. It is worth noting that based on the MQTT protocol, by categorizing the second terminals and setting message processing and push rules according to different topics and subscriptions, the present application can transmit a message to each second terminal and transmit a message to a designated second terminal. For example, second terminals disposed at nurse stations of different inpatient departments may be classified into an internal medicine device and a surgical device. In a case that a message directed to internal medicine nurse stations is pushed to the second terminals belonging to the internal medicine devices, and a message directed to surgical nurse stations is pushed to the second terminals belonging to the surgical devices. In other words, a message pushed to internal medicine devices, is only pushed to the second terminals grouped as internal medicine devices, and is not pushed to the second terminals grouped as surgical devices; and vice versa. Therefore, in this embodiment, different topics are set through the MQTT message queue, and each second terminal is grouped according to different grouping rules and set to subscribe to a topic of each corresponding group, thereby realizing group push of the MQTT message queue.

Based on the foregoing communication method, one embodiment of the present application provides a terminal, including a display module and a communication module. The display module includes a login control and a menu control. The login control is configured to transmit a second login request to the server and obtain multiple corresponding menu controls according to the second identity identifier of the terminal. The menu controls are configured to transmit a second function request to the server to receive and present function feedback information transmitted by the server. The second function request includes the second identity identifier. The communication module is configured to communicate with the server.

The terminal provided in this embodiment is a display terminal provided to the medical staff, such as a second terminal of a large display device arranged at a nurse station. Through interaction between the terminal and the server, the medical staff can inquire about an overall situation, individual situation, daily nursing needs and examination needs of inpatients, duty information and scheduling information, thereby simplifying the existing management system, effectively improving user experience of patients and the medical staff, and realizing information interaction, management and maintenance of smart wards, which has a wide range of application prospects. The specific implementation is the same as the foregoing embodiment, and will not be repeated here.

For the foregoing menu controls, details are described hereinafter.

Menu Control Application Scenario 1: Ward Overview Control.

As shown in FIG. 9b, in response to the second user's selection operation of the ward overview control, the second terminal presents bed information of a ward where the second user is located and corresponding patient controls, including ward dynamics, on-duty arrangement, key nursing items, key examination items, important notices and a list of responsible nurses' beds.

The ward dynamics include: a total number of inpatients, nursing grade distribution, dynamics of leaving and entering the hospital today, dynamics of leaving and entering the hospital tomorrow. The key nursing items include a list of nursing items. The key examination items include a list of examination items. The list of responsible nurses' beds includes a list of responsible nurses. A bed number of a corresponding inpatient is displayed after each item name. A nursing level of the inpatient is represented by a color of the bed number. The on-duty arrangement shows specific arrangements of doctors on duty, nurses on duty and medical staff on duty today. The important notices include meeting notices and nursing reminders to remind the medical staff at the nurse station using the second terminal.

Menu Control Application Scenario 2: Bed List Control.

As shown in FIG. 9c, in response to the second user's selection of the "bed list control", the second terminal displays all beds in a local ward and information of an inpatient corresponding to each bed, including the inpatient's bed number, ward name, the inpatient's name, gender, hospitalization number, hospitalization time, attending doctor, responsible nurse and other information. Only the bed number is displayed for beds without patients.

Figure 9D:
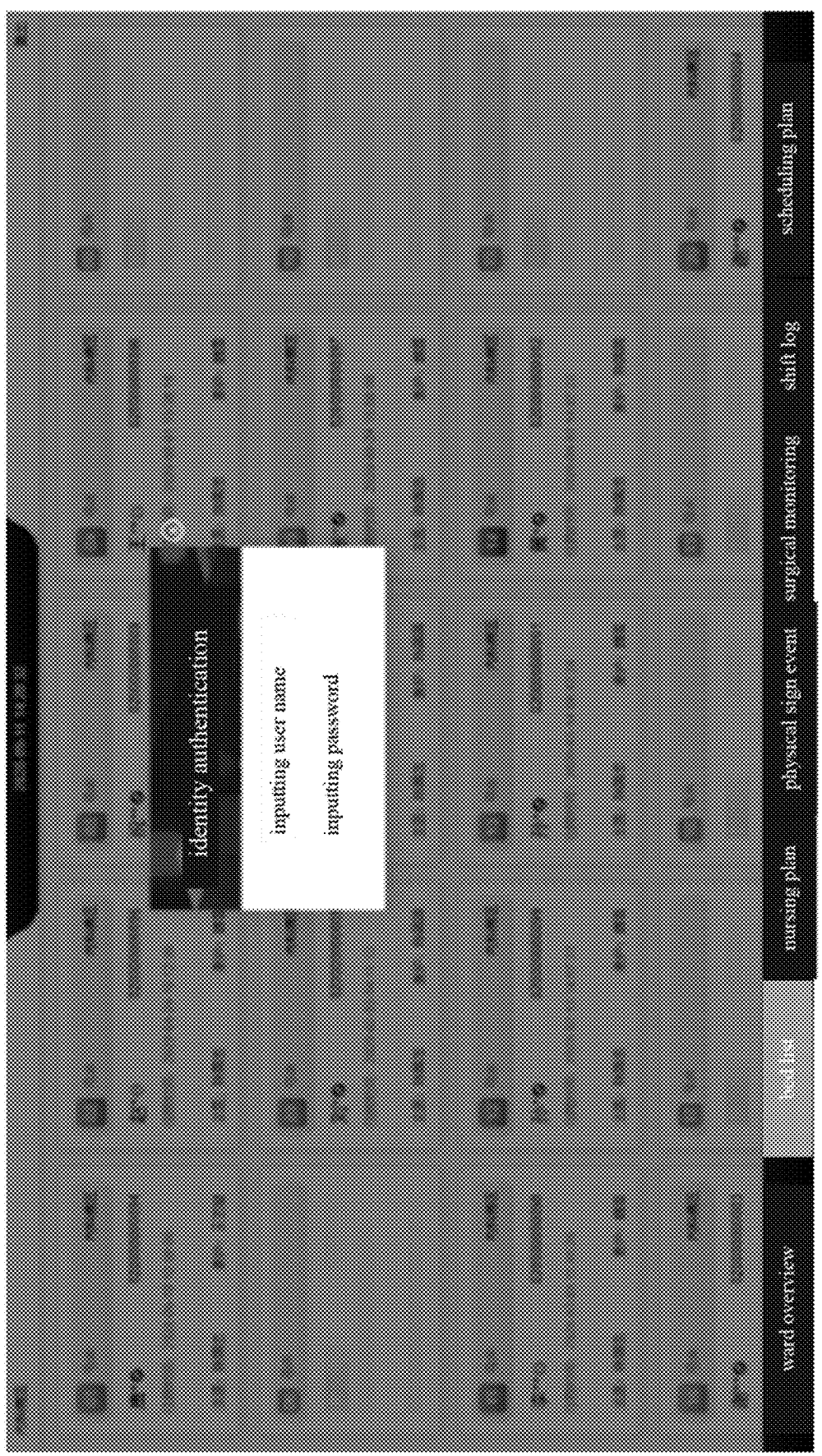
Figure 9F:
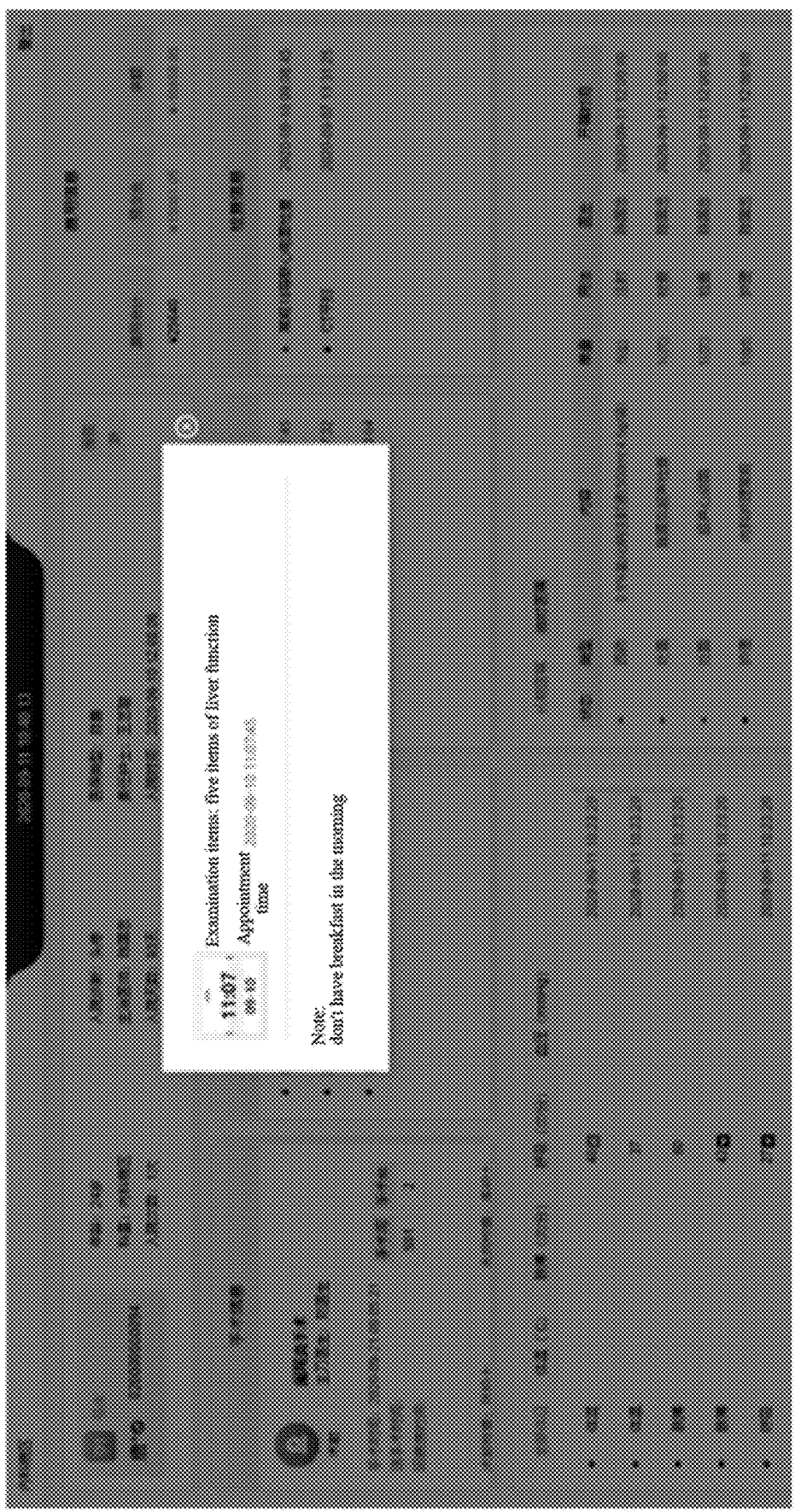
Figure 9G:
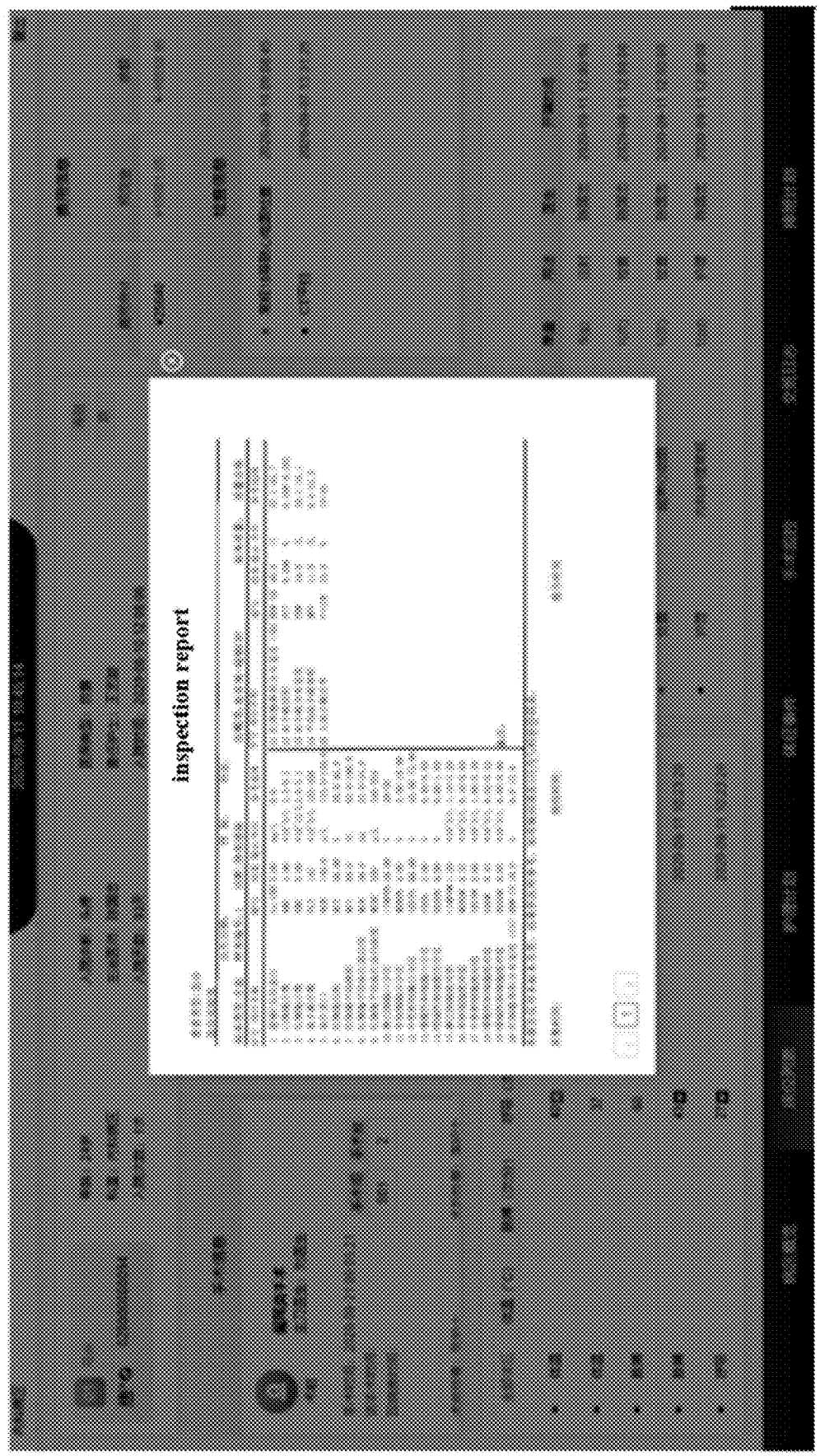
Figure 9H:
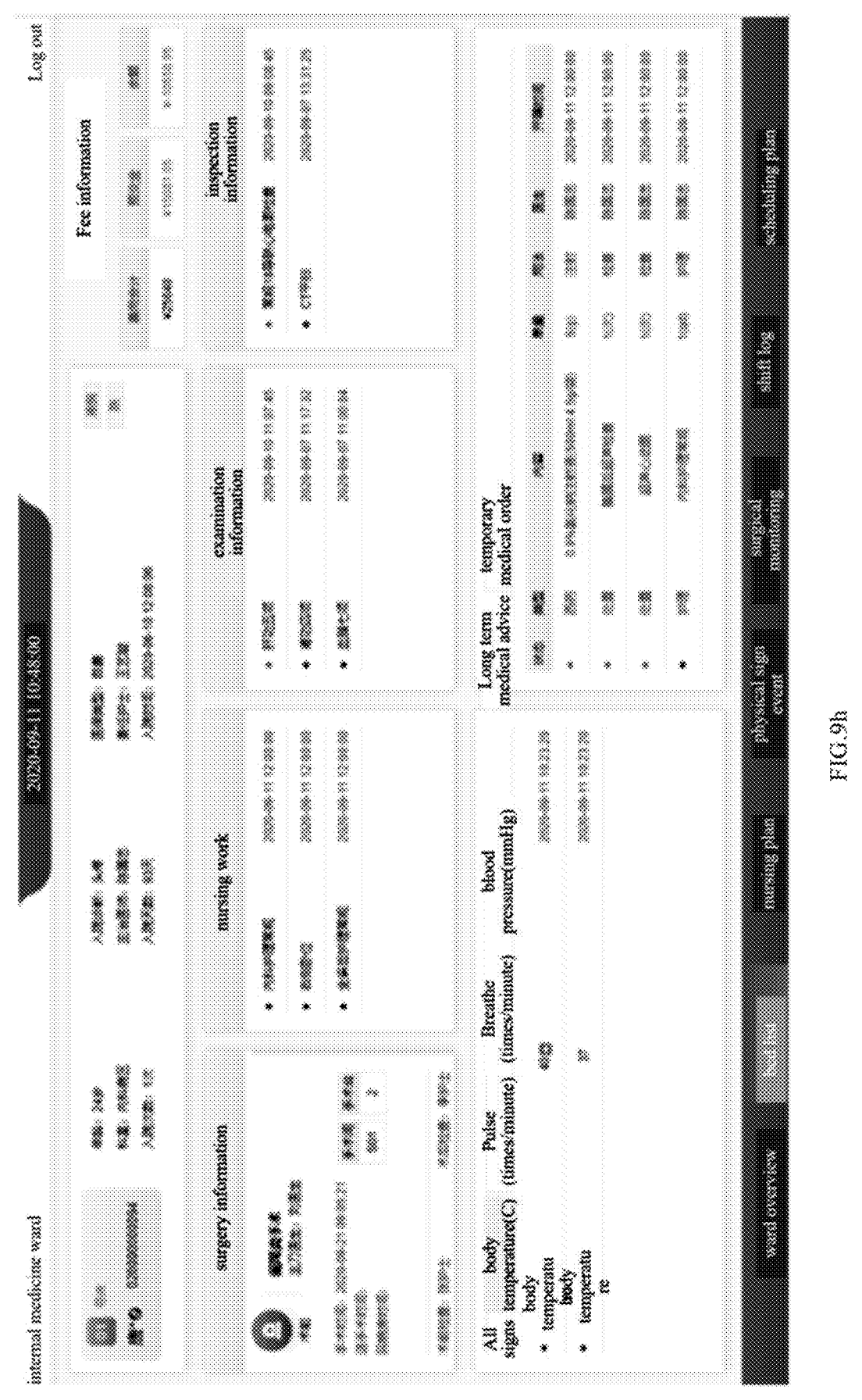
Figure 9I:
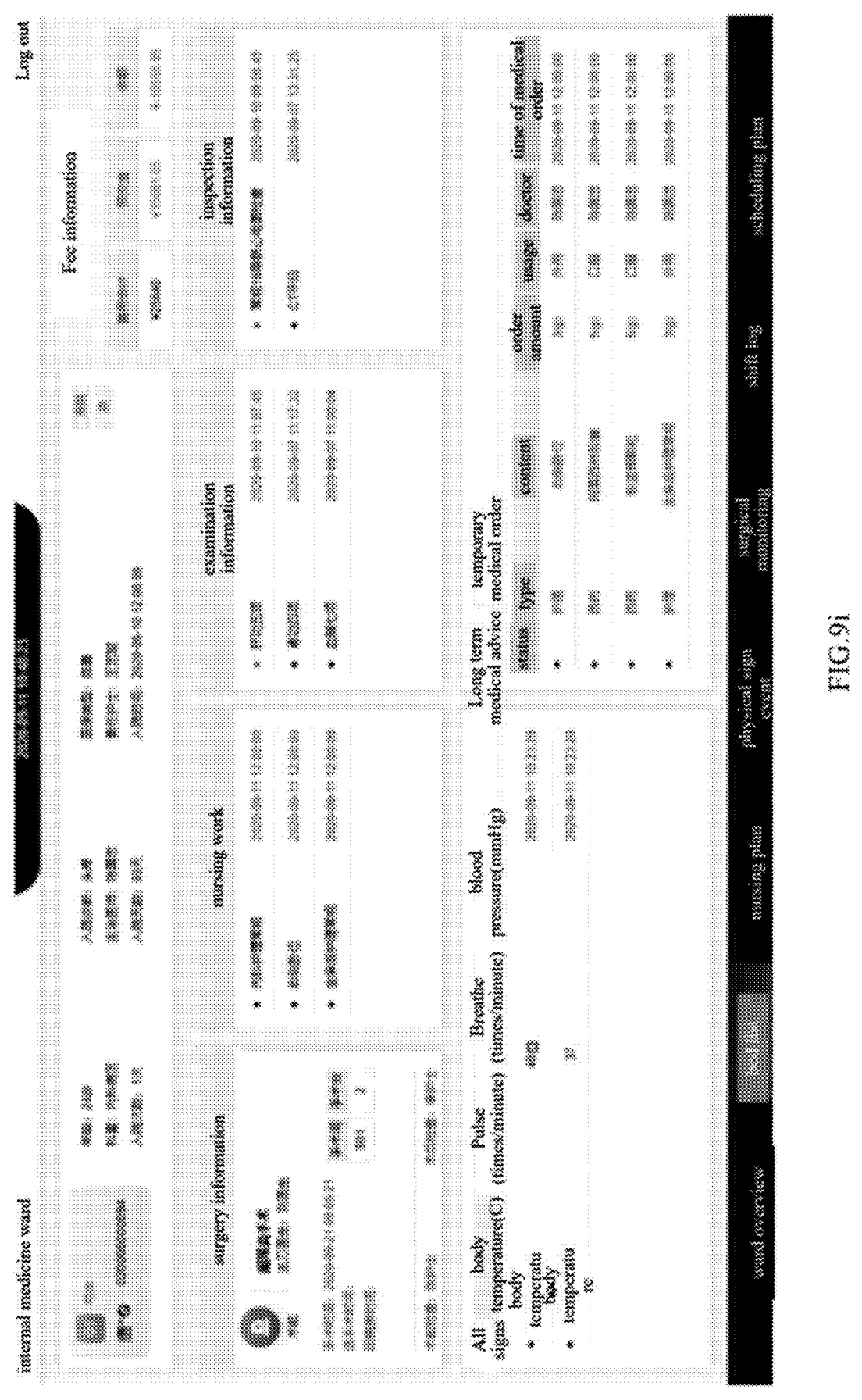

Specifically, as shown in FIG. 9d, in response to the second user's selection of patient controls, the second terminal presents identity authentication, including inputting user name and password of the medical staff to view specific information of a selected inpatient. Further, as shown in FIG. 9e, in response to the second user's authentication operation of the identity authentication, the second terminal presents user information, fee information, surgery information, nursing work information, examination information, inspection information, physical sign information and medical order information of a corresponding patient. Further, the inspection information has two states: incomplete or completed. By clicking on an incomplete inspection item, as shown in FIG. 9f, inspection item information is displayed, including: item name, appointment time, and points for attention. By clicking on a complete inspection item, as shown in FIG. 9g, specific inspection report information is displayed. Further, as shown in FIG. 9h, the physical sign information includes all data, such as body temperature data, pulse data, respiration data, or blood pressure data that can be switched to display. As shown in FIG. 9i, the medical order information includes completion status of incomplete or completed, type, content, order amount, usage, doctor, and time of the medical order. A long-term medical order data is displayed by default, and it can be switched to temporary medical order data as required.

The following menu control application scenarios are further included.

Figure 9J:

As shown in FIG. 9j, in response to the second user's selection operation of the nursing plan control, the second terminal presents nursing plan information of the ward where the second user is located. The nursing plan information includes today's physical sign measurement information, today's risk assessment information, today's nursing item information, and today's medical order information.

Figure 9K:
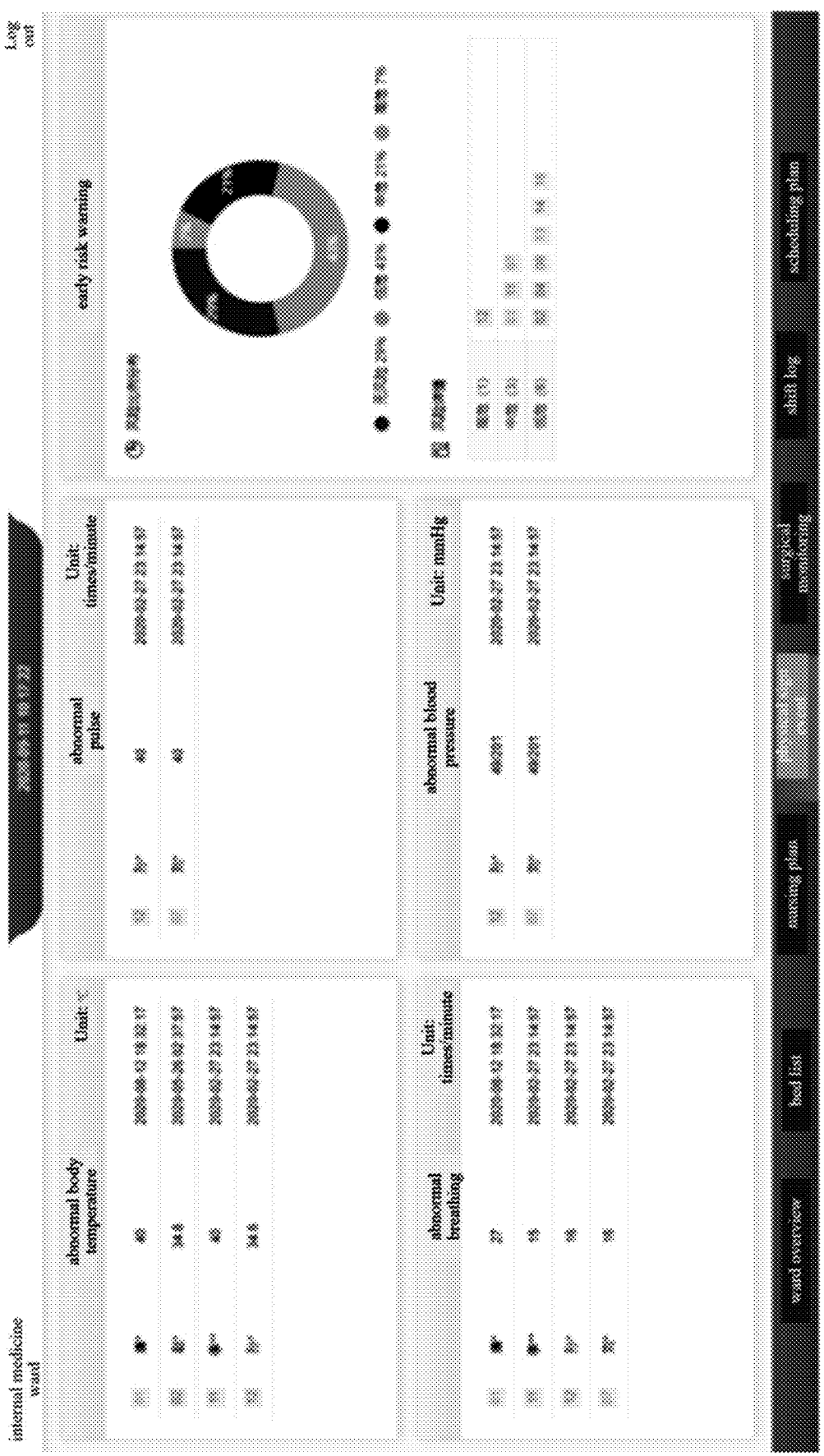

As shown in FIG. 9k, in response to the second user's selection operation of the physical sign event control, the second terminal presents physical sign event information of the ward where the second user is located. The physical sign event information includes abnormal body temperature data information, abnormal pulse data information, abnormal breathing data information, abnormal blood pressure data information and early risk warning information.

As shown in FIG. 9l, in response to the second user's selection operation of the surgical monitoring control, the second terminal presents surgical monitoring information of the ward where the second user is located. The surgical monitoring information includes patient information, medical information and status information corresponding to each surgery, specifically including surgery status, bed number, name, surgery name, operating room, operating table, operating time, surgeon doctor, delivery time, preoperative check nurses, time to return to the ward, and postoperative check nurse. Meanwhile, as shown in FIG. 9m, operation lists of different dates can be switched by an operation on this interface.

Figure 9N:
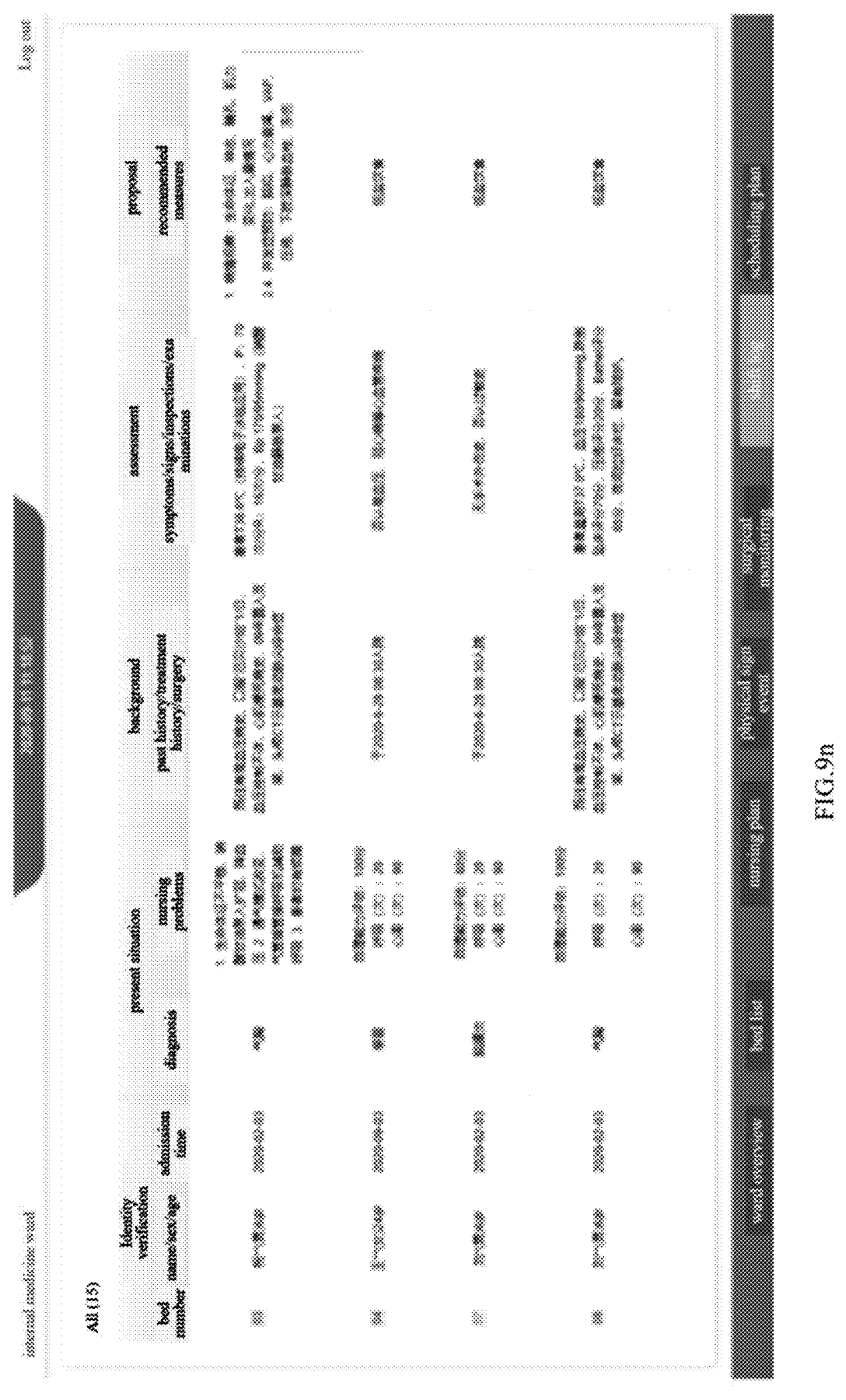

As shown in FIG. 9n, in response to the second user's selection operation of the shift log control, the second terminal presents shift log information of the ward where the second user is located. The shift log information includes nursing information of each patient in the ward where the second user is located, specifically including bed number, name/sex/age, admission time, diagnosis, nursing problems, past hi story/treatment hi story/surgery, symptoms/signs/inspections/examinations, recommended measures.

Figure 9O:
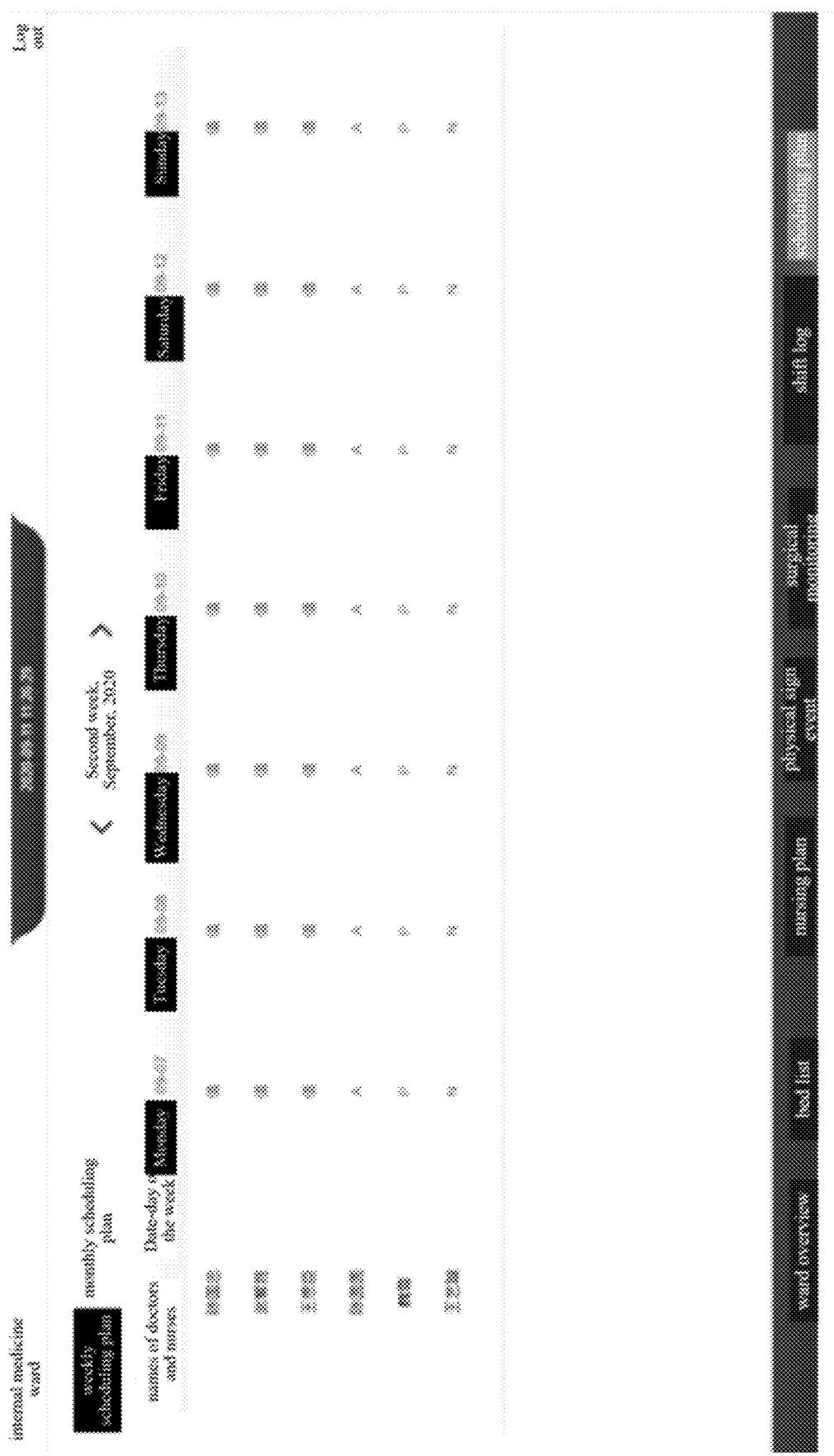
Figure 9P:
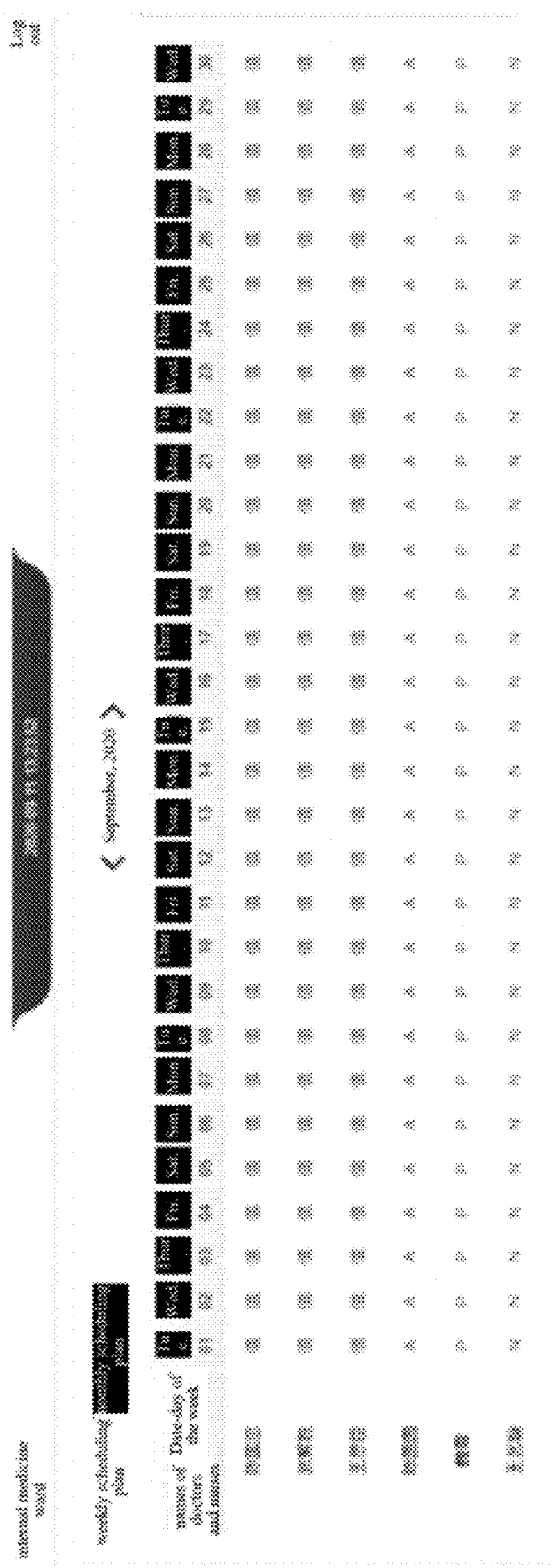

As shown in FIG. 9o, in response to the second user's selection operation of the scheduling plan control, the second terminal presents scheduling plan information of the ward where the second user is located. The scheduling plan information includes schedule information of each medical staff in the ward where the second user is located. As shown in FIG. 9p, the second terminal may switch to a monthly scheduling plan list, so that plans for a previous month and a next month can be switched by a switch button.

In this embodiment, the second terminal can facilitate the medical staff of the nurse station to query ward information, specific patient conditions, daily work priorities and precautions, and can also receive information notifications from the hospital, thereby simplifying work management and work arrangement of the medical staff in the inpatient department in the existing management system, effectively improving the work efficiency of the medical staff, then remedying the problems in the related art and having a wide range of application prospects.

Figure 8C:
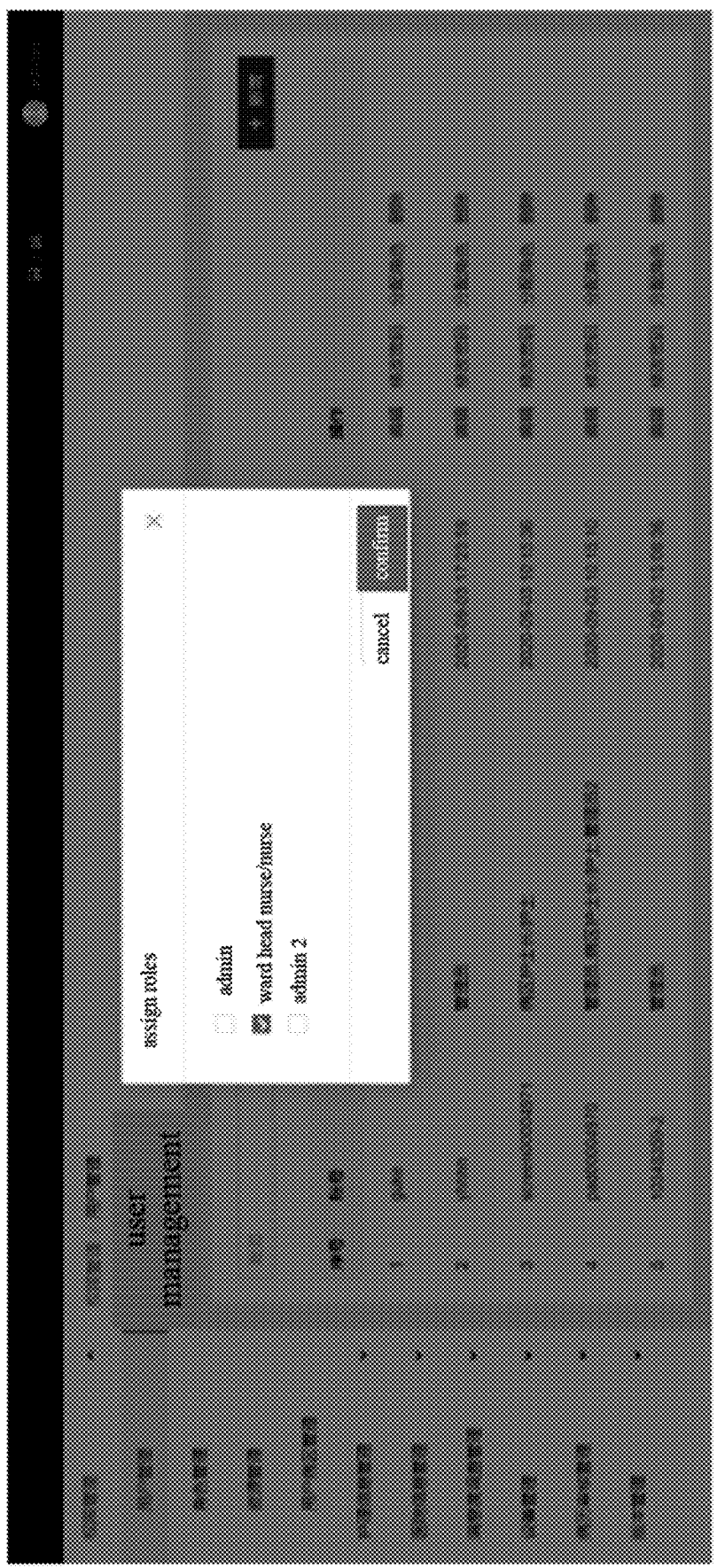

Further, as shown in FIG. 8c, in response to the third user's operation of clicking on "assign role", the server pops up an "assign role" window, to prompt the third user to select a role identity for a newly created account.

Figure 8D:
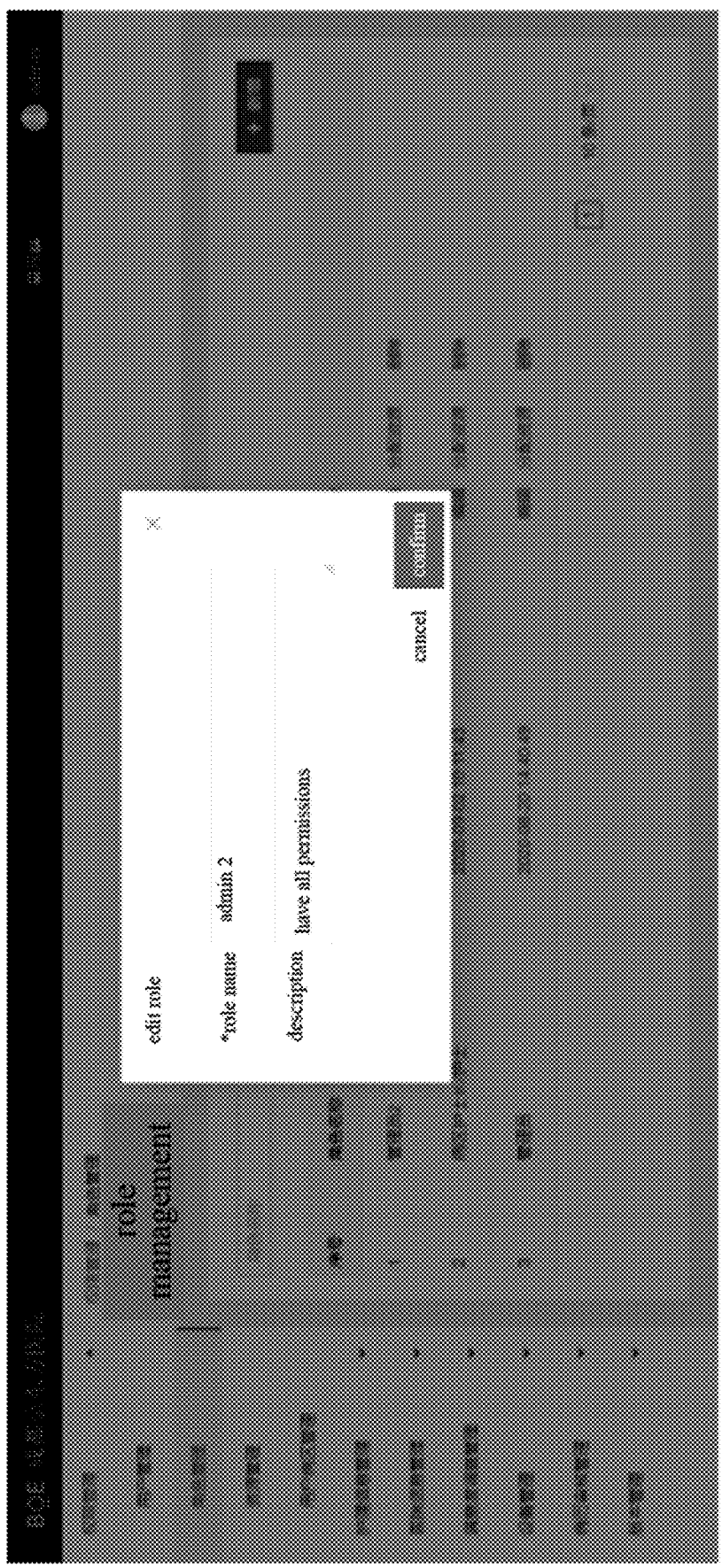

As shown in FIG. 8d, in response to the third user's operation of clicking on "edit", the server pops up an "edit role" window, to prompt the third user to enter an account and edit the role.

Figure 8E:

As shown in FIG. 8e, in response to the third user's operation of clicking on "allocate resource", the server presents an "allocate resource" interface, to prompt the third user to allocate resources for a selected account, such as assigning resources such as authority management, device management, nursing information and hospital information management to the selected account.

Figure 8F:
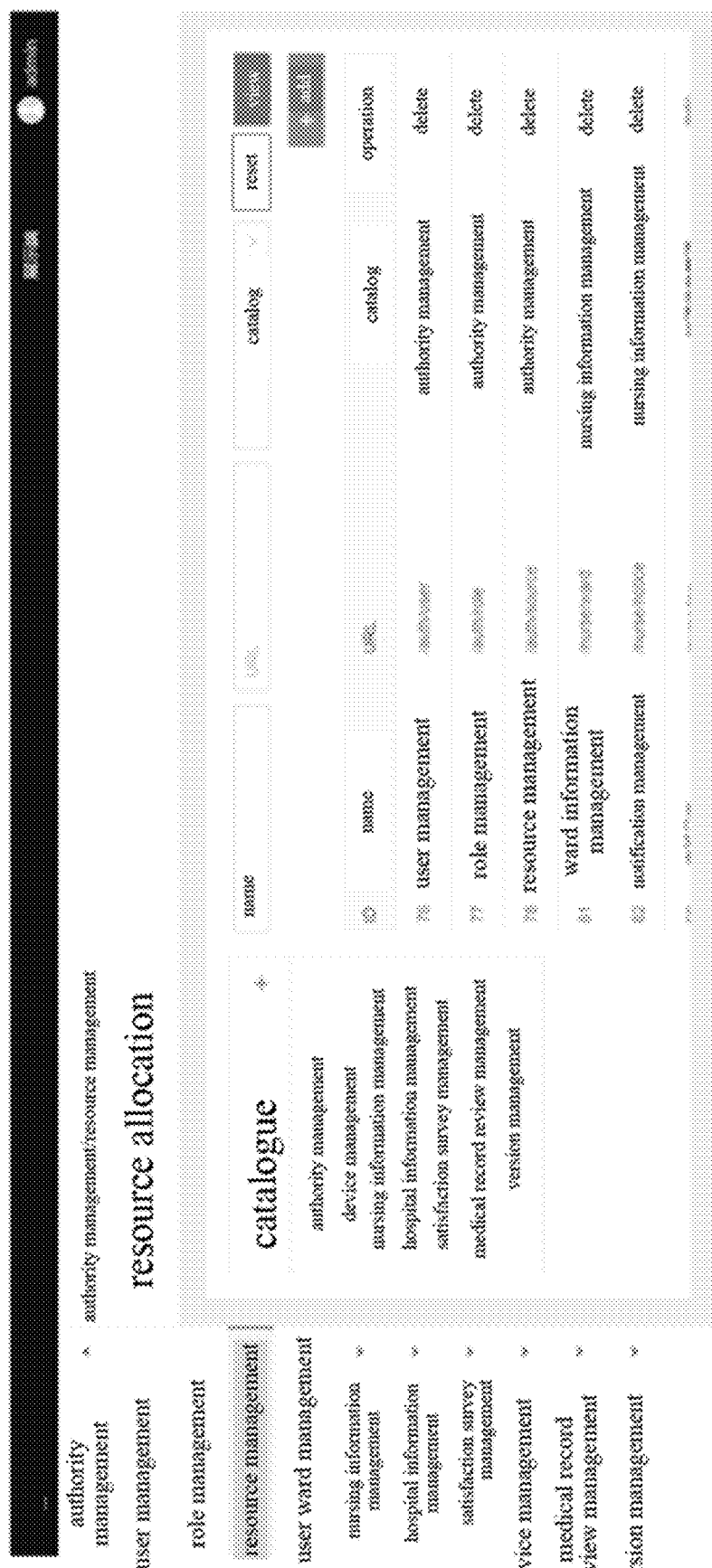
Figure 8G:
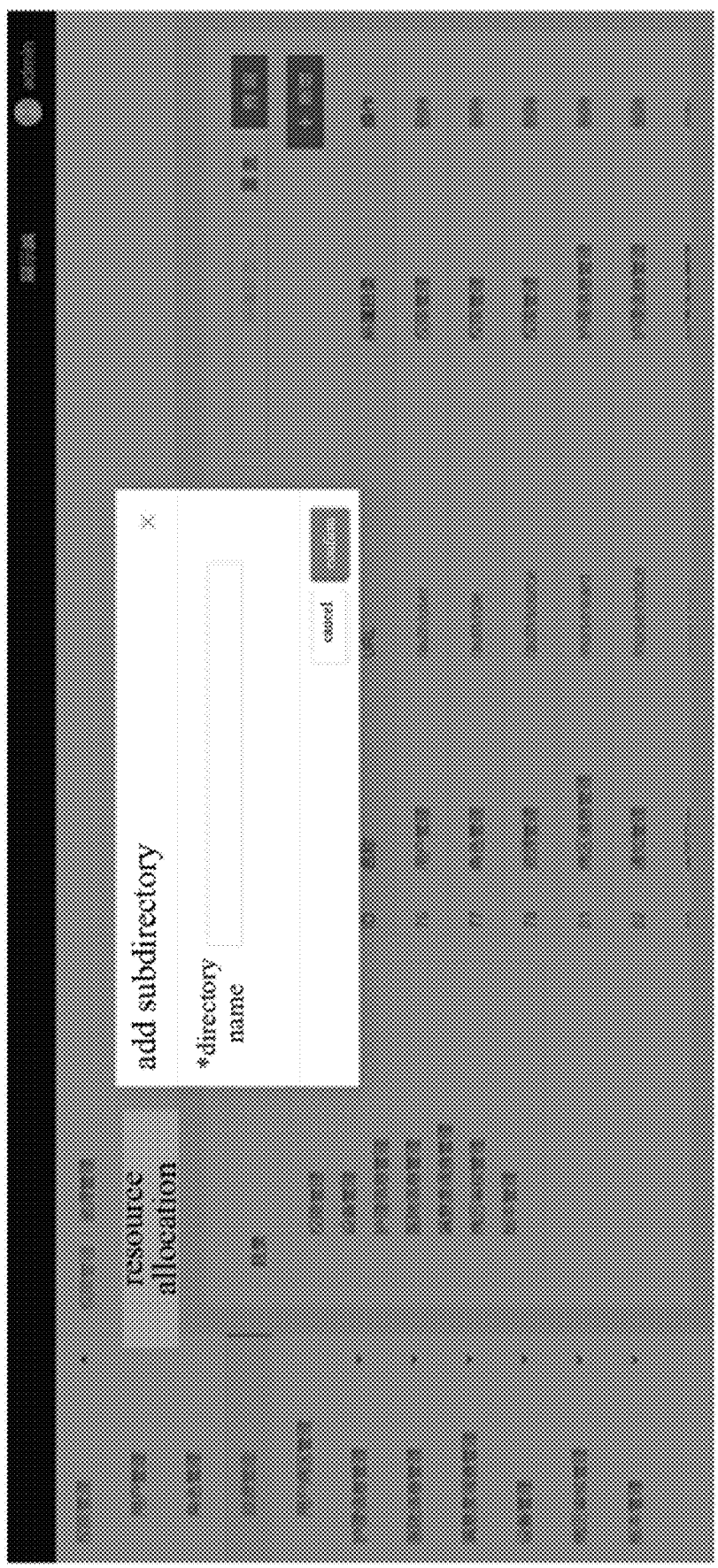
Figure 8H:
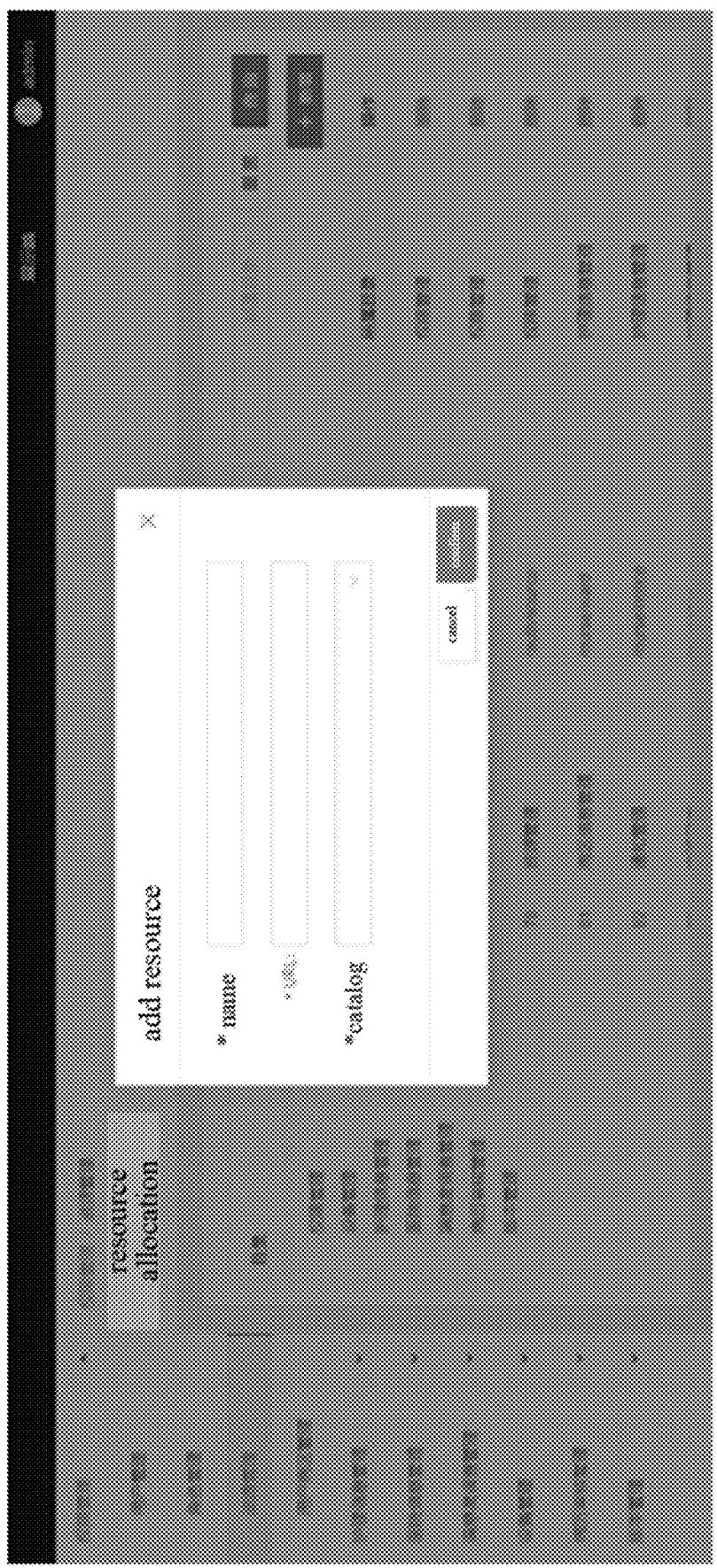

As shown in FIG. 8f, in response to the third user's operation of clicking on "resource management", the server presents a "resource management" interface, to display a list of resources, including directory management, adding, and deleting operations. The directory management includes: displaying new sub-directories, editing, and deleting buttons. As shown in FIG. 8g, an "add new sub-directory" operation is implemented at the resource management interface. As shown in FIG. 8h, an "add new resource" operation is implemented at the resource management interface.

Figure 8I:
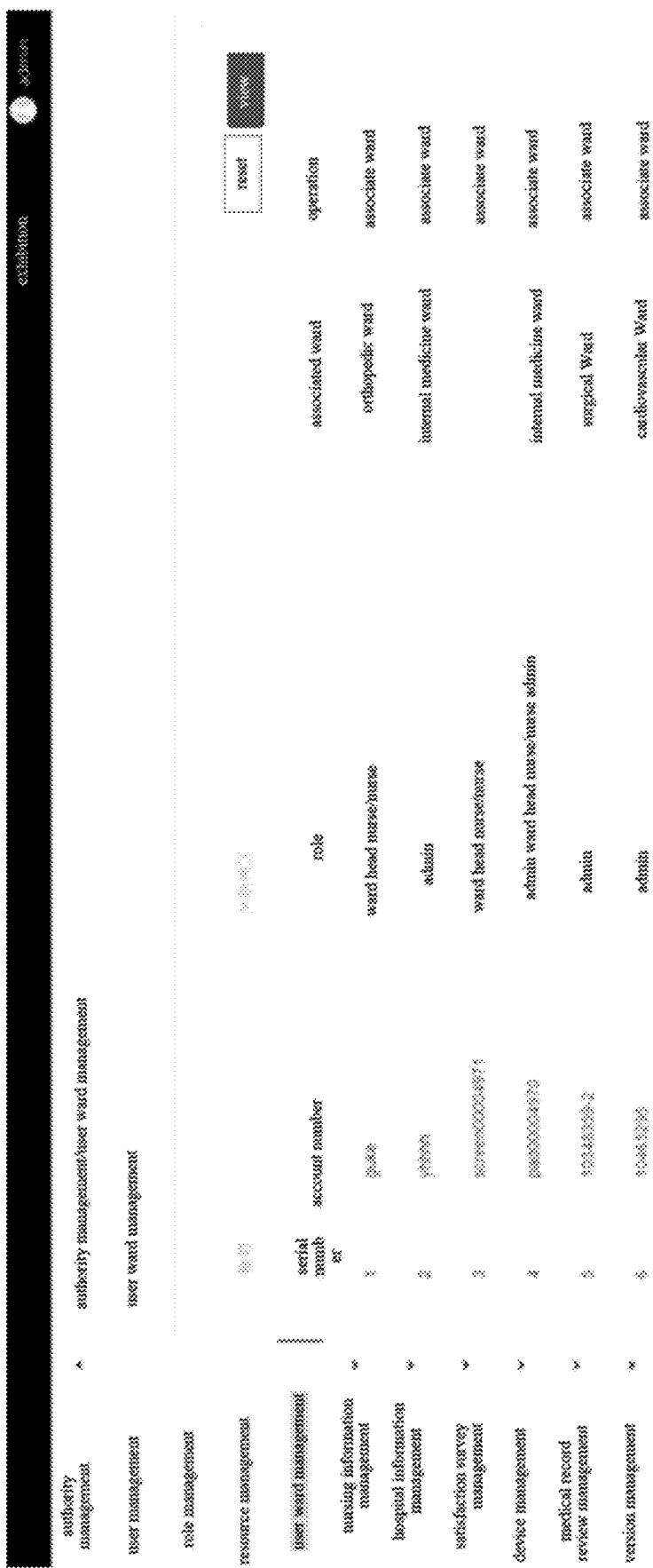
Figure 8J:
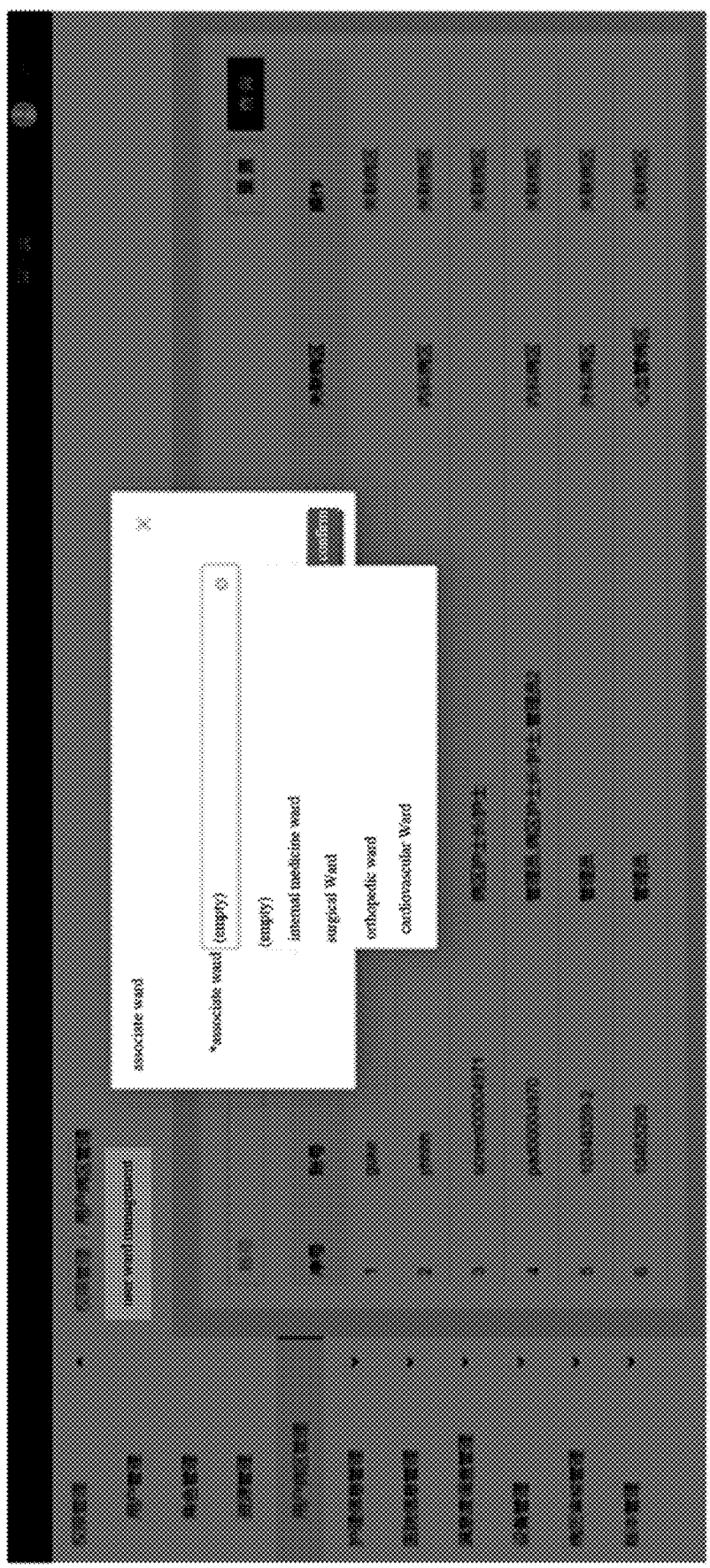

As shown in FIG. 8i, the authority management of the server further includes user ward management, which presents a list of user wards, including accounts, roles, and associated wards. By clicking on a managed ward, as shown in FIG. 8j, permissions of wards corresponding to a user may be associated or modified.

As shown in FIG. 10a to FIG. 10d, the server further includes a nursing information management component, which specifically includes: ward information management, notification management, and shift log.

Figure 10A:
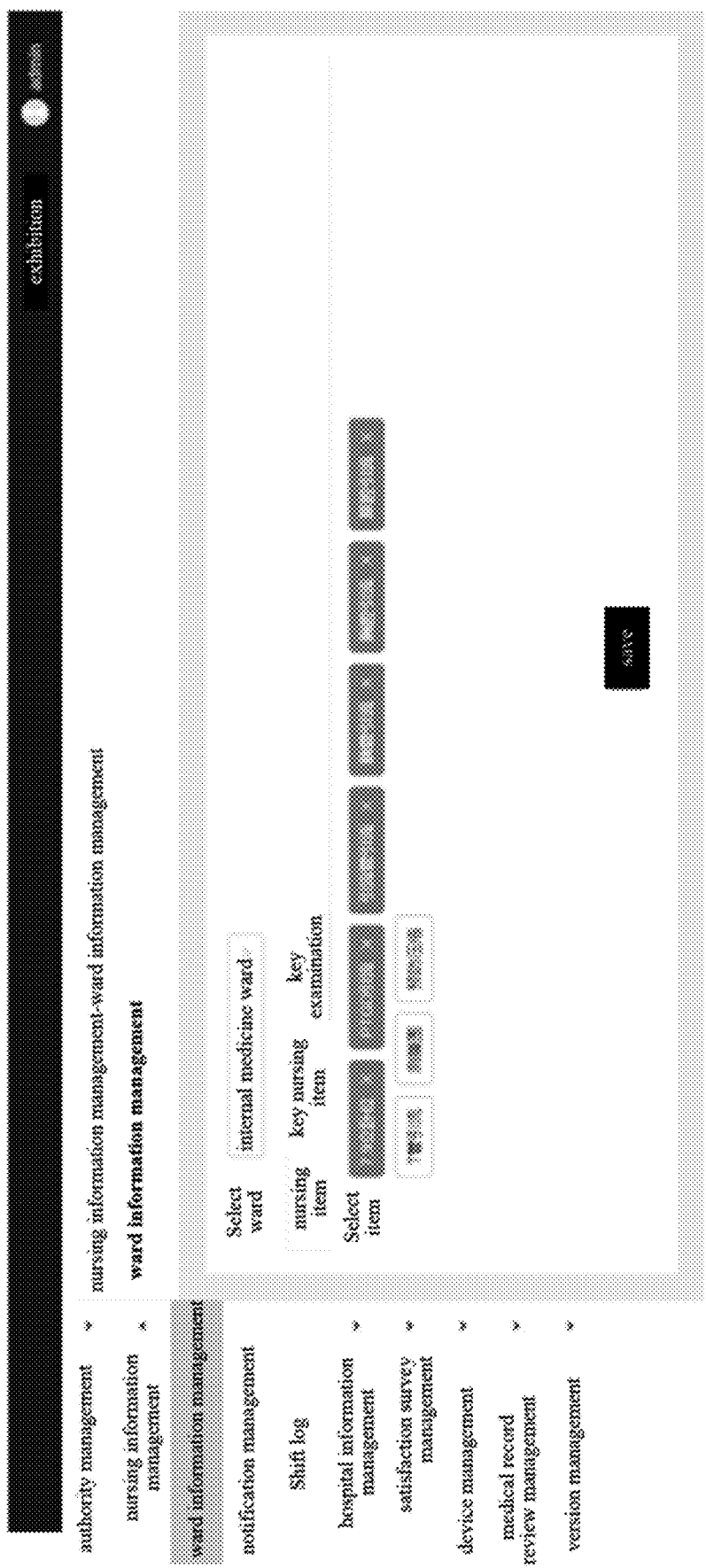
FIG. 10a to FIG. 10r are schematic diagrams showing various interface components of a server according to an embodiment of the present application.

As shown in FIG. 10a, in response to the third user's operation of clicking on "nursing information management-ward information management", the server presents a ward information management page for setting nursing items, key nursing items, and key examinations. Each nursing item includes a sub-list of items so that the third user can set according to actual needs.

Figure 10B:
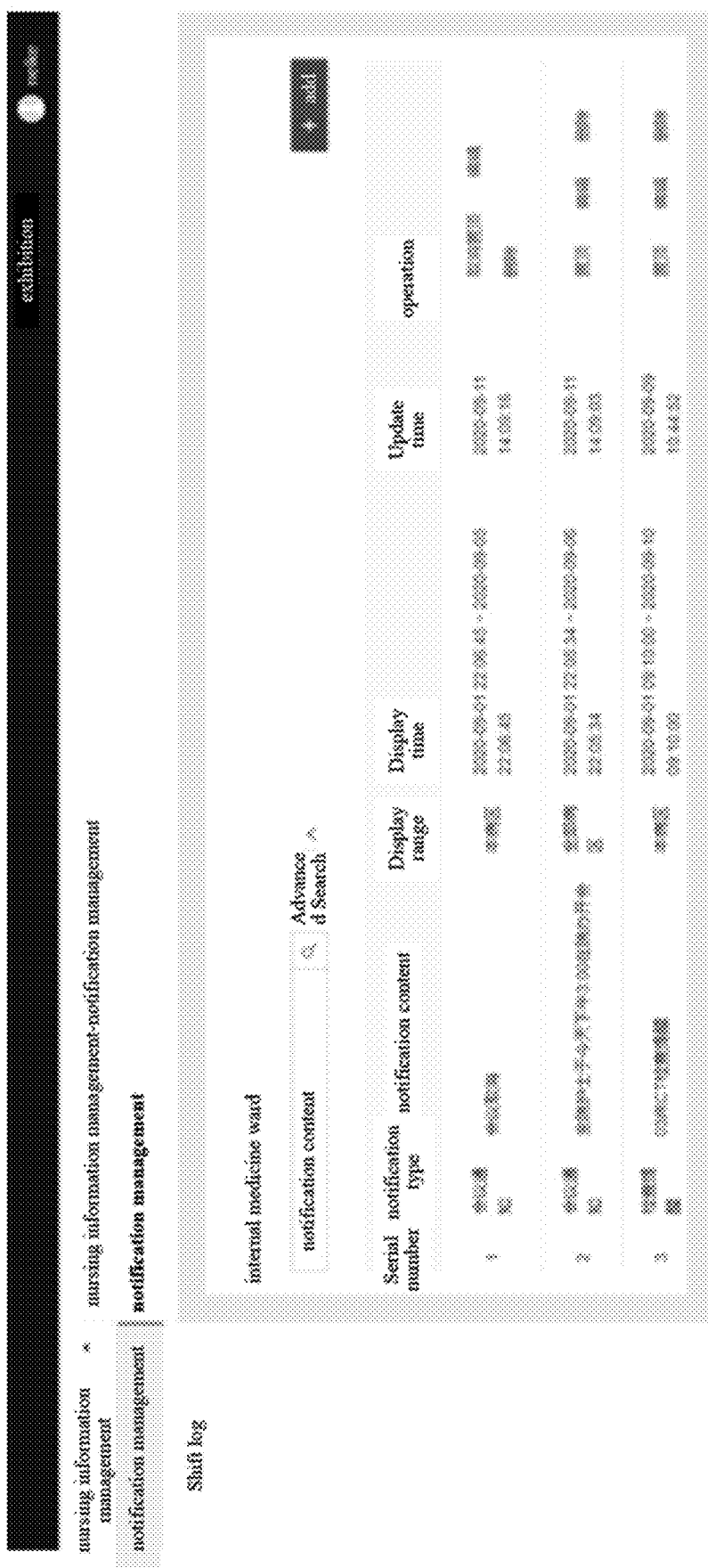

As shown in FIG. 10b, in response to the third user's operation of clicking on "nursing information management-notification management", the server presents a notification management page for displaying a list of notifications for this ward, including operations such as adding, editing, deleting, placing on top and canceling on top.

Figure 10C:
Figure 10D:
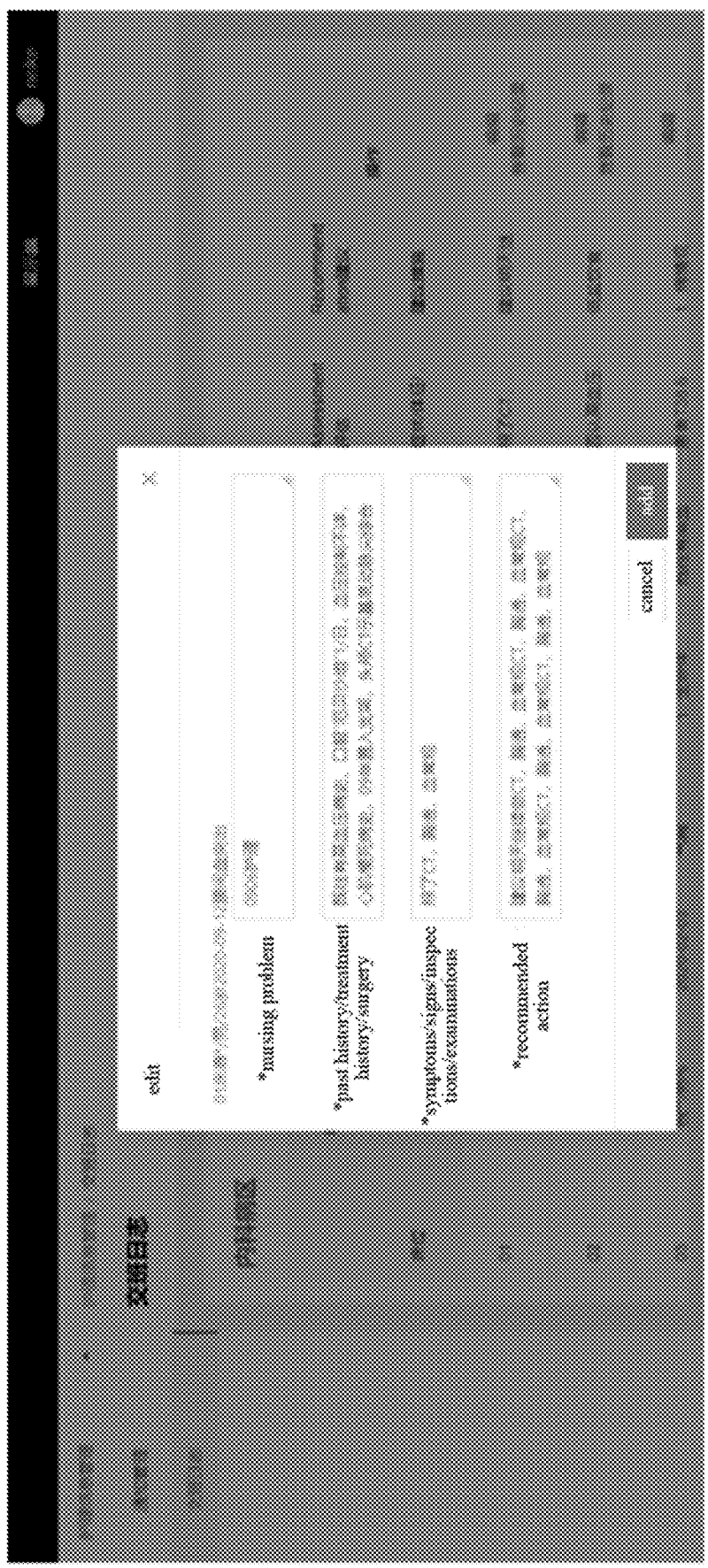

As shown in FIG. 10c, in response to the third user's operation of clicking on "nursing information management-shift log", the server presents a shift log page for displaying a list of shift logs for patients in the ward. Further, as shown in FIG. 10d, in response to the third user's operation of clicking on an "edit" button, the server pops up an edit pop-up window so that the shift log can be modified, including: editing of nursing problems, past history/treatment history/surgery, and symptoms/signs/inspections/examinations and recommended measures for designated inpatients As shown in FIG. 10e to FIG. 10h, the server further includes hospital information management components, which specifically include: health propaganda-education management, hospital introduction management, hospital headline management, and hospital ordering management.

Figure 10E:
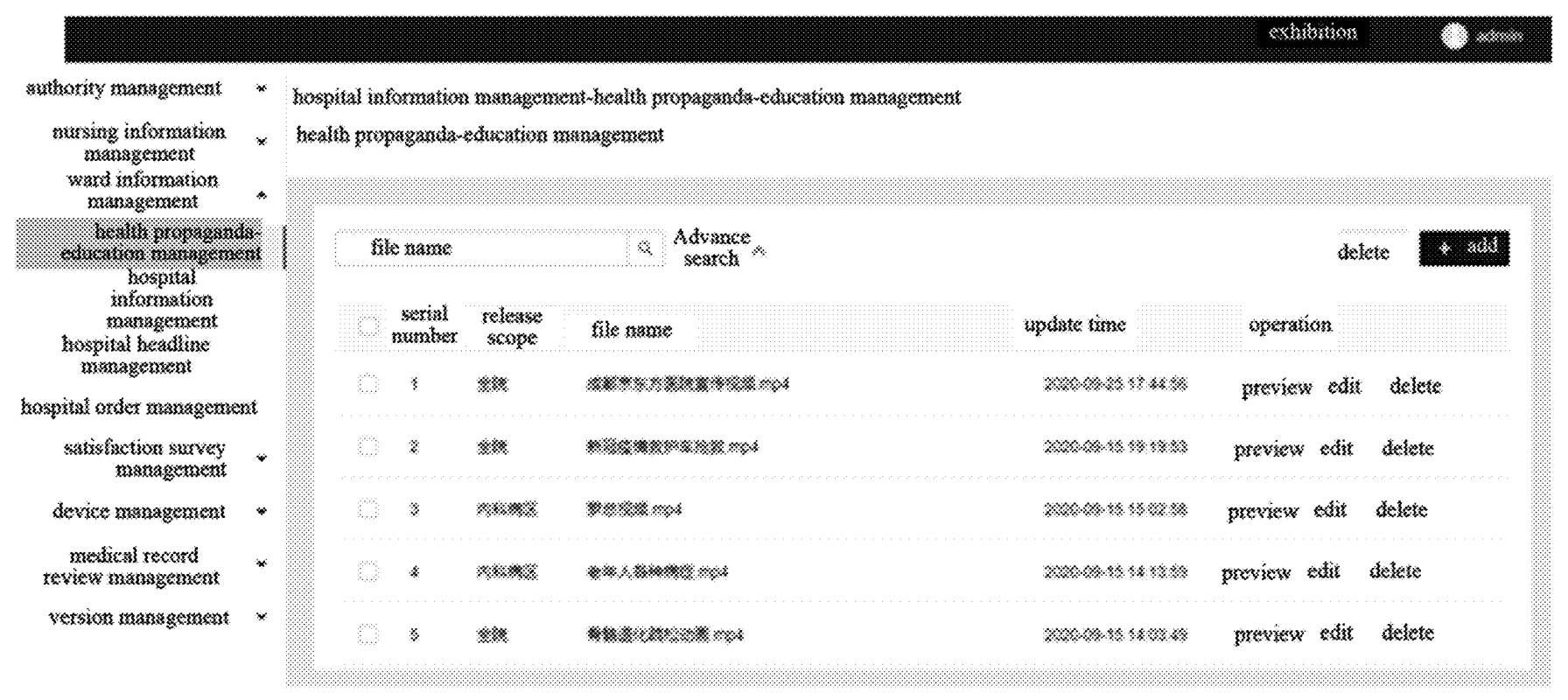

Specifically, as shown in FIG. 10e, in response to the third user's operation of clicking on a menu "hospital information management-health propaganda-education management", the server presents a propaganda-education list, including: adding, previewing, editing, and deleting of propaganda-education videos.

Figure 10F:
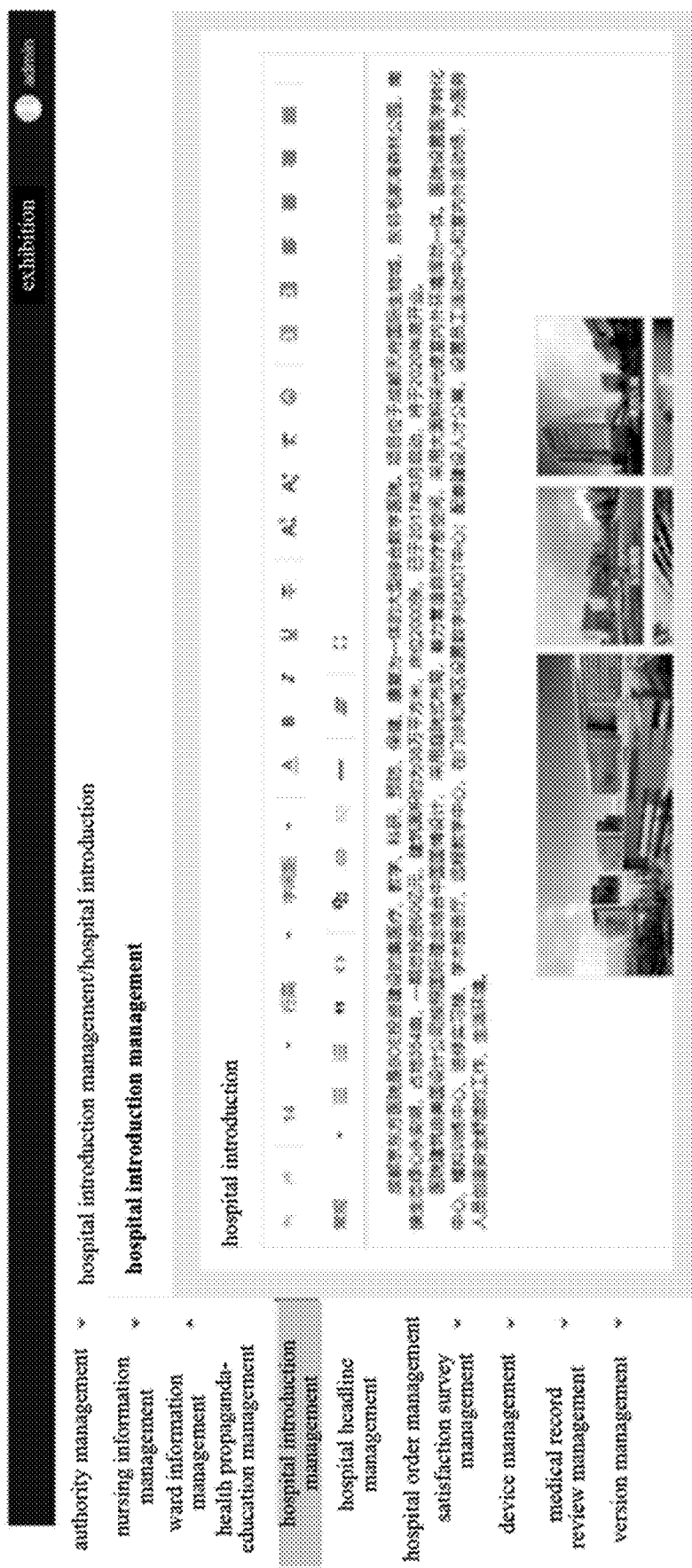

As shown in FIG. 10f, in response to the third user's operation of clicking on a menu "hospital information management-hospital introduction management", the server presents a hospital introduction editing page to edit the hospital introduction.

Figure 10G:
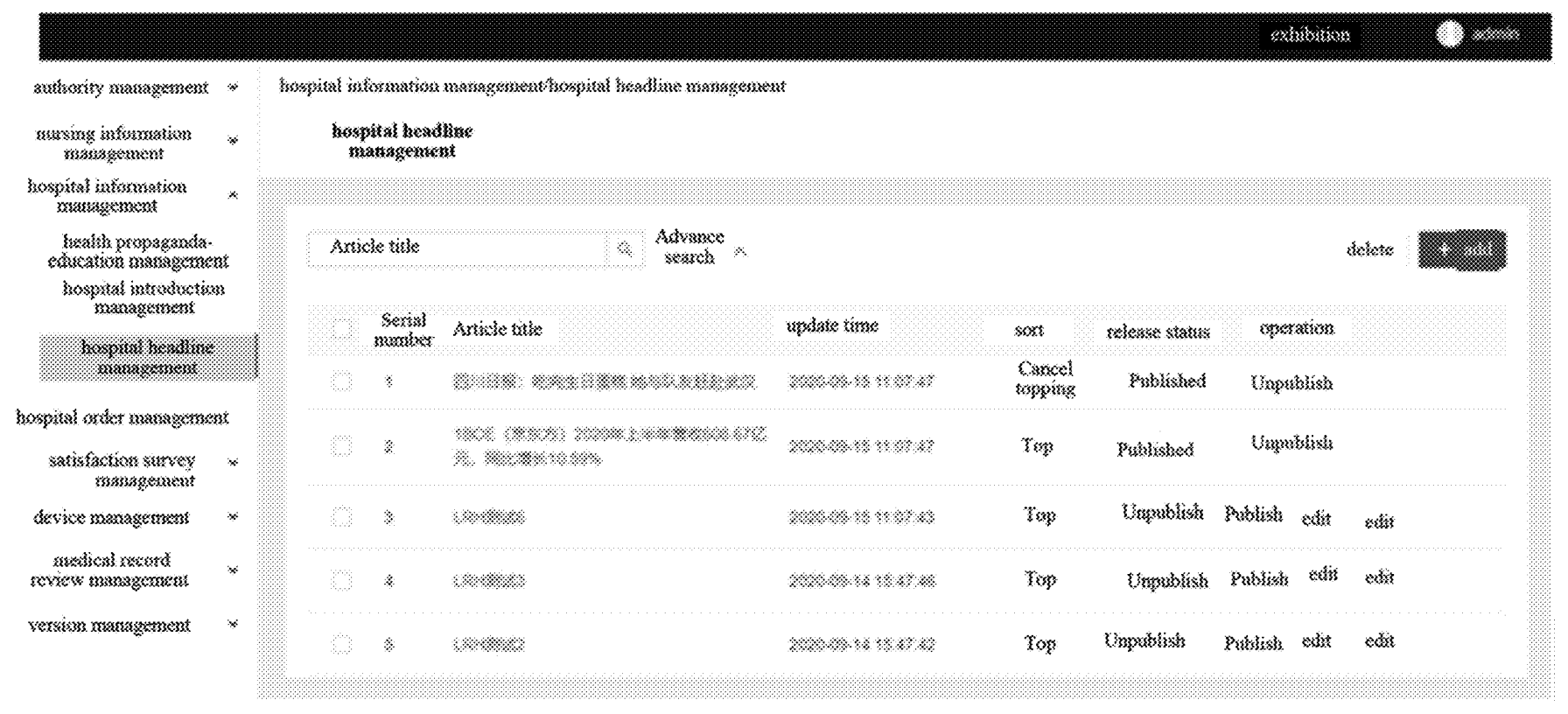

As shown in FIG. 10g, in response to the third user's operation of clicking on a menu "hospital information management-hospital headline management", the server presents a list of hospital headlines, including adding, publishing, un-publishing, editing, previewing, placing on top, canceling on top, and deleting.

Figure 10H:

As shown in FIG. 10h, in response to the third user's operation of clicking on a menu "hospital information management-hospital ordering management", the server presents a list of hospital set meals, including adding, copying, editing, deleting and viewing ordering records.

Figure 10J:
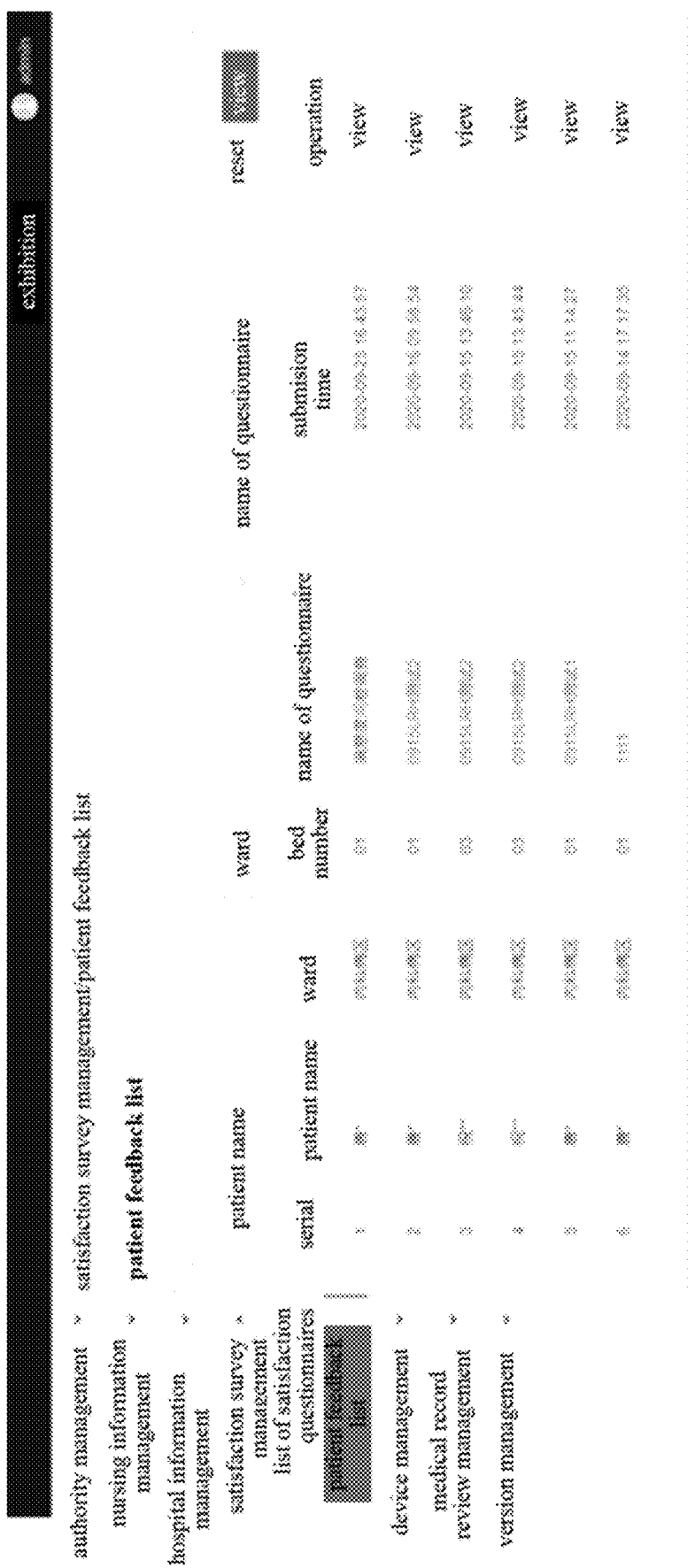

As shown in FIG. 10i and FIG. 10j, the server further includes a satisfaction survey component, which specifically includes a satisfaction questionnaire list and a patient feedback list.

As shown in FIG. 10i, in response to the third user's operation of clicking on a menu "satisfaction survey management-satisfaction questionnaire list", the server presents a list of satisfaction questionnaires, including operations such as adding, previewing, publishing, un-publishing, editing, and deleting of the questionnaire.

As shown in FIG. 10j, in response to the third user's operation of clicking on a menu "satisfaction survey management-patient feedback list", the server presents a list of patient feedback. Response details of each inpatient can be views by clicking on corresponding patient feedback.

Figure 10K:
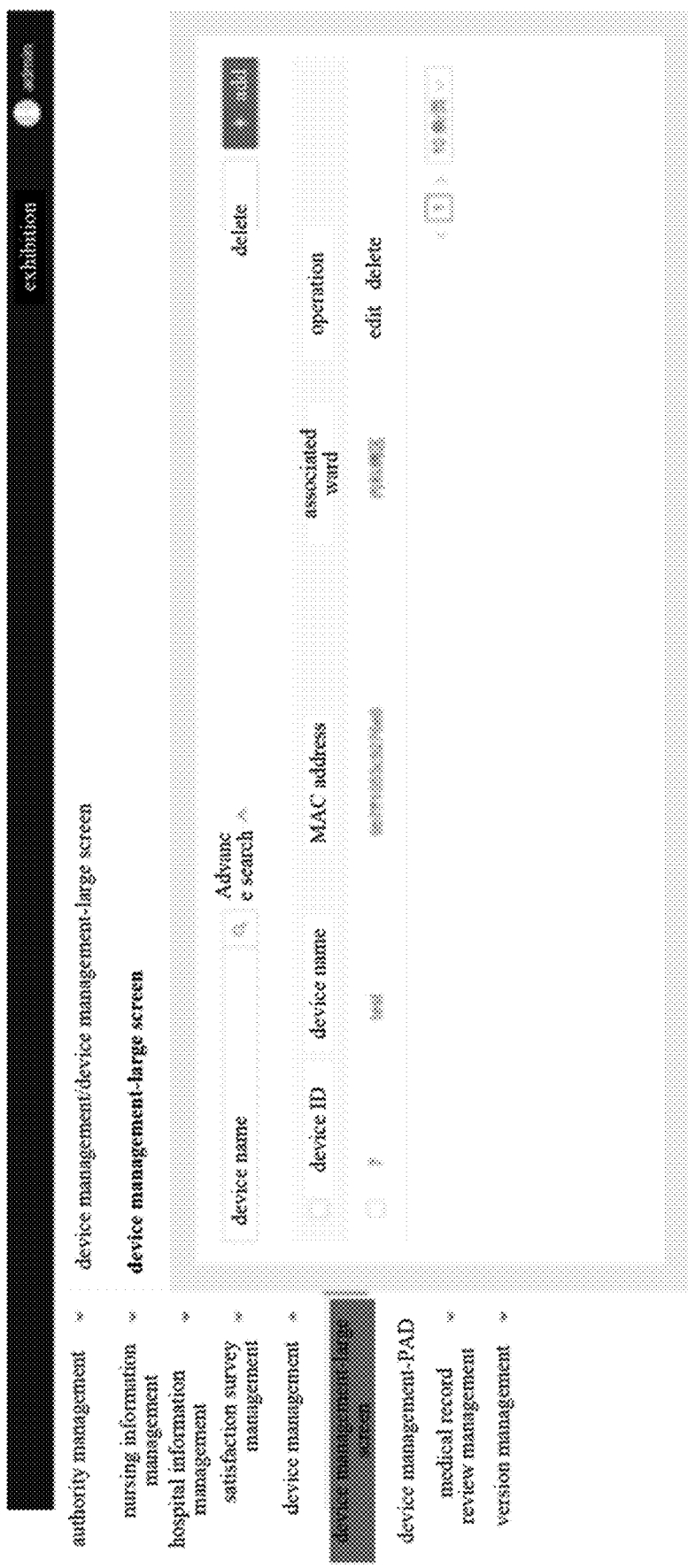

As shown in FIG. 10k and FIG. 10l, the server further includes a device management component, which specifically includes multiple connected second terminals and multiple connected first terminals.

As shown in FIG. 10k, in response to the third user's operation of clicking on a menu "device management-device management-large screen", the server presents a list of large screens, i.e., second terminals, including operations of adding, editing, and deleting of devices.

As shown in FIG. 10l, in response to the third user's operation of clicking on a menu "device management-device management-PAD", the server presents a list of PADs, i.e., first terminals, including operations such as adding, editing, deleting, and night mode setting of devices.

Figure 10M:
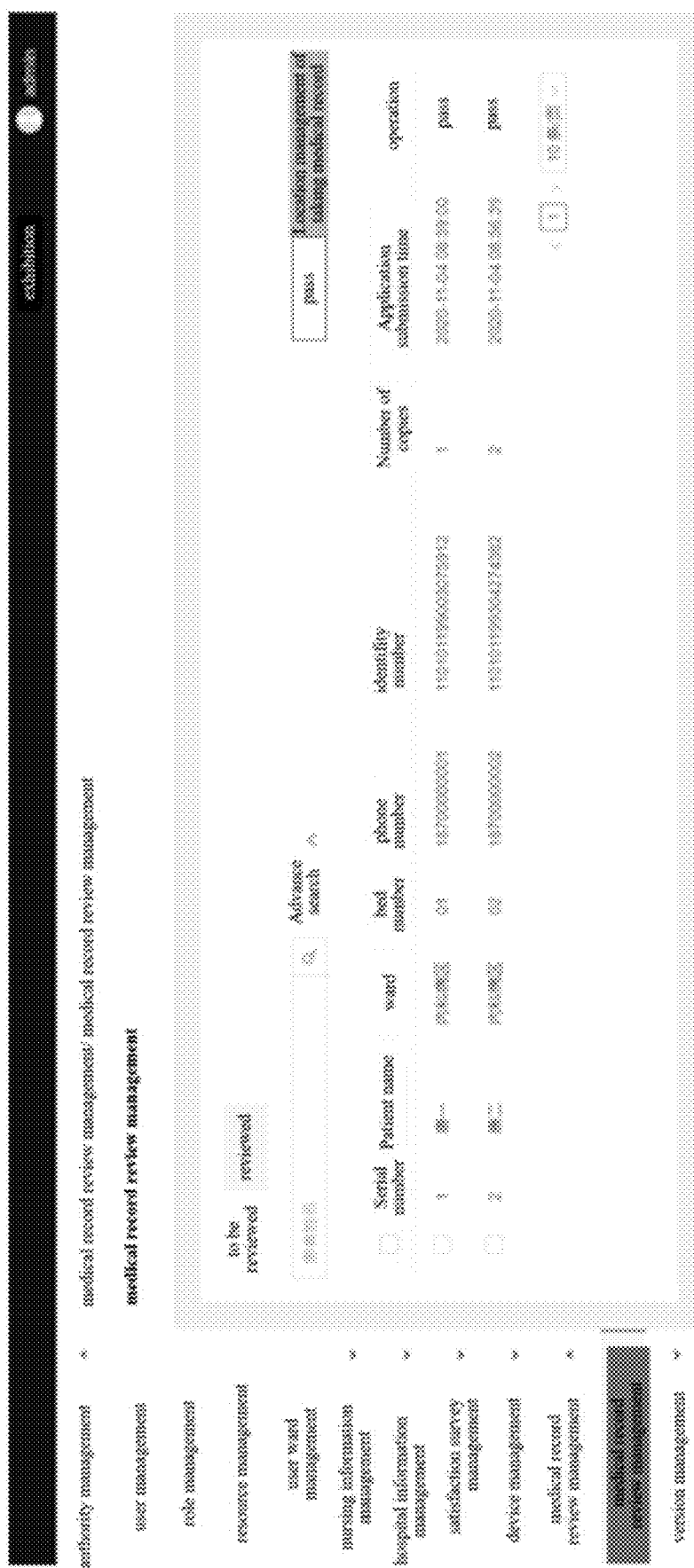
Figure 10N:
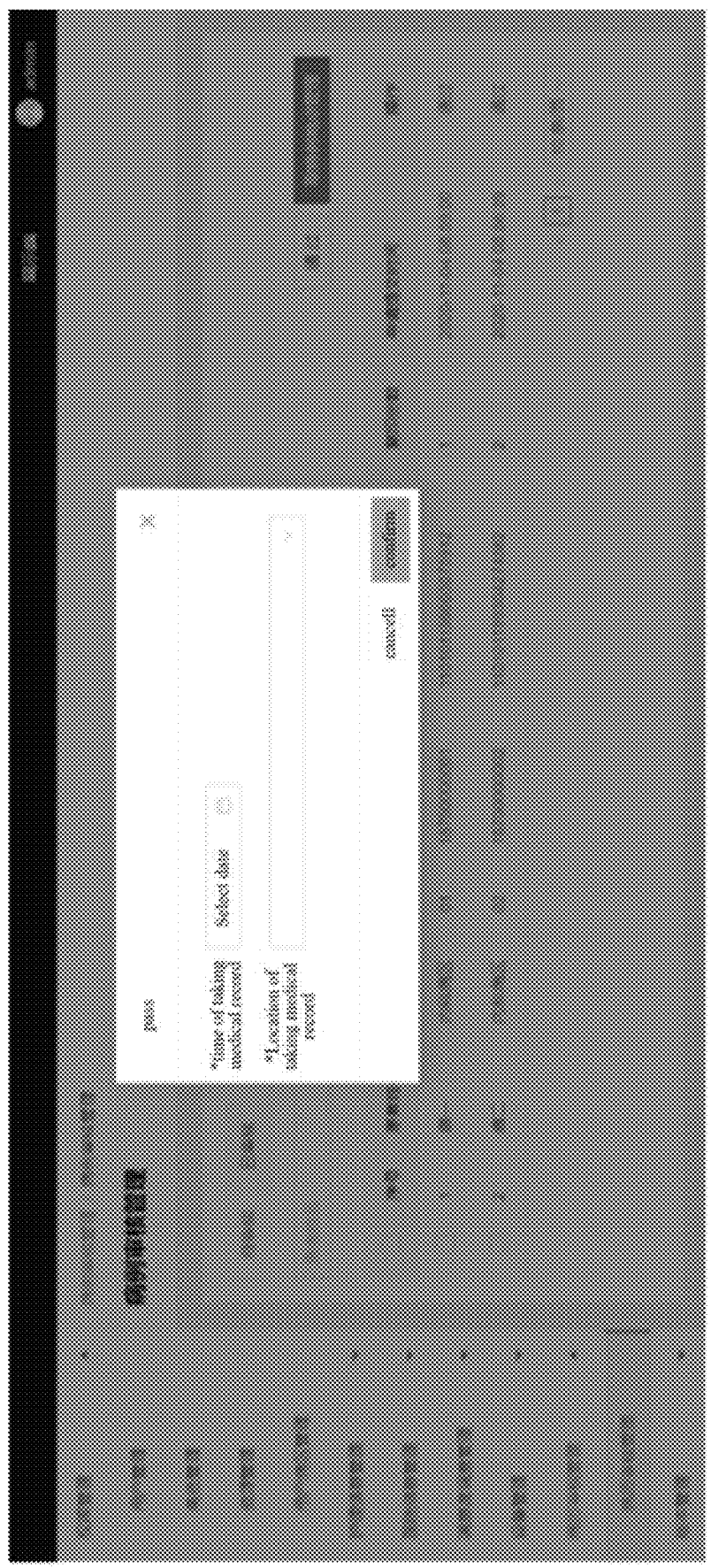

As shown in FIG. 10m and FIG. 10n, the server further includes a medical record review management component. As shown in FIG. 10m, in response to the third user's operation of clicking on a menu "medical record review management-medical record review management", the server presents a medical record review management interface. As shown in FIG. 10n, in response to the third user's operation of clicking on "pass" button, the server presents a pop-up window for setting time and positon of collection, and editing the time and position of collection.

Figure 10O:
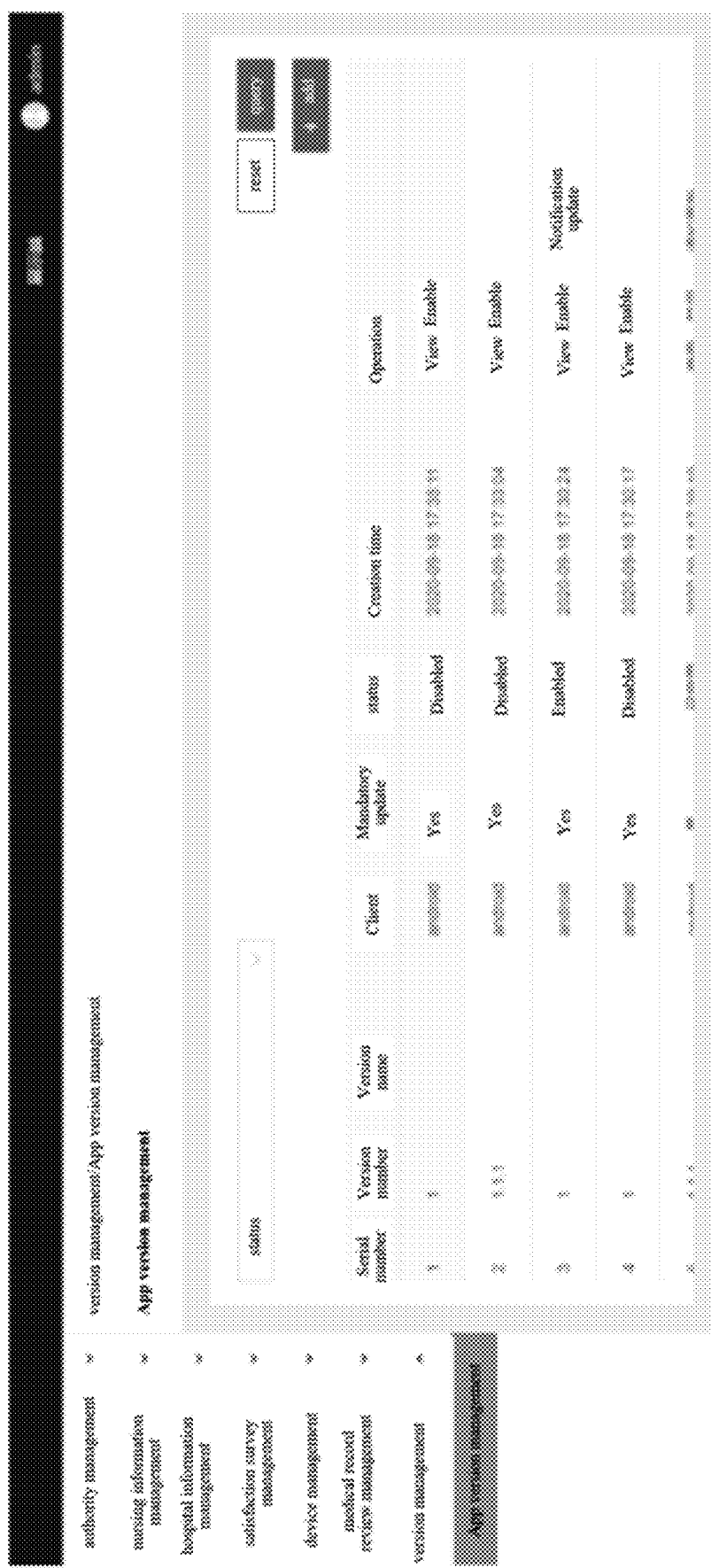
Figure 10P:
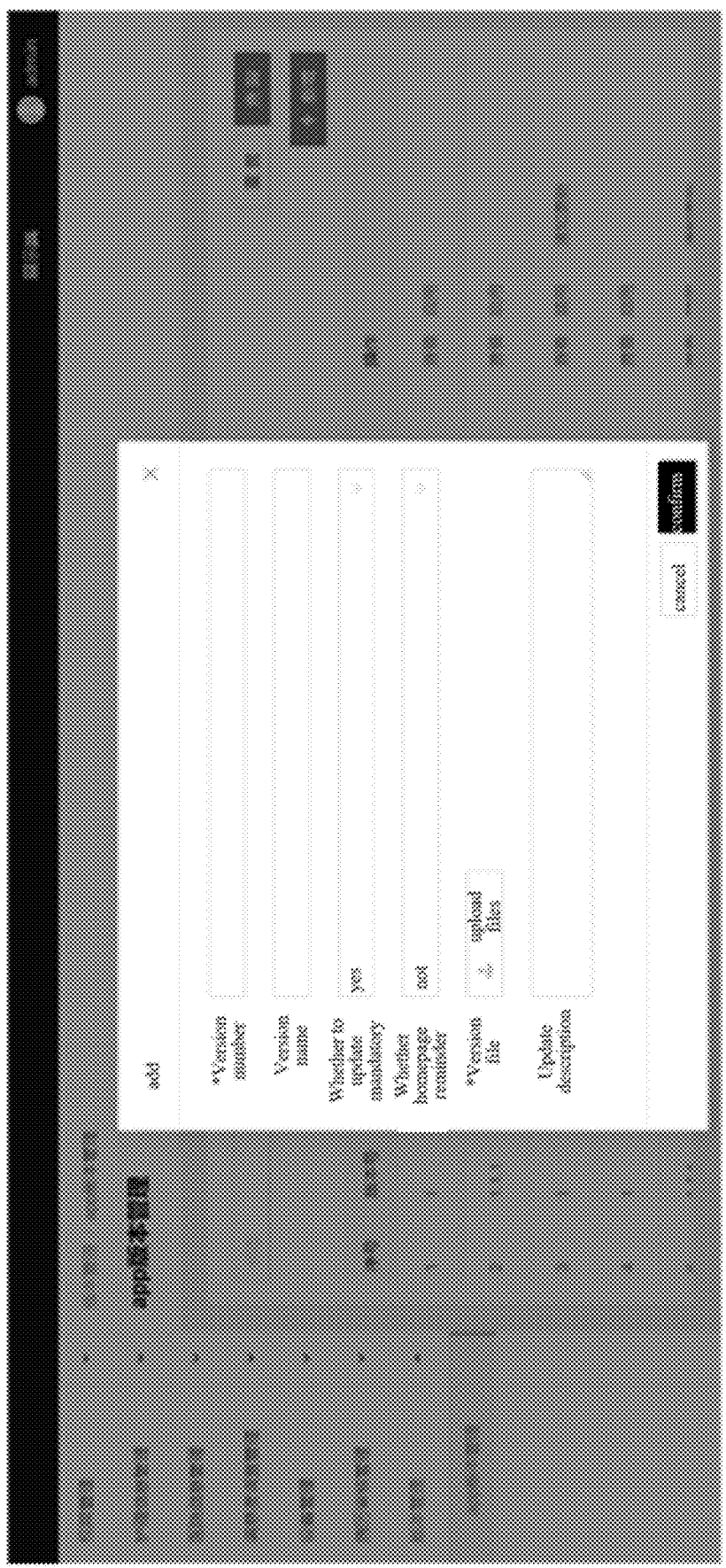
Figure 10Q:
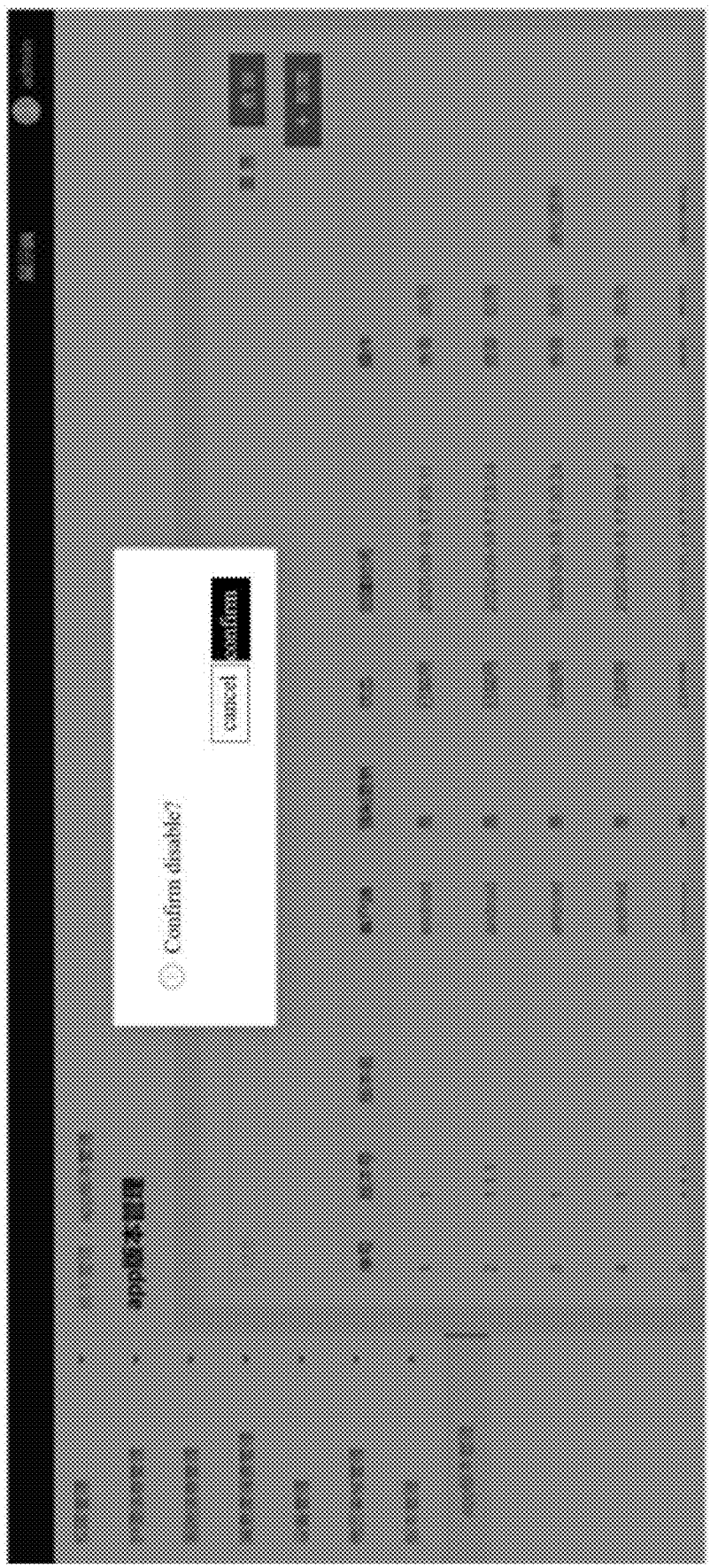
Figure 10R:
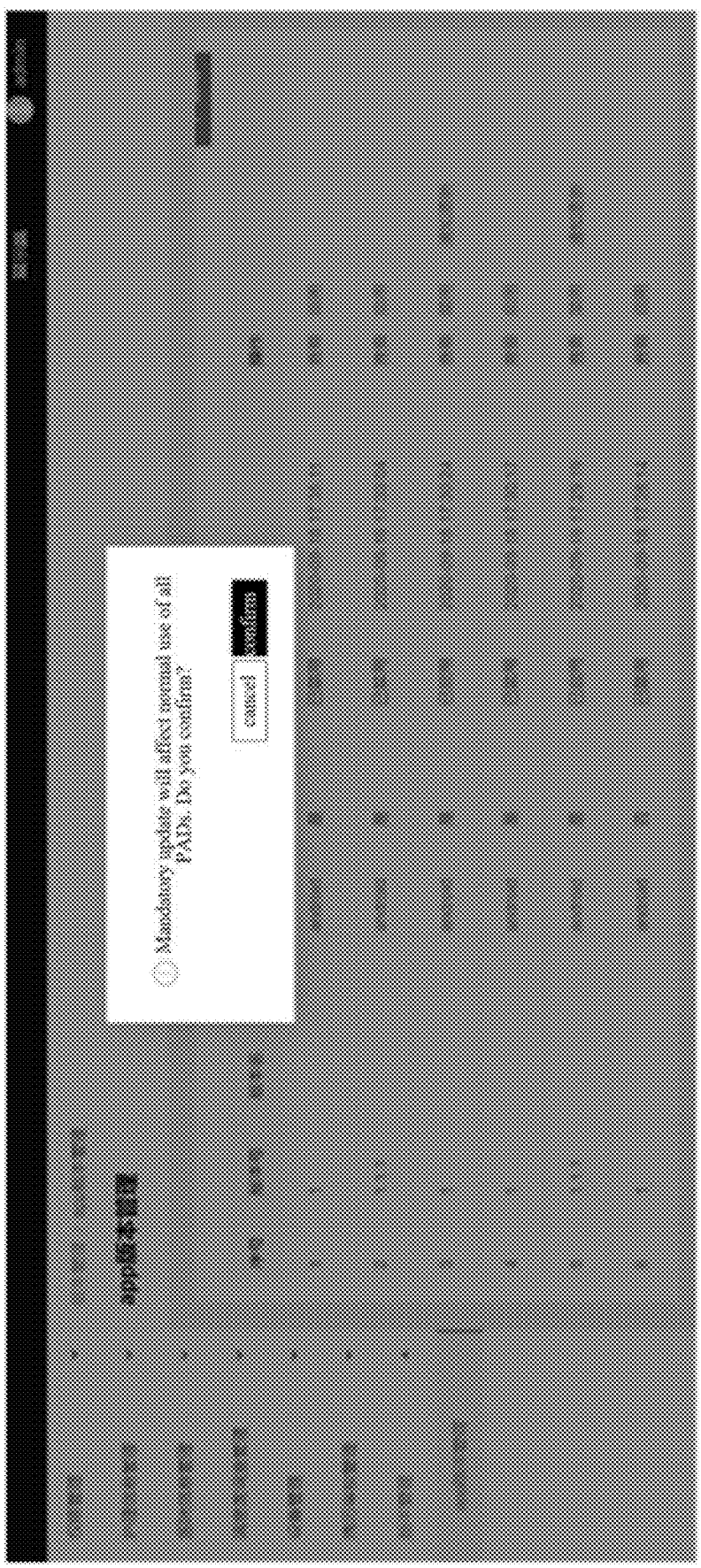

As shown in FIG. 10o to FIG. 10r, the server further includes a version management component. As shown in FIG. 10o, in response to the third user's operation of clicking on a menu "version management-app version management", the server presents a version management interface, including operations such as adding new app version, viewing, enabling, disabling and notifying updates. Specifically, as shown in FIG. 10p, in response to the third user's operation of clicking on "add" button, the server presents a pop-up window for adding. As shown in FIG. 10q, in response to the third user's operation of clicking on "disable" button, the server presents a pop-up window for disabling. As shown in FIG. 10r, in response to the third user's operation of clicking on "notifying update", the server presents a pop-up window for notifying update.

In this embodiment, the server can manage the first terminal and the second terminal through the presented interface components, maintain and update each interface component, thereby effectively simplifying management of inpatients and medical staff in the inpatient department in the existing management system, stabilizing mood of inpatients, effectively improving the work efficiency of medical staff, and realizing a smart ward based on communication interaction between the first terminal, the second terminal and the server, and then remedying the problems in the related art and having a wide range of application prospects.

Based on the foregoing communication method, one embodiment of the present application provides a server, including a processor and an MQTT message queue. The processor is configured to bind a first terminal, and allocate a first identity identifier and corresponding function control information to the first terminal according to first terminal information. The processor is further configured to generate function feedback information according to a first function request of the first terminal. The processor is further configured to connect with a second terminal and transmit corresponding menu control to the second terminal according to a second identity identifier of the second terminal. The processor is further configured to generate function feedback information according to a second function request of the second terminal. The MQTT message queue is configured to, based on the MQTT protocol, connect the first terminal, the second terminal, and the processor, respectively. The MQTT message queue is further configured to, receive the first function request of the first terminal or the second function request of the second terminal, and push the first function request of the first terminal or the second function request of the second terminal to the processor. The MQTT message queue is further configured to receive the function feedback information generated by the processor, and push the function feedback information to the first terminal or the second terminal.

The server provided in this embodiment is a background system that interacts with the first terminal and the second terminal, presents and maintains as well as updates each interface component, and manages the first terminal and the second terminal through each interface component. The server provides convenient information inquiry and scheduling for the first user and the second user, simplifies the existing management system, effectively improves the user experience of patients and medical staff, and realizes information interaction, management and maintenance of smart wards, which has a wide range of application prospects. The specific implementation is the same as the foregoing embodiment, and will not be repeated here.

Figure 11:
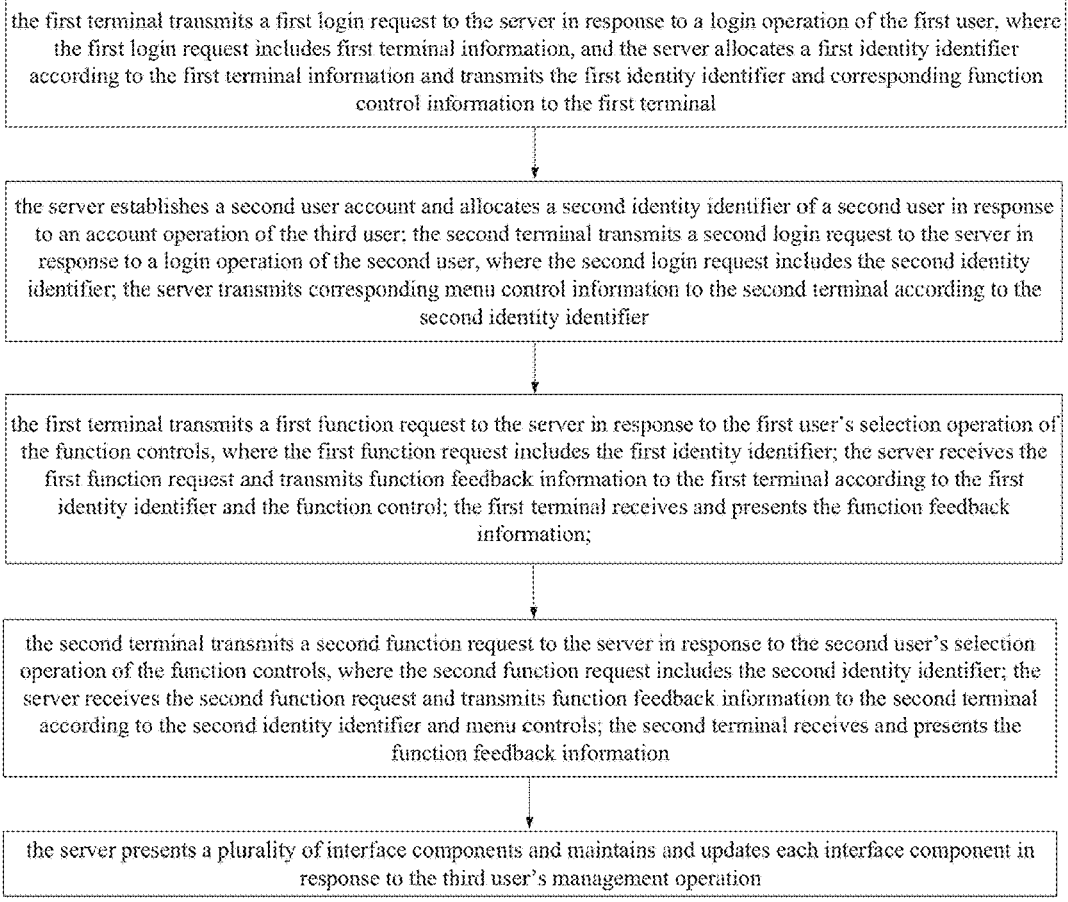
FIG. 11 is a flowchart of a communication method according to another embodiment of the present application.

Based on the foregoing embodiment, one embodiment of the present application provides a communication method applied to a communication system. As shown in FIG. 11, the method includes: the first terminal transmits a first login request to the server in response to a login operation of the first user, where the first login request includes first terminal information, and the server allocates a first identity identifier according to the first terminal information and transmits the first identity identifier and corresponding function control information to the first terminal; the server establishes a second user account and allocates a second identity identifier of a second user in response to an account operation of the third user; the second terminal transmits a second login request to the server in response to a login operation of the second user, where the second login request includes the second identity identifier; the server transmits corresponding menu control information to the second terminal according to the second identity identifier; the first terminal transmits a first function request to the server in response to the first user's selection operation of the function controls, where the first function request includes the first identity identifier; the server receives the first function request and transmits function feedback information to the first terminal according to the first identity identifier and the function control; the first terminal receives and presents the function feedback information; the second terminal transmits a second function request to the server in response to the second user's selection operation of the function controls, where the second function request includes the second identity identifier; the server receives the second function request and transmits function feedback information to the second terminal according to the second identity identifier and menu controls; the second terminal receives and presents the function feedback information; the server presents a plurality of interface components and maintains and updates each interface component in response to the third user's management operation.

The communication method provided in this embodiment realizes management of inpatients and medical staff through the first terminal and the second terminal which are interacted with the server, respectively, thereby simplifying the existing management system, effectively improving user experience of patients and the medical staff, remedying the problems in the related art and having a wide range of application prospects.

In an optional embodiment, the server includes an MQTT message queue and a processor. The foregoing steps that the first terminal transmits a first function request to the server in response to the first user's selection operation on the function control, where the first function request includes the first identity identifier; the server receives the first function request and transmits function feedback information to the first terminal according to the first identity identifier and function controls; the first terminal receives and presents the function feedback information, includes: in response to the first user's selection operation of the function controls, the first terminal transmits a first function request to the MQTT message queue based on the MQTT protocol; the MQTT message queue pushes the first function request to the processor; and the processor generates function feedback information according to the first identity identifier and function controls in the first function request and transmits function feedback information to the MQTT message queue; the MQTT message queue pushes the function feedback information to the first terminal according to the first identity identifier; the first terminal receives and presents the function feedback information. The the foregoing steps that the second terminal transmits a second function request to the server in response to the second user's selection operation of the menu controls, where the second function request includes the second identity identifier; the server receives the second function request and transmits function feedback information to the second terminal according to the second identity identifier and the menu controls; the second terminal receives and presents the function feedback information, further includes: the second terminal transmits a second function request to the MQTT message queue based on the MQTT protocol in response to the second user's selection operation of the menu controls; the MQTT message queue pushes the second function request to the processor; the processor generates function feedback information according to the second identity identifier and the menu control in the second function request, and transmits the function feedback information to the MQTT message queue; the MQTT message queue pushes the function feedback information to the second terminal according to the second identity identifier, and the second terminal receives and presents the function feedback information.

Based on the foregoing communication method, one embodiment of the present application provides a communication system, including: a server; a first terminal, and a second terminal. The first terminal is configured to bind the server, and transmit a first function request to the server through a function control to receive and present function feedback information transmitted by the server. The second terminal is configured to connect to the server, transmit a second function request to the server through a menu control to receive and present function feedback information transmitted by the server. The server includes a processor and an MQTT message queue. The processor is configured to bind the first terminal and generate function feedback information according to the first function request of the first terminal. The processor is further configured to connect to the second terminal generates function feedback information according to the second function request of the second terminal. The MQTT message queue is configured to, based on the MQTT protocol, connect the first terminal, the second terminal and the processor, respectively; and receive the first function request of the first terminal or the second function request of the second terminal, push the first function request of the first terminal or the second function request of the second terminal to the processor, and receive the function feedback information generated by the processor and push the function feedback information to the first terminal or the second terminal.

The communication method provided in this embodiment realizes management of inpatients and medical staff through the first terminal and the second terminal that are interacted with the server, respectively, thereby simplifying the existing management system, effectively improving user experience of patients and the medical staff, remedying the problems in the related art and having a wide range of application prospects.

Another embodiment of the present application provides a computer-readable storage medium, including a computer program stored thereon. The program is executed by the processor to implement: in response to a first login request of a first terminal, a server allocates a first identity identifier according to first terminal information in the first login request, and transmits the first identity identifier and corresponding function control information to the first terminal; the server establishes a second user account in response to an account operation of a third user and allocates a second identity identifier for a second user, and in response to a second login request of a second terminal, the server transmits corresponding menu control information to the second terminal according to the second identity identifier in the second login request; in response to a first function request of the first terminal, the server transmits function feedback information to the first terminal according to the first identity identifier and a function control in the first function request; in response to a second function request of the second terminal, the server transmits function feedback information to the second terminal according to the second identity identifier and a menu control in the second function request; and, the server presents a plurality of interface components, and maintains and updates each interface component in response to an management operation of the third user.

Another embodiment of the present application provides a computer-readable storage medium including a computer program stored thereon. The program is executed by a processor to implement: a first terminal transmits a first login request to a server in response to a login operation of a first user, where the first login request includes first terminal information; the first terminal receives a first identity identifier transmitted by the server and presents function controls corresponding to the first identity identifier, where the first identity identifier is allocated by the server according to the first terminal information; the first terminal transmits a first function request to the server in response to the first user's selection operation of the function controls, receives and presents function feedback information transmitted by the server. The first function request includes the first identity identifier.

Another embodiment of the present application provides a computer-readable storage medium including a computer program stored thereon. The program is executed by a processor to implement: a second terminal transmits a second login request to a server in response to a login operation of a second user, where the second login request includes a second identity identifier and the second identity identifier is allocated by the server in response to management operation of a third user; the second terminal presents a plurality of menu controls corresponding to the second identity identifier; the second terminal transmits a second function request to the server in response to the second user's selection operation of the menu controls, receives and presents function feedback information transmitted by the server. The second function request includes the second identity identifier.

In practical applications, the computer-readable storage medium may adopt any combination of one or more computer-readable medium. The computer-readable medium may be a computer-readable signal medium or a computer-readable storage medium. The computer-readable storage medium may be, for example, but not limited to, an electrical, magnetic, optical, electromagnetic, infrared, or semiconductor system, apparatus, or device, or a combination of any of the above. More specific examples (non-exhaustive list) of the computer-readable storage medium include: electrical connections with one or more wires, portable computer disks, hard disks, random access memory (RAM), read-only memory (ROM), erasable programmable read only memory (EPROM or flash memory), optical fiber, portable compact disk read only memory (CD-ROM), optical storage device, magnetic storage device, or any suitable combination of the above. In this embodiment, the computer-readable storage medium may be any tangible medium that contains or stores a program, and the program may be used by or in combination with an instruction execution system, apparatus, or device.

The computer-readable signal medium may include a data signal propagated in baseband or as a part of a carrier wave, and carrying computer-readable program code. This propagated data signal may take many forms, including but not limited to electromagnetic signals, optical signals, or any suitable combination of the foregoing. The computer-readable signal medium may also be any computer-readable medium other than a computer-readable storage medium. The computer-readable medium may transmit, propagate, or transmit a program that is used by or in combination with an instruction execution system, apparatus, or device.

The program code contained on the computer-readable medium may be transmitted by any suitable medium, including but not limited to wireless, wire, optical cable, RF, etc., or any suitable combination of the above.

The computer program code used to perform the operations of the present application may be written in one or more programming languages or a combination thereof. The programming languages include object-oriented programming languages, such as Java, Smalltalk, C++, and further includes conventional procedural programming languages, such as "C" language or similar programming language. The program code may be executed entirely on the user's computer, partly on the user's computer, executed as an independent software package, partly on the user's computer and partly executed on a remote computer, or entirely executed on the remote computer or server. In a case of a remote computer, the remote computer may be connected to the user's computer through any kind of network, including a local area network (LAN) or a wide area network (WAN), or it may be connected to an external computer (for example, using internet connection provided by an internet service provider).

Figure 12:
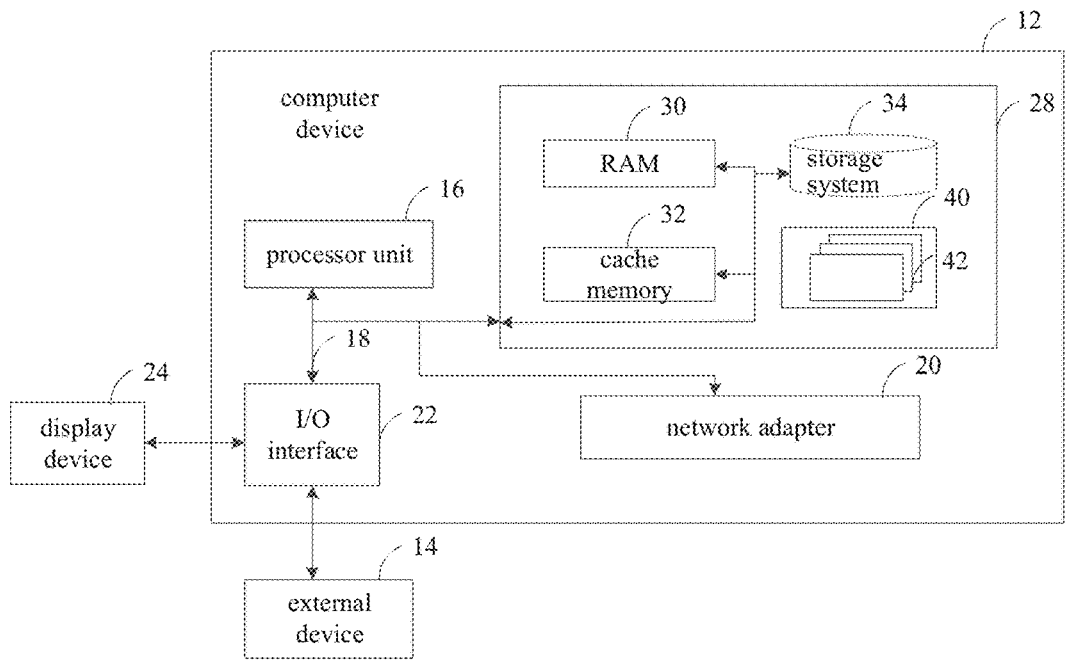
FIG. 12 is a schematic structural diagram of a computer device according to another embodiment of the present application.

As shown in FIG. 12, it shows a schematic structural diagram of a computer device provided in another embodiment of the present application. The computer device 12 shown in FIG. 12 is only an example, and should not bring any limitation to the function and application scope of the embodiments of the present application.

As shown in FIG. 12, the computer device 12 is represented in the form of a general-purpose computing device. Components of the computer device 12 may include, but not limited to: one or more processors or processing units 16, a system memory 28, and a bus 18 connecting different system components (including the system memory 28 and the processing unit 16).

The bus 18 represents one or more of several types of bus structures, including a memory bus or a memory controller, a peripheral bus, a graphics acceleration port, a processor, or a local bus using any bus structure among multiple bus structures. For example, these architectures include, but not limited to, industry standard architecture (ISA) bus, microchannel architecture (MAC) bus, enhanced ISA bus, video electronics standards association (VESA) local bus, and peripheral component interconnection (PCI) bus.

The computer device 12 typically includes a variety of computer system readable medium. These medium may be any available medium that can be accessed by the computer device 12, including volatile and nonvolatile medium, removable and non-removable medium.

The system memory 28 may include computer system readable medium in the form of volatile memory, such as random access memory (RAM) 30 and/or cache memory 32. The computer device 12 may further include other removable/non-removable, volatile/nonvolatile computer system storage medium. For example only, the storage system 34 may be used to read and write non-removable, non-volatile magnetic medium (not shown in FIG. 12, usually referred to as a "hard drive"). Although not shown in FIG. 12, a disk drive for reading and writing to a removable non-volatile disk (such as a "floppy disk") and an optical disk drive for reading and writing to a removable non-volatile optical disk (such as CD-ROM, DVD-ROM, or other optical media) can be provided. In these cases, each drive may be connected to the bus 18 through one or more data media interfaces 18. The memory 28 may include at least one program product, and the program product has a set of (for example, at least one) program modules, and these program modules are configured to perform the functions of the embodiments of the present application.

A program/utility tool 40 having a set of (at least one) program module 42 may be stored in, for example, the memory 28. Such program module 42 includes but is not limited to an operating system, one or more application programs, other program modules, and program data. Each of these examples or some combination may include implementation of a network environment. The program module 42 usually executes functions and/or methods in the embodiments described in the present application.

The computer device 12 may further communicate with one or more external devices 14 (such as a keyboard, pointing device, display device 24), and may also communicate with one or more devices that enable a user to interact with the computer device 12, and/or communicate with any device (such as a network card, modem) that enables the computer device 12 to communicate with one or more other computing devices. Such communication can be performed through an input/output (I/O) interface 22. In addition, the computer device 12 may also communicate with one or more networks (for example, a local area network (LAN), a wide area network (WAN), and/or a public network, such as the internet) through a network adapter 20. As shown in FIG. 12, the network adapter 20 communicates with other modules of the computer device 12 through the bus 18. It should be understood that although not shown in FIG. 12, other hardware and/or software modules may be used in conjunction with the computer device 12, including but not limited to: microcode, device drivers, redundant processing units, external disk drive arrays, RAID systems, tapes drives and data backup storage systems, etc.

The processor unit 16 executes various function applications and data processing by running programs stored in the system memory 28, for example, to implement a communication method provided in the embodiment of the present application.

In view of the current existing problems, the present application formulates a communication method, terminal, server, communication system, computer device and medium, and realizes the management of inpatients and medical staff through the first terminal and the second terminal that interact with the server respectively, thereby simplifying the existing management system, effectively improving user experience of patients and the medical staff, remedying the problems in the related art and having a wide range of application prospects.

The above are merely the embodiments of the present disclosure and shall not be used to limit the scope of the present disclosure. It should be noted that, a pedestrian skilled in the art may make improvements and modifications without departing from the principle of the present disclosure, and these improvements and modifications shall also fall within the scope of the present disclosure. The protection scope of the present disclosure shall be subject to the protection scope of the claims.

What is claimed is:

1. A communication method, applied to a first terminal, comprising:
   transmitting a first login request to a server in response to a login operation of a first user, wherein the first login request includes first terminal information;
   receiving a first identity identifier transmitted by the server and presenting multiple function controls corresponding to the first identity identifier, wherein the first identity identifier is allocated by the server according to the first terminal information;
   in response to the first user's selection operation on the function controls, transmitting a first function request to the server, receiving and presenting function feedback information transmitted by the server, wherein the first function request includes the first identity identifier:
   wherein the server includes an MQTT message queue and a processor;
   wherein in response to the first user's selection operation on the function controls, transmitting the first function request to the server, receiving and presenting function feedback information transmitted by the server, further includes:
   in response to the first user's selection operation on the function controls, transmitting the first function request to the MQTT message queue based on the MQTT protocol, so that the MQTT message queue pushes the first function request to the processor;
   receiving and presenting the function feedback information transmitted by the server, wherein the function feedback information is transmitted by the processor according to the received first function request, and pushed to the first terminal corresponding to the first identity identifier through the MQTT message queue; and
   wherein the first terminal is grouped and message processing and push rules are set according to different topics and subscriptions to transmit a message to each first terminal and transmit a message to a designated first terminal.

2. The communication method according to claim 1, wherein the multiple function controls include at least two of reminder message control, medical record control, reporting control, bill control, appointment control, propaganda-education control, ordering control, medical record copy control, electronic signature control, satisfaction survey control or file control.

3. The communication method according to claim 2, wherein in response to the first user's selection operation on the function controls, transmitting the first function request to the server, receiving and presenting function feedback information transmitted by the server, further includes at least one of the following:
   in response to a selection operation of the first user on the ordering control, presenting nutrition prompt information, a food selection list, and a time selection control for the first user;

in response to a selection operation of the first user on the bill control, presenting a bill list of the first user and a recharge control; wherein the recharge control is connected to a third-party payment interface;

in response to a selection operation of the first user on the reminder message control, presenting a reminder message list for the first user;

in response to a selection operation of the first user on the medical record control, presenting medical record information of the first user;

in response to a selection operation of the first user on the reporting control, presenting a report list of the first user; in response to a selection operation of the first user on the appointment control, presenting an appointment list of the first user; wherein the appointment list includes an examination appointment and a surgery appointment;

in response to a selection operation of the first user on the propaganda-education control, presenting a propaganda-education list;

in response to a selection operation of the first user on the medical record copy control, presenting a medical record copy application form;

in response to a selection operation of the first user on the electronic signature control, presenting a signature list;

in response to a selection operation of the first user on the satisfaction survey control, presenting a questionnaire; or in response to a selection operation of the first user on the file control, presenting corresponding user files.

4. The communication method according to claim 1, wherein the communication method further includes:

receiving the first identity identifier transmitted by the server, and presenting user information corresponding to the first identity identifier as well as a reminder message corresponding to the first identity identifier;

wherein the user information includes at least one of user name, gender, hospitalization information, medical staff information, or user's QR code information; the reminder message includes at least one of an examination reminder, an operation reminder, or a medical record receipt reminder.

5. A terminal for implementing the communication method according to claim 1, comprising:

a display unit including a binding control and a function control;

wherein the binding control is configured to transmit a first login request to the server to establish a binding connection, and obtain a first identity identifier and a plurality of corresponding function controls according to first terminal information in the first login request;

the function control is configured to transmit a first function request to the server to receive and present function feedback information transmitted by the server; wherein the first function request includes the first identity identifier;

a communication unit configured to communicate with the server.

6. A computer device, comprising: a memory, a processor, and a computer program stored on the memory and executable on the processor;

wherein the processor executes the computer program to implement the method according to claim 1.

7. A communication method, applied to a second terminal, comprising:

transmitting a second login request to a server in response to a login operation of a second user, wherein the second login request includes a second identity identifier, and the second identity identifier is allocated by the server in response to a management operation of a third user;

presenting multiple menu controls corresponding to the second identity identifier;

in response to the second user's selection operation on the menu controls, transmitting a second function request to the server, receiving and presenting function feedback information transmitted by the server, wherein the second function request includes the second identity identifier;

wherein the multiple menu controls include at least two of ward overview control, bed list control, nursing plan control, physical sign event control, surgical monitoring control, shift log control, or scheduling plan control; and wherein in response to the second user's selection operation on the menu controls, transmitting the second function request to the server, receiving and presenting function feedback information transmitted by the server, further includes at least one of the following:

in response to the second user's selection operation on the ward overview control, presenting bed information of a ward where the second user is located and corresponding patient control;

in response to the second user's selection operation on the patient control, presenting identity authentication;

in response to the second user's authentication operation of the identity authentication, presenting user information, expense information, surgery information, nursing work information, examination information, inspection information, physical sign information and medical order information of a corresponding patient;

in response to the second user's selection operation on the nursing plan control, presenting nursing plan information of the ward where the second user is located; wherein the nursing plan information includes today's physical sign measurement information, today's risk assessment information, today's nursing item information, and today's medical order information;

in response to the second user's selection operation on the physical sign event control, presenting physical sign event information of the ward where the second user is located; wherein the physical sign event information includes abnormal body temperature data information, abnormal pulse data information, abnormal breathing data information, abnormal blood pressure data information and early risk warning information;

in response to the second user's selection operation on the surgical monitoring control, presenting surgical monitoring information of the ward where the second user is located; wherein the surgical monitoring information includes patient information, medical information and status information corresponding to each surgery;

in response to the second user's selection operation on the shift log control, presenting shift log information of the ward where the second user is located; wherein the shift log information includes nursing information of each patient in the ward where the second user is located; or, in response to the second user's selection operation on the scheduling plan control, presenting scheduling plan information of the ward where the second user is located; wherein the scheduling plan information includes schedule information of each medical staff in the ward where the second user is located.

8. The communication method according to claim 7, wherein the server includes an MQTT message queue and a processor;
- wherein in response to the second user's selection operation on the menu controls, transmitting the second function request to the server, receiving and presenting function feedback information transmitted by the server, further includes:
- in response to the second user's selection operation on the menu controls, transmitting the second function request to the MQTT message queue based on the MQTT protocol, so that the MQTT message queue pushes the second function request to the processor;
- receiving and presenting the function feedback information transmitted by the server, wherein the function feedback information is transmitted by the processor according to the received second function request, and pushed to the second terminal corresponding to the second identity identifier through the MQTT message queue.

9. A terminal for implementing the communication method according to claim 7, comprising:
- a display module comprising a login control and menu controls;
- wherein the login control is configured to transmit a second login request to a server to obtain multiple corresponding menu controls according to a second identity identifier of the terminal;
- the menu controls are configured to transmit a second function request to the server to receive and present function feedback information transmitted by the server;
- wherein the second function request includes the second identity identifier;
- a communication module configured to communicate with the server.

10. The terminal according to claim 9, wherein the menu controls include at least two of ward overview control, bed list control, nursing plan control, physical sign event control, surgical monitoring control, shift log control, or scheduling plan control.

11. A computer device, comprising: a memory, a processor, and a computer program stored on the memory and executable on the processor;
- wherein the processor executes the computer program to implement the method according to claim 7.

* * * * *